United States Patent
Tellers et al.

(10) Patent No.: US 9,540,639 B2
(45) Date of Patent: *Jan. 10, 2017

(54) TETRAGALNAC CONTAINING CONJUGATES AND METHODS FOR DELIVERY OF OLIGONUCLEOTIDES

(71) Applicant: Sirna Therapeutics, Inc., Cambridge, MA (US)

(72) Inventors: David Tellers, West Point, PA (US); Steven Colletti, West Point, PA (US); Vadim Dudkin, West Point, PA (US); Norihiro Ikemoto, Rahway, NJ (US); Hongbiao Liao, Rahway, NJ (US); Craig Parish, Rahway, NJ (US); Tao Pei, Rahway, NJ (US); Anthony Shaw, West Point, PA (US); Quang Truong, Rahway, NJ (US); Lijun Wang, Whitehouse Station, NJ (US); Yu Yuan, Orlando, FL (US); Man Zhu, Rahway, NJ (US)

(73) Assignee: Sirna Therapeutics, Inc., Cambridge, MA (US)

( * ) Notice: Subject to any disclaimer, the term of this patent is extended or adjusted under 35 U.S.C. 154(b) by 140 days.

This patent is subject to a terminal disclaimer.

(21) Appl. No.: 14/398,317

(22) PCT Filed: May 1, 2013

(86) PCT No.: PCT/US2013/039025
§ 371 (c)(1),
(2) Date: Oct. 31, 2014

(87) PCT Pub. No.: WO2013/166121
PCT Pub. Date: Nov. 7, 2013

(65) Prior Publication Data
US 2015/0203843 A1    Jul. 23, 2015

Related U.S. Application Data

(60) Provisional application No. 61/641,761, filed on May 2, 2012.

(51) Int. Cl.
*C12N 15/113* (2010.01)
*A61K 47/48* (2006.01)
*C07H 15/26* (2006.01)

(52) U.S. Cl.
CPC ....... *C12N 15/113* (2013.01); *A61K 47/48092* (2013.01); *C07H 15/26* (2013.01); *C12N 2310/14* (2013.01); *C12N 2310/351* (2013.01)

(58) Field of Classification Search
CPC combination set(s) only.
See application file for complete search history.

(56) References Cited

U.S. PATENT DOCUMENTS

2009/0124571 A1    5/2009    Morvan et al.

FOREIGN PATENT DOCUMENTS

WO    2005100584 A2    10/2005
WO    2011126974 A1    10/2011

OTHER PUBLICATIONS

Deniaud et al., "Insights in the rational design of synthetic multivalent glycoconjugates as lectin ligands," Org. Biomol. Chem. 9:966-979, 2011.

*Primary Examiner* — Jennifer McDonald
(74) *Attorney, Agent, or Firm* — Jeffrey N. Townes; LeClairRyan

(57) ABSTRACT

Disclosed herein is a modular composition comprising 1) an oligonucleotide; 2) one or more tetraGalNAc ligands of Formula (I), which may be the same or different; optionally, 3) one or more linkers, which may be the same or different; and optionally, 4) one or more targeting ligands, solubilizing agents, pharmacokinetics enhancing agents, lipids, and/or masking agents.

22 Claims, No Drawings

TETRAGALNAC CONTAINING CONJUGATES AND METHODS FOR DELIVERY OF OLIGONUCLEOTIDES

CROSS-REFERENCE TO RELATED APPLICATIONS

This application claims priority to PCT Application No. PCT/US2013/039025, filed May 1, 2012, which claims benefit of priority to U.S. Provisional Application No. 61/641,761, filed May 2, 2012, both of which are incorporated herein by reference in their entirety.

BACKGROUND OF THE INVENTION

Scientific efforts focused on the delivery of oligonucleotides systemically for therapeutic purposes are ongoing. Three highlighted approaches to oligonucleotide delivery include 1) lipid nanoparticle (LNP) encapsulation, 2) polymer conjugation and 3) single chemical conjugation. Single chemical conjugation typically employs a targeting ligand or a lipid or a solubilizing group or an endosomolytic peptide or a cell penetrating peptide and/or a combination of two or all four attached to an oligonucleotide. Linkers may be present in the conjugate as well as other functionalities. Single chemical conjugates are known and attachment of the oligonucleotide occurs either at the 5'- or 3'-end of the oligonucleotide, at both ends, or internally. See WO2005/041859, WO2008/036825, and WO2009/126933.

Considerable amount of literature evidence supports the hypothesis that the major hurdles for oligonucleotide delivery are cell uptake and endosomal escape. There remains a need for additional single chemical conjugates that can provide effective delivery efficiency, cell uptake and/or endosomal escape.

SUMMARY OF THE INVENTION

Single chemical conjugates comprising tetraGalNAc ligands disclosed herein have surprising properties of improved delivery efficiency, cell uptake and/or endosomal escape.

In one embodiment, a modular composition disclosed herein comprises: 1) a single stranded or double stranded oligonucleotide; 2) one or more tetraGalNAc ligands of Formula (I), which may be the same or different:

(I)

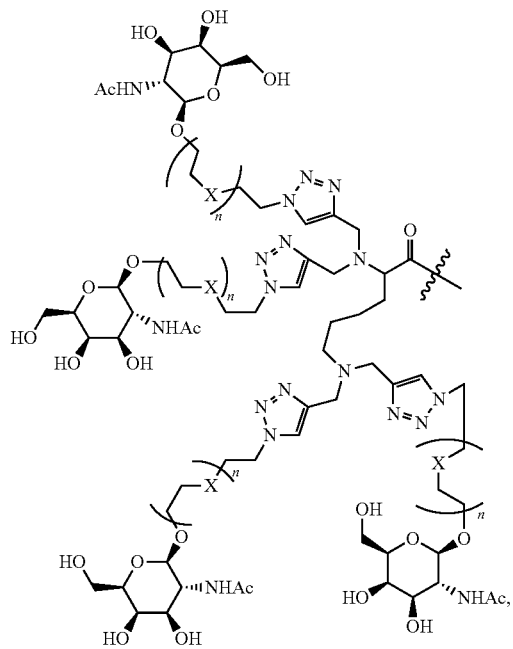

wherein X is —O—, —S—, —CR$^1$R$^2$— or —NR$^1$—, wherein R$^1$ and R$^2$ are each independently selected from the group consisting of hydrogen and C1-6alkyl; n is 1, 2, 3, or 4; and the bond with "⌇" indicates point of attachment; optionally, 3) one or more linkers, which may be the same or different; and optionally, 4) one or more targeting ligands, solubilizing agents, pharmacokinetics enhancing agents, lipids, and/or masking agents. In one embodiment, R$^1$ and R$^2$ are each independently selected from the group consisting of hydrogen, methyl and ethyl. In another embodiment, R$^1$ and R$^2$ are each hydrogen.

In one embodiment, the tetraGalNAc ligand has Formula (II) wherein X, R$^1$, R$^2$ and n are as defined above. In another embodiment, the tetraGalNAc ligand has Formula (III) wherein X, R$^1$, R$^2$ and n are as defined above:

(II)

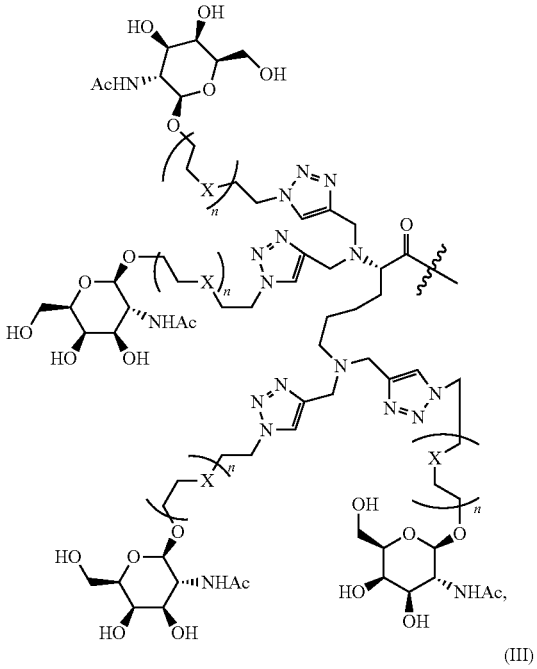

(III)

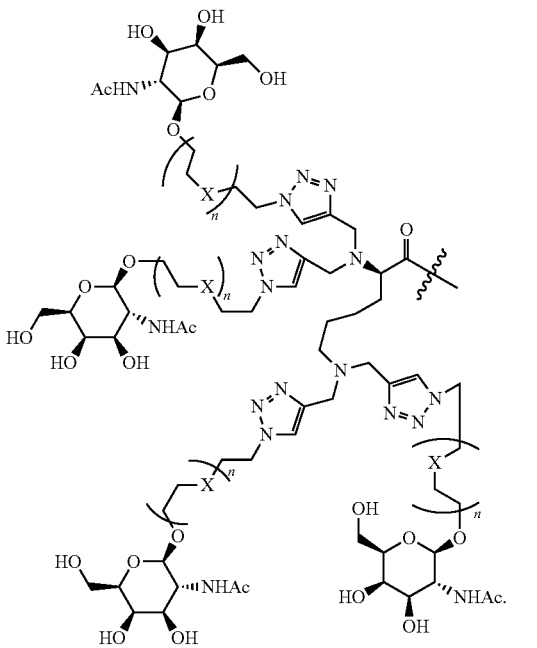

In another embodiment, a modular composition comprises: 1) a single stranded or double stranded oligonucleotide; 2) 1-8 tetraGalNAc ligands of Formula (I), (II) or (III), which may be the same or different, wherein X is —O—, —S—, —CH$_2$— or —NH—; and n is 1, 2, 3, or 4; 3) 1-24 linkers, which may be the same or different; and optionally, 4) 1-8 targeting ligands, solubilizing agents, pharmacokinetics enhancing agents, lipids, and/or masking agents.

In another embodiment, a modular composition comprises: 1) a single stranded or double stranded siRNA; 2) 1-8 tetraGalNAc ligands of Formula (I), (II) or (III), which may be the same or different, wherein X is —O—, —S—, —CH$_2$— or —NH—; and n is 1, 2, 3, or 4; 3) 1-16 linkers, which may be the same or different; and optionally, 4) 1-8 targeting ligands, solubilizing agents, pharmacokinetics enhancing agents, lipids, and/or masking agents.

In one subset of the above embodiments, the linkers are attached to the oligonucleotide or siRNA at different 2'-positions of the ribose rings and/or at different terminal 3' and/or 5'-positions of the oligonucleotide or siRNA.

In another subset of the above embodiments, the tetraGalNAc ligands are attached to the oligonucleotide or siRNA optionally via linkers.

In another subset of the above embodiments, the tetraGalNAc ligands are attached to the oligonucleotide or siRNA at different 2'-positions of the ribose rings and/or at different terminal 3' and/or 5'-positions of the oligonucleotide or siRNA; and the tetraGalNAc ligands are attached to the oligonucleotide or siRNA optionally via linkers.

In another subset of the above embodiments, X of Formula (I), (II) or (III), is —O—, —S—, or —CH$_2$—; and n is 1, 2 or 3.

In another subset of the above embodiments, X of Formula (I), (II) or (III), is —O— or —CH$_2$— and n is 1 or 2.

In another subset of the above embodiments, X of Formula (I), (II) or (III), is —O— and n is 1 or 2.

In another subset of the above embodiments, X of Formula (I), (II) or (III), is —CH$_2$— and n is 1 or 2.

In another subset of the above embodiments, the composition comprises 1-6 tetraGalNAc ligands, or more specifically, 1-4 tetraGalNAc ligands, which may be the same or different.

In another subset of the above embodiments, the oligonucleotide or siRNA is double stranded; and the tetraGalNAc ligands are attached to the guide strand or the passenger strand of the oligonucleotide or siRNA at different 2'-positions of the ribose rings.

In another subset of the above embodiments, the oligonucleotide or siRNA is double stranded; and the tetraGalNAc ligands are attached to the guide strand or the passenger strand of the oligonucleotide or siRNA at different terminal 3' and/or 5'-positions.

In another subset of the above embodiments, the oligonucleotide or siRNA is double stranded; and two or more tetraGalNAc ligands are attached to both the guide strand and the passenger strand of the oligonucleotide or siRNA at different 2'-positions of the ribose rings and/or at different terminal 3' and/or 5'-positions.

In another subset of the above embodiments, each linker is independently selected from Table 1.

In another subset of the above embodiments, each linker is independently selected from Table 2.

In another subset of the above embodiments, the oligonucleotide or siRNA is double stranded; and the optional targeting ligands, solubilizing agents, pharmacokinetics enhancing agents, lipids, and/or masking agents are attached to the same or different strands of the oligonucleotide or siRNA.

In one embodiment, a modular composition comprises 1) a double stranded siRNA; 2) 1-8 tetraGalNAc ligands of Formula (IV), (V) or (VI):

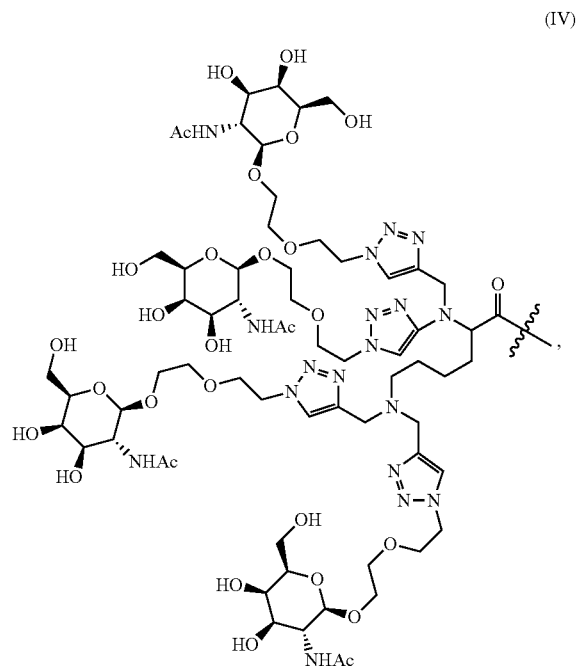 [SMILES: *C(=O)[C@@H](CCCCN(Cc1cn(CCOCCO[C@@H]2O[C@H](CO)[C@H](O)[C@H](O)[C@H]2NC(C)=O)nn1)Cc1cn(CCOCCO[C@@H]2O[C@H](CO)[C@H](O)[C@H](O)[C@H]2NC(C)=O)nn1)N(Cc1cn(CCOCCO[C@@H]2O[C@H](CO)[C@H](O)[C@H](O)[C@H]2NC(C)=O)nn1)c1cn(CCOCCO[C@@H]2O[C@H](CO)[C@H](O)[C@H](O)[C@H]2NC(C)=O)nn1 ; ";"]

(IV)

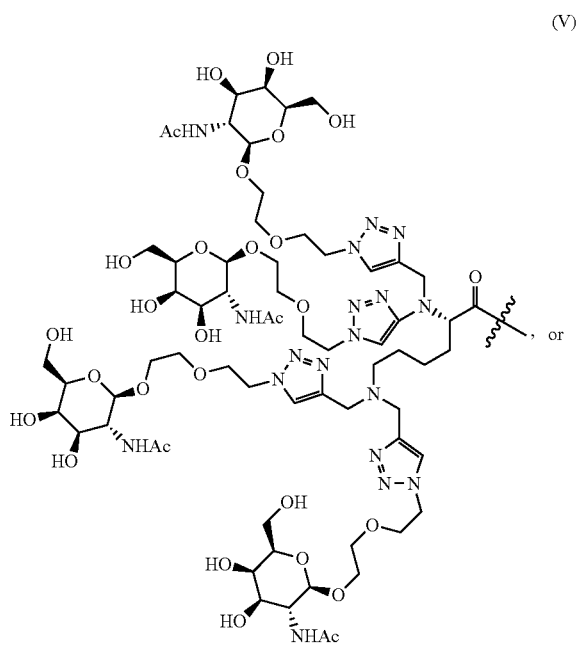

(V)

, or

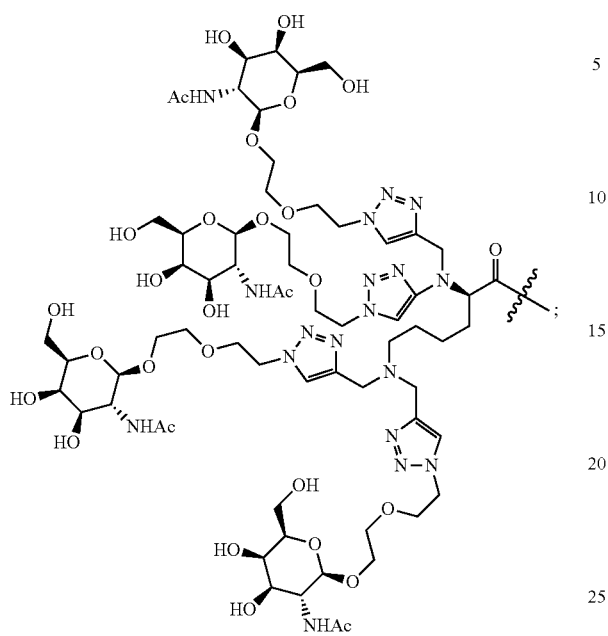

(VI)

3) 1-16 linkers independently selected from Table 1, which may be the same or different; and, optionally, 4) 1-8 targeting ligands, solubilizing agents, pharmacokinetics enhancing agents, lipids, and/or masking agents.

In another embodiment, a modular composition comprises 1) a double stranded siRNA; 2) 1-4 tetraGalNAc ligands of Formula (IV), (V) or (VI); 3) 1-8 linkers independently selected from Table 1, which may be the same or different; and, optionally, 4) 1-4 targeting ligands, solubilizing agents, pharmacokinetics enhancing agents, lipids, and/or masking agents; wherein the tetraGalNAc ligands are attached to the siRNA at different 2'-positions of the ribose rings and/or at different terminal 3' and/or 5'-positions of the siRNA; and wherein the tetraGalNAc ligands are attached to the siRNA optionally via linkers.

In one subset of the above embodiments, the tetraGalNAc ligands are attached to the same strand of the siRNA via linkers.

In one embodiment, a modular composition comprises 1) a double stranded siRNA; 2) 1-4 tetraGalNAc ligands of Formula (V); 3) 1-8 linkers independently selected from Table 2, which may be the same or different; and, optionally, 4) 1-4 targeting ligands, solubilizing agents, pharmacokinetics enhancing agents, lipids, and/or masking agents; wherein the tetraGalNAc ligands are attached to the siRNA at different 2'-positions of the ribose rings and/or at different terminal 3' and/or 5'-positions of the siRNA; and wherein the tetraGalNAc ligands are attached to the siRNA via linkers.

In one subset of the above embodiment, the tetraGalNAc ligands are attached to the same strand of the siRNA via linkers.

DETAILED DESCRIPTION OF THE INVENTION

Disclosed herein are single chemical conjugates comprising a single stranded or double stranded oligonucleotide; and one or more tetraGalNAc ligands of Formula (I), which may be the same or different:

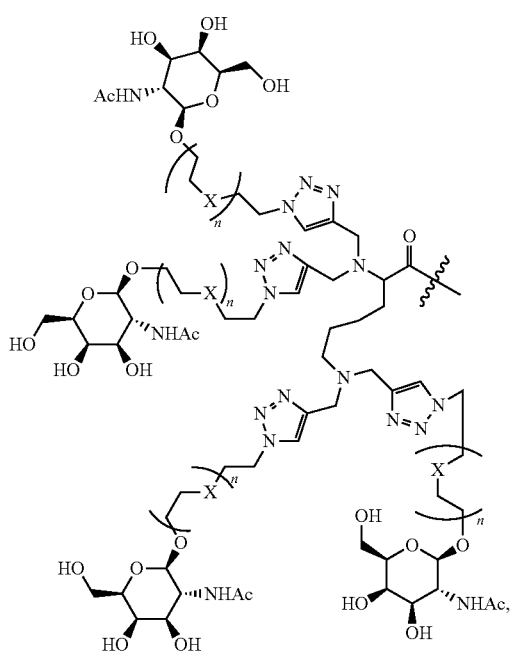

(I)

wherein X is —O—, —S—, —CR$^1$R$^2$— or —NR$^1$—, wherein R$^1$ and R$^2$ are each independently selected from the group consisting of hydrogen and C1-C6alkyl; n is 1, 2, 3, or 4; and the bond with " $\sim\!\sim\!\sim$ " indicates the point of attachment. Other functionalities, such as targeting ligands, solubilizing agents, pharmacokinetics enhancing agents, lipids, and/or masking agents are optionally present. In one embodiment, R$^1$ and R$^2$ are each independently selected from the group consisting of hydrogen, methyl and ethyl. In another embodiment, R$^1$ and R$^2$ are each hydrogen.

In one embodiment, the tetraGalNAc ligand has Formula (II) wherein X, R$^1$, R$^2$ and n are as defined above. In another embodiment, the tetraGalNAc ligand has Formula (III) wherein X, R$^1$, R$^2$ and n are as defined above:

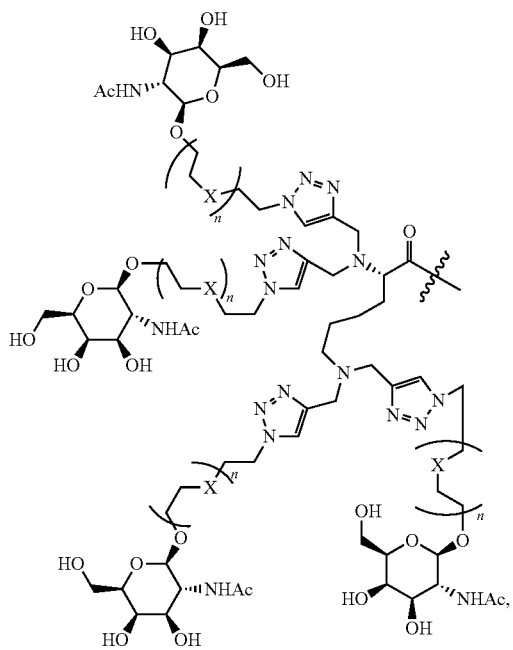

(II)

-continued (III)

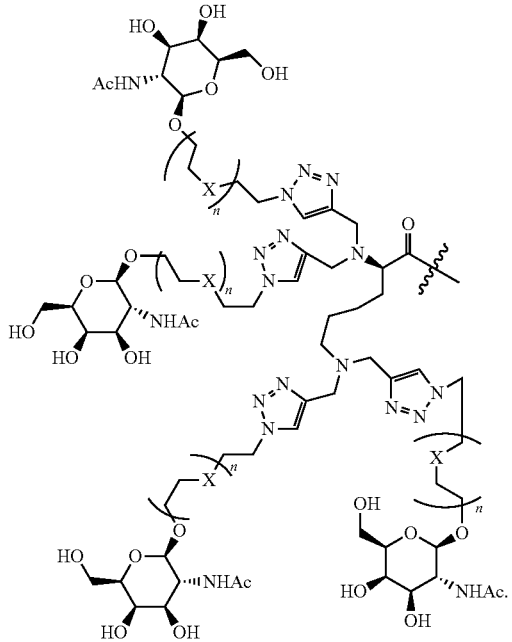

In one embodiment, the oligonucleotide is a short interfering RNA (siRNA). In another embodiment, the siRNA is a single stranded siRNA. In another embodiment, the siRNA is a double stranded siRNA.

The use of the tetraGalNAc disclosed herein may provide effective delivery of the oligonuleotide or siRNA by directing the modular composition to a particular cell. For example, the targeting ligand may specifically or non-specifically bind with a molecule on the surface of a target cell and facilitate uptake of the ligand-siRNA conjugate.

A linker may be present between each tetraGalNAc and the oligonucleotide. The linkers are attached to the oligonucleotide at different 2'-positions of the ribose rings and/or the terminal 3' and/or 5'-positions of the oligonucleotide.

In one embodiment, a modular composition comprises 1) a single stranded or double stranded oligonucleotide; 2) one or more tetraGalNAc ligands of Formula (I), which may be the same or different, wherein X is —O—, —S—, —CH$_2$— or —NH—; n is 1, 2, 3, or 4; and the bond with "⌇⌇⌇" indicates the point of attachment; optionally, 3) one or more linkers, which may be the same or different; and optionally, 4) one or more targeting ligands, solubilizing agents, pharmacokinetics enhancing agents, lipids, and/or masking agents.

In another embodiment, a modular composition comprises 1) a single stranded or double stranded oligonucleotide; 2) 1-8 tetraGalNAc ligands of Formula (I), (II) or (III), which may be the same or different, wherein X is —O—, —S—, —CH$_2$— or —NH—; n is 1, 2, 3, or 4; 3) 1-16 linkers, which may be the same or different; and optionally, 4) 1-8 targeting ligands, solubilizing agents, pharmacokinetics enhancing agents, lipids, and/or masking agents.

In another embodiment, a modular composition comprises 1) a single stranded or double stranded siRNA; 2) 1-8 tetraGalNAc ligands of Formula (I), (II) or (III), which may be the same or different, wherein X is —O—, —S—, —CH$_2$— or —NH—; n is 1, 2, 3, or 4; 3) 1-16 linkers, which may be the same or different; and optionally, 4) 1-8 targeting ligands, solubilizing agents, pharmacokinetics enhancing agents, lipids, and/or masking agents.

In one subset of the above embodiments, the tetraGalNAc ligands are attached to the oligonucleotide or siRNA at different 2'-positions of the ribose rings and/or at different terminal 3' and/or 5'-positions of the oligonucleotide or siRNA. In another subset of the above embodiments, the tetraGalNAc ligands are attached to the oligonucleotide or siRNA optionally via linkers. In one embodiment, the linkers are present.

In another subset of the above embodiments, the tetraGalNAc ligands are attached to the oligonucleotide or siRNA at different 2'-positions of the ribose rings and/or at different terminal 3' and/or 5'-positions of the oligonucleotide or siRNA; and the tetraGalNAc ligands are attached to the oligonucleotide or siRNA via linkers.

In another subset of the above embodiments, the tetraGalNAc ligands are attached to the oligonucleotide or siRNA via linkers and the linkers are attached to the oligonucleotide or siRNA at different 2'-positions of the ribose rings.

In another subset of the above embodiments, the tetraGalNAc ligands are attached to the oligonucleotide or siRNA via linkers and the linkers are attached to the oligonucleotide or siRNA at different terminal 3' and/or 5'-positions of the oligonucleotide.

In another subset of the above embodiments, X is —O—, —S—, or —CH$_2$—. In another embodiment, X is —O— or —CH$_2$—. In another embodiment, n is 1, 2 or 3. In another embodiment, X is —O— and n is 1 or 2. In another embodiment, X is —CH$_2$— and n is 1 or 2. In another embodiment, X is —O— and n is 1. In yet another embodiment, X is —CH$_2$— and n is 1.

In another subset of the above embodiments, the oligonucleotide or siRNA is single stranded. In another embodiment, the oligonucleotide or siRNA is double stranded. In another subset of the above embodiments, the composition comprises 1-6 tetraGalNAc ligands. In another embodiment, the composition comprises 1-4 tetraGalNAc ligands. In another embodiment, the composition comprises 1-2 tetraGalNAc ligands. In yet another embodiment, the composition comprises 1 tetraGalNAc ligand.

In another subset of the above embodiments, the oligonucleotide or siRNA is double stranded and the tetraGalNAc ligands are attached to the guide strand at different 2'-positions of the ribose rings.

In another subset of the above embodiments, the oligonucleotide or siRNA is double stranded the tetraGalNAc ligands are attached to the guide strand at different terminal 3' and/or 5'-positions.

In another subset of the above embodiments, the oligonucleotide or siRNA is double stranded and the tetraGalNAc ligands are attached to the passenger strand at different 2'-positions of the ribose rings.

In another subset of the above embodiments, the oligonucleotide or siRNA is double stranded and the tetraGalNAc ligands are attached to the passenger strand at different terminal 3' and/or 5'-positions.

In another subset of the above embodiments, the oligonucleotide or siRNA is double stranded and the tetraGalNAc ligands are attached to both the guide strand and the passenger strand at different 2'-positions of the ribose rings and/or different terminal 3' and/or 5'-positions.

In another subset of the above embodiments, the oligonucleotide or siRNA is double stranded and the tetraGalNAc ligands are attached to the same strand.

In another subset of the above embodiments, the oligonucleotide or siRNA is double stranded and the tetraGalNAc ligands are attached to different strands.

In another subset of the above embodiments, the oligonucleotide or siRNA is double stranded and the optional targeting ligands, solubilizing agents, pharmacokinetics enhancing agents, lipids, and/or masking agents are attached to the same or different strands.

In another subset of the above embodiments, the oligonucleotide or siRNA is double stranded and the optional targeting ligands, solubilizing agents, pharmacokinetics enhancing agents, lipids, and/or masking agents are attached to the same or different strands via linkers. In one embodiment, each linker is independently selected Table 1. In another embodiment, each linker is independently selected Table 2.

In one embodiment, a modular composition comprises 1) a single stranded or double stranded siRNA; 2) 1-8 tetraGalNAc ligands of Formula (I), (II) or (III), which may be the same or different; wherein X is —O—, —S—, —CH$_2$— or —NH—; and n is 1, 2, 3, or 4; 3) 1-16 linkers, which may be the same or different; and optionally, 4) 1-8 targeting ligands, solubilizing agents, pharmacokinetics enhancing agents, lipids, and/or masking agents; wherein the tetraGalNAc ligands are attached to the siRNA at different 2'-positions of the ribose rings and/or at different terminal 3' and/or 5'-positions of the siRNA; and wherein the tetraGalNAc ligands are attached to the siRNA optionally via linkers. In one embodiment, the linkers are present. In another embodiment, X is —O—, —S—, or —CH$_2$—, and n is 1, 2 or 3. In another embodiment, X is —O— or —CH$_2$—, and n is 1 or 2.

In another embodiment, a modular composition comprises 1) a double stranded siRNA; 2) 1-6 tetraGalNAc ligands of Formula (I), which may be the same or different; wherein X is —O—, —S—, or —CH$_2$-; and n is 1, 2 or 3; 3) 1-18 linkers, which may be the same or different; and optionally, 4) 1-6 targeting ligands, solubilizing agents, pharmacokinetics enhancing agents, lipids, and/or masking agents; wherein the tetraGalNAc ligands are attached to the siRNA at different 2'-positions of the ribose rings and/or at different terminal 3' and/or 5'-positions of the siRNA; and wherein the tetraGalNAc ligands are attached to the siRNA optionally via linkers. In one embodiment, the linkers are present. In another embodiment, X is —O—, —S—, or —CH$_2$— and n is 1 or 2. In another embodiment, the linkers are independently selected from Table 1. In another embodiment, the linkers are independently selected from Table 2.

In another embodiment, a modular composition comprises 1) a double stranded siRNA; 2) 1-4 tetraGalNAc ligands of Formula (I), which may be the same or different; wherein X is —O—, —S—, or —CH$_2$—; and n is 1 or 2; 3) 1-8 linkers, which may be the same or different; and optionally, 4) 1-4 targeting ligands, solubilizing agents, pharmacokinetics enhancing agents, lipids, and/or masking agents; wherein the tetraGalNAc ligands are attached to the siRNA at different 2'-positions of the ribose rings and/or at different terminal 3' and/or 5'-positions of the siRNA; and wherein the tetraGalNAc ligands are attached to the siRNA via linkers. In one embodiment, X is —O— or —CH$_2$— and n is 1 or 2. In another embodiment, the linkers are independently selected from Table 1. In another embodiment, the linkers are independently selected from Table 2.

In another embodiment, a modular composition comprises 1) a double stranded siRNA; 2) 1-4 tetraGalNAc ligands of Formula (IV), (V) or (VI):

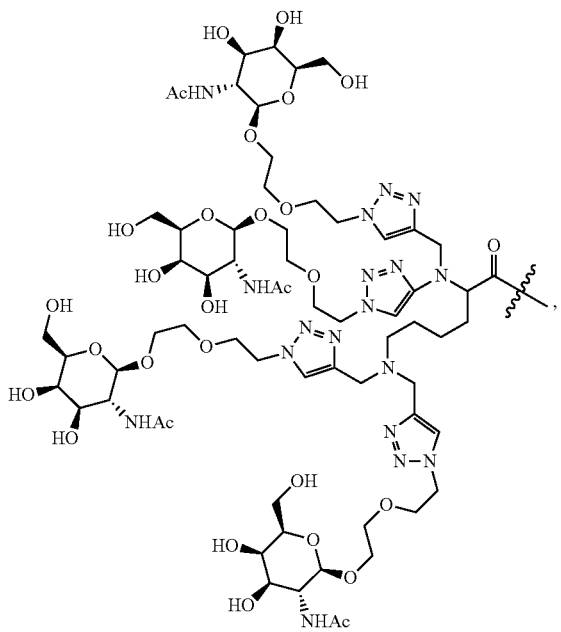

(IV)

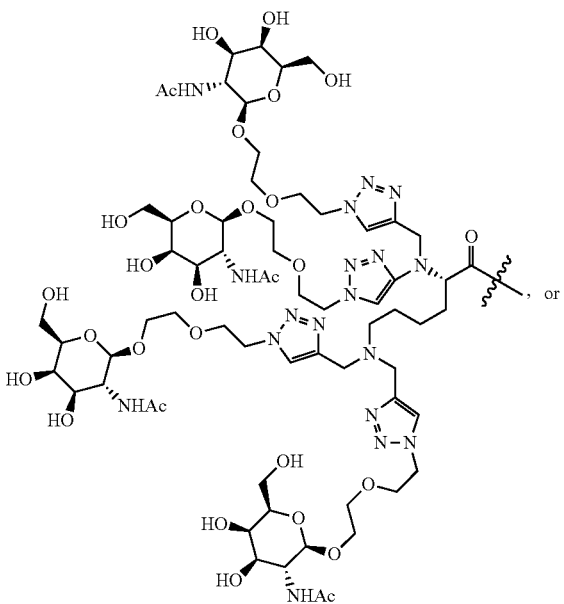

(V)

, or

-continued (VI)

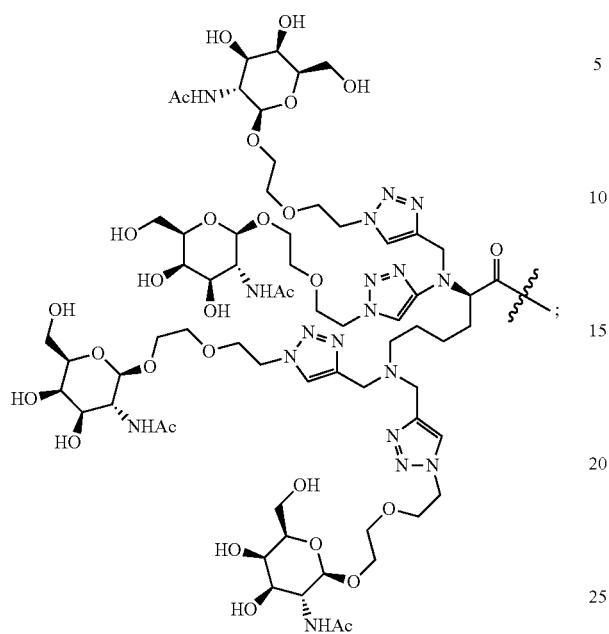

3) 1-8 linkers independently selected from Table 1, which may be the same or different; and optionally, 4) 1-4 targeting ligands, solubilizing agents, pharmacokinetics enhancing agents, lipids, and/or masking agents; wherein the tetraGalNAc ligands are attached to the siRNA at different 2'-positions of the ribose rings and/or at different terminal 3' and/or 5'-positions of the siRNA; and wherein the tetraGalNAc ligands are attached to the siRNA via linkers.

In another embodiment, a modular composition comprises 1) a double stranded siRNA; 2) 1-4 tetraGalNAc ligands of Formula (V); 3) 1-8 linkers independently selected from Table 2, which may be the same or different; and optionally, 4) 1-4 targeting ligands, solubilizing agents, pharmacokinetics enhancing agents, lipids, and/or masking agents; wherein the tetraGalNAc ligands are attached to the siRNA at different 2'-positions of the ribose rings and/or at different terminal 3' and/or 5'-positions of the siRNA; and wherein the tetraGalNAc ligands are attached to the siRNA via linkers.

In one subset of the above embodiments, the tetraGalNAc ligands are attached to the siRNA via linkers; and wherein the tetraGalNAc ligands are attached to the same strand.

In another subset of the above embodiments, the tetraGalNAc ligands are attached to the siRNA via linkers; and wherein the tetraGalNAc ligands are attached to different strands.

To illustrate the invention via cartoon, the invention features a modular composition, comprising an oligonucleotide ($[O_1][O_2][O_3] \ldots [O_n]$), one or more linkers (L), one or more tetraGalNAc ligands (G), and one or more optional lipid(s) (X), targeting ligand(s) (X), and/or solubilizing group(s) (X).

In an embodiment, the modular composition may have the formula:

G-L-$[O_1][O_2][O_3] \ldots [O_n]$.

In another embodiment, the modular composition may have the formula:

G-L-$[O_1][O_2][O_3] \ldots [O_n]$—X.

Non-limiting examples of modular compositions comprising double stranded oligonucleotides with terminal conjugations are:

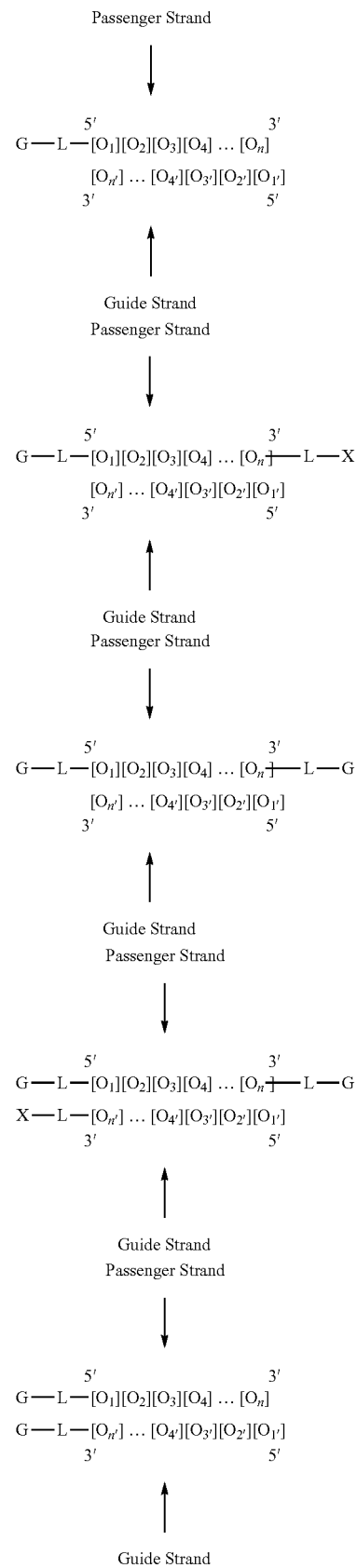

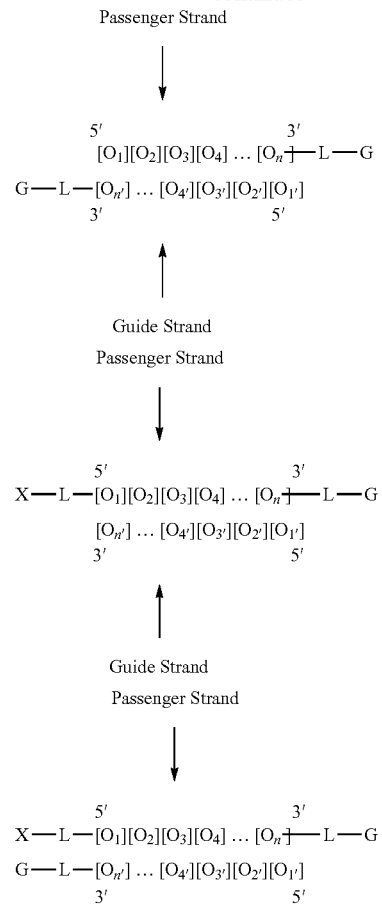
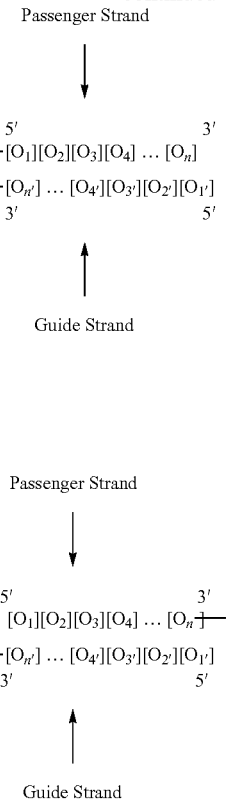
Non-limiting examples of modular compositions comprising double stranded oligonucleotides with internal conjugations are:
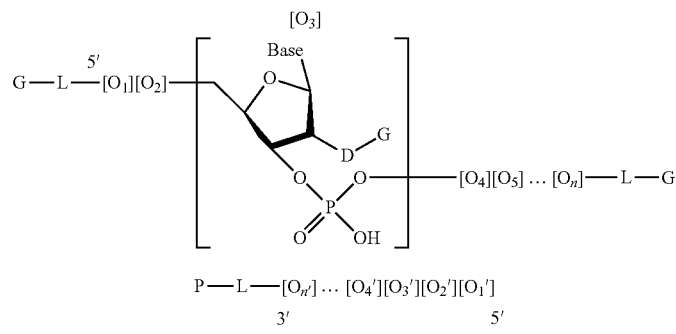

Passenger Strand

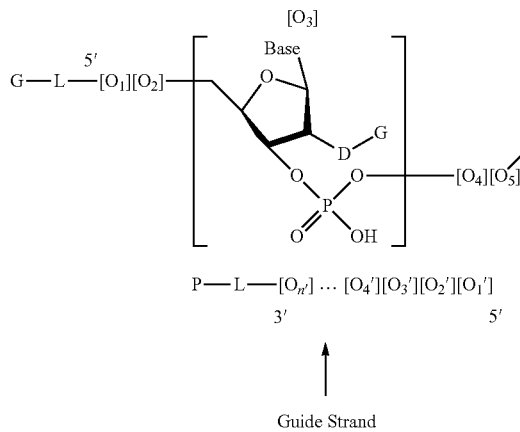

Guide Strand

These examples are used as illustration only. One skilled in the art will recognize that a variety of permutations for placing the desired components on the passenger and guide strands exist.

Any number of linkers, and therefore any number of tetraGalNAc ligands, can be attached to the oligonucleotide. A preferred range of numbers of linkers is from 1-16. A more preferred range of numbers of linkers is from 1-8, or more specifically, 1-4. A preferred range of numbers of tetraGal-NAc ligands is from 1-8. A more preferred range of numbers of peptides is from 1-8, or more specifically, 1-4.

The two strands contain n and n' nucleotides respectively. The numbers n and n' can be equal or different. The numbers are integers ranging from 8 to 50. Preferably, the numbers are integers ranging from 12-28. More preferably, the numbers are integers ranging from 19-21.

As an example, each nucleotide $[O_n]$ or $[O_{n'}]$, that contains a linker (L-G and/or L-X) has generic structures shown in the following cartoon:

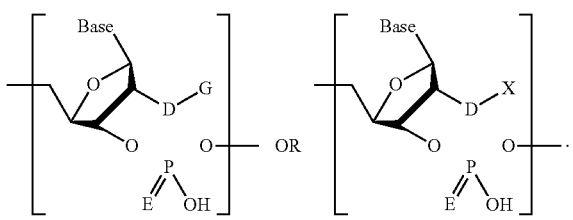

For each nucleotide, 1) E=oxygen (O) or sulfur (S); 2) Base=A, U, G or C, which can be modified or unmodified; 3) D is the connection point between ribose ring and linker L, D=oxygen (O), sulfur (S, S(O) or S(O)$_2$), nitrogen (N—R, wherein R═H, alkyl, L-P or L-X), carbon (CH—R, wherein R═H, alkyl, L-P, or L-X), or phosphorus (P(O)R or P(O)(OR), wherein R=alkyl, L-G, or L-X). Preferably, D=oxygen (O).

The two nucleotides $[O_{n-1}]$ and $[O_n]$ or $[O_{n'-1}]$ and $[O_{n'}]$ are connected via phosphodiester or thio-phosphodiester bonds.

When the oligonucleotide is a double-stranded oligonucleotide, the "G-L" and the lipid, targeting ligand, and/or solubilizing group may be located on the same strand or on different strands.

In some embodiments, the "G-L" and the lipid, targeting ligand, and/or solubilizing group are on the same strand.

In some embodiments, the "G-L" and the lipid, targeting ligand, and/or solubilizing group are on the passenger strand.

In some embodiments, the "G-L" and the lipid, targeting ligand, and/or solubilizing group are on the guide strand.

In some embodiments, the "G-L" and the lipid, targeting ligand, and/or solubilizing group are located on different strands.

In some embodiments, the "G-L" is on the passenger strand while the lipid, targeting ligand, and/or solubilizing group is on the guide strand.

In some embodiments, the "G-L" and the lipid, targeting ligand, and/or solubilizing group are on different strands but on the same terminal end of the double-stranded oligonucleotide.

In some embodiments, the "G-L" and the lipid, targeting ligand, and/or solubilizing group are on different strands and on the opposite terminal ends of the double-stranded oligonucleotide.

In some embodiments, an additional "G-L" of identical or different nature can be used in place of the lipid, targeting ligand, and/or solubilizing group noted in the above embodiments.

In some embodiments, the "G-L" can be located on multiple terminal ends of either the passenger or guide strand and the the lipid, targeting ligand, and/or solubilizing group can be located on the remaining terminal ends of the passenger and guide strands.

In some embodiments, one "G-L" and two or more lipids, targeting ligands, and/or solubilizing groups are present in the oligonucleotide.

In some embodiments, two or more "G-L" and two or more lipids, targeting ligands and/or solubilizing groups are present in the oligonucleotide.

In some embodiments, when the oligonucleotide is a double-stranded oligonucleotide and multiple "G-L" components and/or lipids, targeting ligands, and/or solubilizing groups are present, such multiple "G-L" components and/or lipids, targeting ligands, and/or solubilizing groups may all be present in one strand or both strands of the double stranded oligonucleotide.

When multiple "G-L" components and/or lipids, targeting ligands, and/or solubilizing groups are present, they may all be the same or different.

In some embodiments, the "G-L" are on internal nucleotides only (i.e. excluding the 3'- and 5'-terminal ends of the oligonucleotide).

In another aspect, the invention includes a method of delivering an oligonucleotide or siRNA to a cell. The method includes (a) providing or obtaining a modular composition disclosed herein; (b) contacting a cell with the modular composition; and (c) allowing the cell to internalize the modular composition.

The method can be performed in vitro, ex vivo or in vivo, e.g., to treat a subject identified as being in need of an oligonucleotide or siRNA. A subject in need of said oligonucleotide is a subject, e.g., a human, in need of having the expression of a gene or genes, e.g., a gene related to a disorder, downregulated or silenced.

In one aspect, the invention provides a method for inhibiting the expression of one or more genes. The method comprising contacting one or more cells with an effective amount of an oligonucleotide of the invention, wherein the effective amount is an amount that suppresses the expression of the one or more genes. The method can be performed in vitro, ex vivo or in vivo.

The methods and compositions of the invention, e.g., the modular composition described herein, can be used with any oligonucleotides or siRNAs known in the art. In addition, the methods and compositions of the invention can be used for the treatment of any disease or disorder known in the art, and for the treatment of any subject, e.g., any animal, any mammal, such as any human. One of ordinary skill in the art will also recognize that the methods and compositions of the invention may be used for the treatment of any disease that would benefit from downregulating or silencing a gene or genes.

The methods and compositions of the invention, e.g., the modular composition described herein, may be used with any dosage and/or formulation described herein, or any dosage or formulation known in the art. In addition to the routes of administration described herein, a person skilled in the art will also appreciate that other routes of administration may be used to administer the modular composition of the invention.

Oligonucleotide

An "oligonucleotide" as used herein, is a double stranded or single stranded, unmodified or modified RNA or DNA Examples of modified RNAs include those which have greater resistance to nuclease degradation than do unmodified RNAs. Further examples include those which have a 2' sugar modification, a base modification, a modification in a single strand overhang, for example a 3' single strand overhang, or, particularly if single stranded, a 5' modification which includes one or more phosphate groups or one or more analogs of a phosphate group. Examples and a further description of oligonucleotides can be found in WO2009/126933, which is hereby incorporated by reference.

In an embodiment, an oligonucleotide is an antisense, miRNA, peptide nucleic acid (PNA), poly-morpholino (PMO) or siRNA. The preferred oligonucleotide is an siRNA. Another preferred oligonuleotide is the passenger strand of an siRNA. Another preferred oligonucleotide is the guide strand of an siRNA.

siRNA siRNA directs the sequence-specific silencing of mRNA through a process known as RNA interference (RNAi). The process occurs in a wide variety of organisms, including mammals and other vertebrates. Methods for preparing and administering siRNA and their use for specifically inactivating gene function are known. siRNA includes modified and unmodified siRNA. Examples and a further description of siRNA can be found in WO2009/126933, which is hereby incorporated by reference.

A number of exemplary routes of delivery are known that can be used to administer siRNA to a subject. In addition, the siRNA can be formulated according to any exemplary method known in the art. Examples and a further description of siRNA formulation and administration can be found in WO2009/126933, which is hereby incorporated by reference.

The phrases "short interfering nucleic acid", "siNA", "short interfering RNA", "siRNA", "short interfering nucleic acid molecule", "oligonucleotide", "short interfering oligonucleotide molecule", or "chemically modified short interfering nucleic acid molecule" refer to any nucleic acid molecule capable of inhibiting or down regulating gene expression or viral replication by mediating RNA interference ("RNAi") or gene silencing in a sequence-specific manner. These terms can refer to both individual nucleic acid molecules, a plurality of such nucleic acid molecules, or pools of such nucleic acid molecules. The siNA can be a double-stranded nucleic acid molecule comprising self-complementary sense and antisense strands, wherein the antisense strand comprises a nucleotide sequence that is complementary to a nucleotide sequence in a target nucleic acid molecule or a portion thereof and the sense strand comprises a nucleotide sequence corresponding to the target nucleic acid sequence or a portion thereof. The siNA can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region comprises a nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to a nucleotide sequence in a target nucleic acid molecule or a portion thereof and the sense region comprises a nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single-stranded polynucleotide having a nucleotide sequence complementary to nucleotide sequence in a target nucleic acid molecule or a portion thereof (for example, where such siNA molecule does not require the presence within the siNA molecule of a nucleotide sequence corresponding to the target nucleic acid sequence or a portion thereof), wherein the single-stranded polynucleotide can further comprise a terminal phosphate group, such as a 5'-phosphate (see for example, Martinez et al., 2002, *Cell*, 110, 563-574 and Schwarz et al., 2002, *Molecular Cell*, 10, 537-568), or 5',3'-diphosphate.

Linkers

The covalent linkages between the tetraGalNAc and the oligonucleotide or siRNA of the modular composition may be mediated by a linker. This linker may be cleavable or non-cleavable, depending on the application. In certain embodiments, a cleavable linker may be used to release the oligonucleotide after transport from the endosome to the cytoplasm. The intended nature of the conjugation or coupling interaction, or the desired biological effect, will determine the choice of linker group. Linker groups may be combined or branched to provide more complex architectures. Suitable linkers include those as described in WO2009/126933, which is hereby incorporated by reference.
In one embodiment, the linkers of the instant invention are shown in Table 1:
TABLE 1
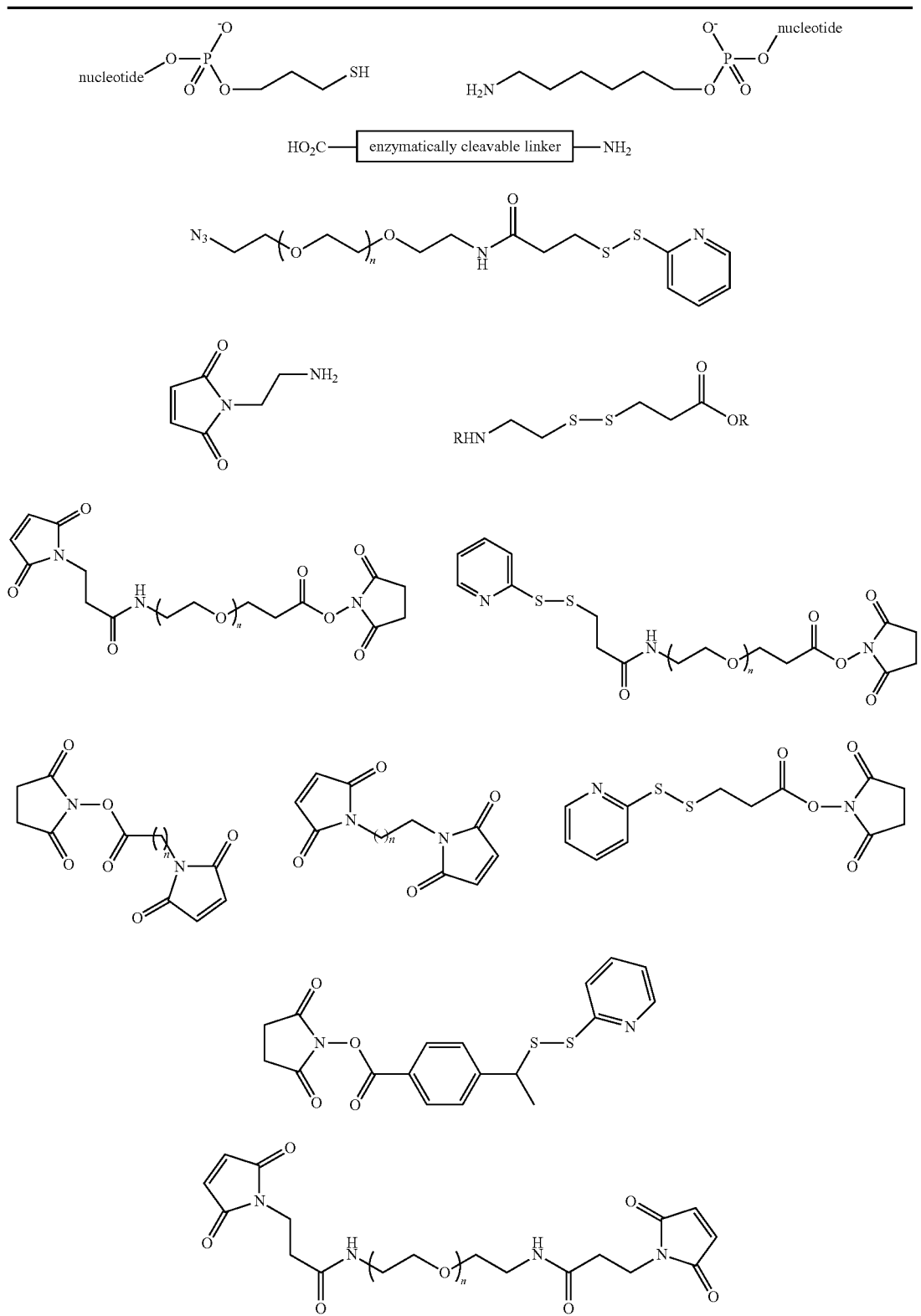

TABLE 1-continued
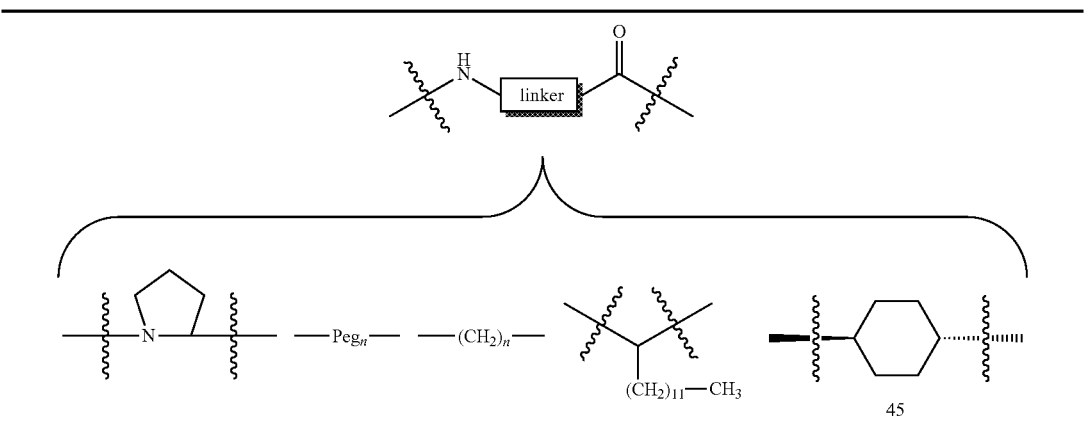
R = H, Boc, Cbz, Ac, PEG, lipid, targeting ligand, linker(s) and/or peptide(s).
n = 0 to 750.
"nucleotide" can be substituted with non-nucleotide moiety such as abasic or linkers as are generally known in the art.
In another embodiment, the preferred linkers are shown in Table 2:
TABLE 2
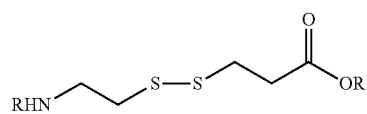
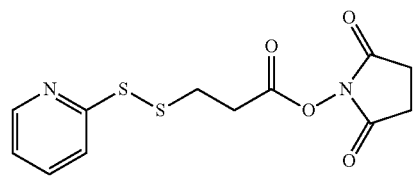 [SMILES: O=C(CCSSc1ccccn1)ON1C(=O)CCC1=O]
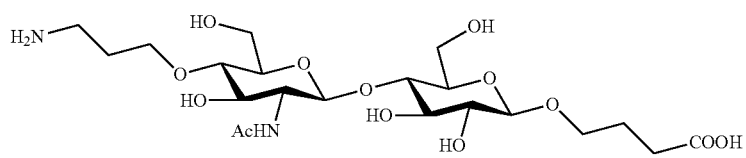
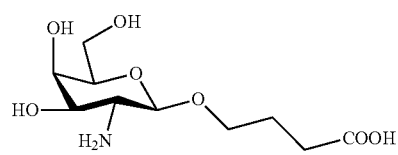

TABLE 2-continued

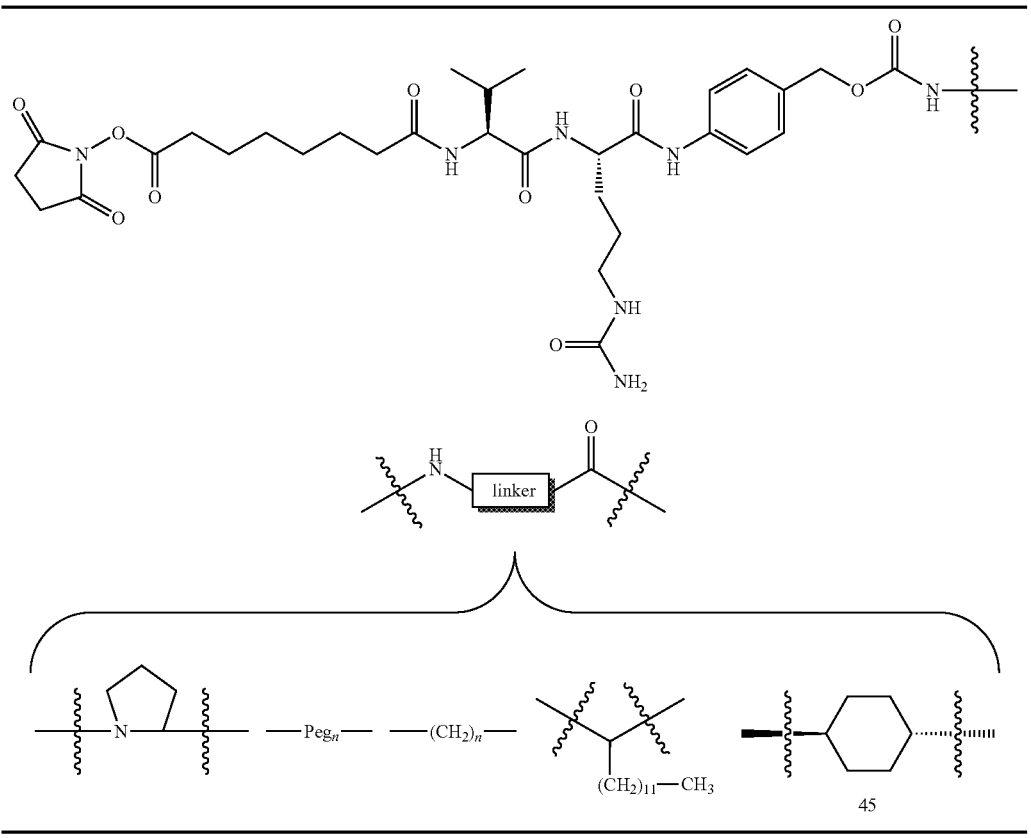

R = H, Boc, Cbz, Ac, PEG, lipid, targeting ligand, linker(s) and/or peptide(s).
n = 0 to 750.
"nucleotide" can be substituted with non-nucleotide moiety such as abasic or linkers as are generally known in the art.

Commercial linkers are available from various suppliers such as Pierce or Quanta Biodesign including combinations of said linkers. In addition, commercial linkers attached via phosphate bonds can be used independently as linkers or in combination with said linker. The linkers may also be combined to produce more complex branched architectures accommodating from 1 to 8 tetraGalNAc ligands as illustrated in one such example below:

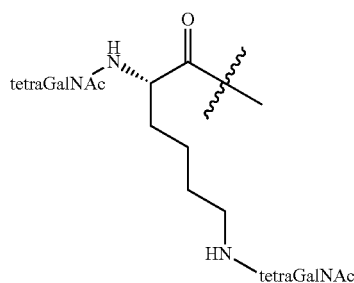

Targeting Ligands

The modular compositions of the present invention may comprise a targeting ligand. In some embodiments, this targeting ligand may direct the modular composition to a particular cell. For example, the targeting ligand may specifically or non-specifically bind with a molecule on the surface of a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell. Examples and a further description of targeting ligands can be found in WO2009/126933, which is hereby incorporated by reference.

The targeting ligands are selected from the group consisting of an antibody, a ligand-binding portion of a receptor, a ligand for a receptor, an aptamer, D-galactose, N-acetyl-D-galactose (GalNAc), multivalent N-acetyl-D-galactose, D-mannose, cholesterol, a fatty acid, a lipoprotein, folate, thyrotropin, melanotropin, surfactant protein A, mucin, carbohydrate, multivalent lactose, multivalent galactose, N-acetyl-galactosamine, N-acetyl-glucosamine, multivalent mannose, multivalent fructose, glycosylated polyaminoacids, transferin, bisphosphonate, polyglutamate, polyaspartate, a lipophilic moiety that enhances plasma protein binding, a steroid, bile acid, vitamin B12, biotin, an RGD peptide, an RGD peptide mimic, ibuprofen, naproxen, aspirin, folate, and analogs and derivatives thereof.

The preferred targeting ligands are selected from the group consisting of D-galactose, N-acetyl-D-galactose (GalNAc), GalNAc2, and GalNAc3, cholesterol, folate, and analogs and derivatives thereof.

Lipids

Lipophilic moieties, such as cholesterol or fatty acids, when attached to highly hydrophilic molecules such as nucleic acids can substantially enhance plasma protein binding and consequently circulation half life. In addition, lipophilic groups can increase cellular uptake. For example, lipids can bind to certain plasma proteins, such as lipoproteins, which have consequently been shown to increase uptake in specific tissues expressing the corresponding lipoprotein receptors (e.g., LDL-receptor or the scavenger receptor SR-B1). Lipophilic conjugates can also be considered as a targeted delivery approach and their intracellular trafficking could potentially be further improved by the combination with endosomolytic agents.

Exemplary lipophilic moieties that enhance plasma protein binding include, but are not limited to, sterols, cholesterol, fatty acids, cholic acid, lithocholic acid, dialkylglycerides, diacylglyceride, phospholipids, sphingolipids, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, phenoxazine, aspirin, naproxen, ibuprofen, vitamin E and biotin etc. Examples and a further description of lipids can be found in WO2009/126933, which is hereby incorporated by reference.

The preferred lipid is cholesterol.

Solubilizing Agents

The modular composition may comprise one or more other moieties/ligands that may enhance aqueous solubility, circulation half life and/or cellular uptake. These can include naturally occurring substances, such as a protein (e.g., human serum albumin (HSA), low-density lipoprotein (LDL), high-density lipoprotein (HDL), or globulin); or a carbohydrate (e.g., a dextran, pullulan, chitin, chitosan, inulin, cyclodextrin or hyaluronic acid). These moieties may also be a recombinant or synthetic molecule, such as a synthetic polymer or synthetic polyamino acids. Examples include polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG, e.g., PEG-0.5K, PEG-2K, PEG-5K, PEG-10K, PEG-12K, PEG-15K, PEG-20K, PEG-40K), methyl-PEG (mPEG), [mPEG]2, polyvinyl alcohol (PVA), polyurethane, poly(2 ethylacrylic acid), N-isopropylacrylamide polymers, or polyphosphazine. Examples and a further description of solubilizing agents can be found in WO2009/126933, which is hereby incorporated by reference.

The preferred solubilizing group is PEG 0.5K to 30K.

Method of Treatment

In one aspect, the invention features, a method of treating a subject at risk for or afflicted with a disease that may benefit from the administration of the modular composition of the invention. The method comprises administering the modular composition of the invention to a subject in need thereof, thereby treating the subject. The oligonucleotide that is administered will depend on the disease being treated. See WO2009/126933 for additional details regarding methods of treatments for specific indications.

Formulation

There are numerous methods for preparing conjugates of oligonucleotide compounds. The techniques should be familiar to those skilled in the art. A useful reference for such reactions is Bioconjugate Techniques, Hermanson, G. T., Academic Press, San Diego, Calif., 1996. Other references include WO2005/041859; WO2008/036825 and WO2009/126933.

EXAMPLES

The invention is further illustrated by the following examples, which should not be construed as further limiting. The contents of all references, pending patent applications and published patents, cited throughout this application are hereby expressly incorporated by reference. The siRNAs described herein were designed to target the ubiquitously expressed gene SSB (Sjogren syndrome antigen B; NM_009278.4).

Linker groups may be connected to the oligonucleotide or siRNA strand(s) at a linkage attachment point (LAP) and may include any carbon-containing moiety, in some embodiments having at least one oxygen atom, at least one phosphorous atom, and/or at least one nitrogen atom. In some embodiments, the phosphorous atom forms part of a terminal phosphate, or phosphorothioate, group on the linker group, which may serve as a connection point for the oligonucleotide strand. In certain embodiments, the nitrogen atom forms part of a terminal ether, ester, amino or amido (NHC(O)—) group on the linker group, which may serve as a connection point for the linkers of interest, endosomolytic unit, cell penetrating peptide, solubilizing group, lipid, targeting group, or additional linkers of interest. These terminal linker groups include, but are not limited to, a $C_6$ hexyl, $C_5$ secondary-hydroxy, $C_3$ thiol or $C_6$ thiol moiety. An example from the RNA sequences described below is C6 hexyl: [$(CH_2)_6$ $NH_2$].

Preparations of tetraGalNAc ligands and tetraGalNAc-siRNA conjugates are described below in the Examples and synthetic schemes. Specific siRNA sequences used for the compounds and/or conjugates described below are shown in Table 3.

TABLE 3 siRNA sequences used for exemplary compounds and/or conjugates.

| Entry | Gene Target | Strand | SEQ ID NO | Sequence | Duplex Code |
|---|---|---|---|---|---|
| 1 | ApoB | Passenger | 1 | [6amiL][iB][omeC][omeU][omeU][omeU][omeU][fluA][fluA][omeC][fluA][fluA][omeU][omeU][omeC][omeC][omeU][fluG][fluA][fluA][fluA][omeU][dTs][dT][iB] | 51 |
|  | ApoB | Guide | 2 | [rAs][rUs][rUs][omeU][omeC][fluA][fluG][fluG][fluA][fluA][omeU][omeU][fluG][fluU][omeU][fluA][fluA][fluA][fluG][omeUs][omeU] |  |
| 2 | ApoB | Passenger | 3 | [6amiL][iB][omeC][omeU][omeU][omeU][fluA][fluA][omeC][fluA][fluA][omeU][omeU][omeC][omeC][omeU][fluG][fluA][fluA][fluA][omeU][dTs]dT[iB][6amiL] | 52 |
|  | ApoB | Guide | 4 | [rAs][rUs][rUs][omeU][omeC][fluA][fluG][fluG][fluA][fluA][omeU][omeU][fluG][fluU][omeU][fluA][fluA][fluA][fluG][omeUs][omeU] |  |

TABLE 3-continued siRNA sequences used for exemplary compounds and/or conjugates.

| Entry | Gene Target | Strand | SEQ ID NO | Sequence | Duplex Code |
|---|---|---|---|---|---|
| 3 | ApoB | Passenger | 5 | [6amiL][iB][omeC][omeU][clickU][omeU][fluA][fluA][omeC][fluA][fluA][omeU][omeU][omeC][omeC][omeU][fluG][fluA][clickA][fluA][omeU][dTs]dT[iB] | 53 |
|   | ApoB | Guide | 6 | [rAs][rUs][rUs][omeU][omeC][fluA][fluG][fluG][fluA][fluA][omeU][omeU][fluG][fluU][omeU][fluA][fluA][fluA][fluG][omeUs][omeU] |  |
| 4 | ApoB | Passenger | 7 | [iB][omeC][omeU][omeU][omeU][fluA][fluA][omeC][fluA][fluA][omeU][omeU][omeC][omeC][omeU][fluG][fluA][fluA][fluA][omeU][dTs]dT[iB][6amiL] | 54 |
|   | ApoB | Guide | 8 | [rAs][rUs][rUs][omeU][omeC][fluA][fluG][fluG][fluA][fluA][omeU][omeU][fluG][fluU][omeU][fluA][fluA][fluA][fluG][omeUs][omeU] |  |
| 5 | ApoB | Passenger | 9 | [6amiL][iB][omeC][omeU][omeU][omeU][fluA][fluA][omeC][fluA][fluA][omeU][omeU][omeC][omeC][omeU][fluG][fluA][fluA][fluA][omeU][dTs]dT[iB] | 55 |
|   | ApoB | Guide | 10 | [rAs][rUs][rUs][omeU][omeC][fluA][fluG][fluG][fluA][fluA][omeU][omeU][fluG][flu][propargylU][fluA][fluA][fluA][fluG][omeUs][omeU] |  |
| 6 | SSB | Passenger | 11 | [6amiL][iB][fluA][omeC][fluA][fluA][omeC][fluA][fluG][fluA][omeC][omeU][omeU][omeU][fluA][fluA][omeU][fluG][omeU][fluA][fluA][dTs]dT[iB] | 56 |
|   | SSB | Guide | 12 | [rUs][rUs][rAs][omeC][fluA][omeU][omeU][fluA][fluA][fluA][fluG][omeC][fluU][fluG][omeU][omeU][fluG][omeU][omeUs][omeU] |  |
| 7 | CTNNB1 | Passenger | 13 | [6amiL][iB][omeC][omeU][clickG][omeU][omeU][fluG][fluG][fluA][omeU][omeU][fluG][fluA][omeU][omeU][omeC][fluG][clickA][fluA][fluA][omeUs][omeU][iB] | 57 |
|   | CTNNB1 | Guide | 14 | [omeUs][fluUs][omeUs][fluC][omeG][fluA][omeA][fluU][omeC][fluA][omeA][fluU][omeC][fluC][omeA][fluA][omeC][fluA][omeG][omeUs][omeU] |  |
| 8 | CTNNB1 | Passenger | 15 | [6amiL][iB][omeC][omeU][clickG][omeU][omeU][fluG][fluG][fluA][omeU][omeU][fluG][fluA][omeU][omeU][omeC][fluG][clickAllfluAifluAflomeUsilomeuifiB] | 58 |
|   | CTNNB1 | Guide | 16 | [omeUs][fluUs][omeUs][fluC][omeG][fluA][omeA][fluU][omeC][fluA][omeA][fluU][omeC][fluC][clickA][fluA][omeC][fluA][omeG][omeUs][omeU] |  |

As used herein, ome = 2' methoxy; flu = 2' fluoro; click = 2' propagyl; iB = inverted abasic; "s" subscript = phosphorothioate; and r = 2' ribo; 6amil = n-hexylamino.

In Vitro and in Vivo Activity Data

Using the method as described later, the in vivo and in vitro data are presented in Table 4.

Note that the siRNA depictions below are for illustrative purposes. Specific sequence information can be found in Table 3.

TABLE 4

In vitro and In Vivo Activity

| Entry | Compound | Starting siRNA sequence code | Dose (mpk) Route of Administration | In vivo % KD (72 h) | IC50 w/LF2K in HEK-Luc [pM] | ASGR binding IC50 nM |
|---|---|---|---|---|---|---|
| 1 | 10a-1 | 51 | 5, 15 SC | 33.6; 69.5 | 15.44 | 36.7 |
| 2 | 10b-1 | 54 | SC 5, 15; IV 15 | 42, 49, 13 | 19.64 | 18.1 |
| 3 | 10-2 | 56 | 5, 50 SC | 40, 56 (24 h) | 23.4 |  |
| 4 | 10-3 | 57 | 1, 2.5, 5 SC | 20, 45, 60 | 52 (HepG2) |  |
| 5 | 17a-1 | 51 | 5 SC; 15 IV | 11, 5 | 20.16 | 49.1 |
| 6 | 17b-1 | 54 | 5 SC; 15 IV | 12, 22 | 43.96 | 33.3 |
| 7 | 19-1 | 52 | 5; 15 SC | 32; 68 | 24.04 | 3.6 |
| 8 | 29 | 53 | 15 SC; 15 IV | 43, 0 | 17.83 | 22 |
| 9 | 36 | 58 | 1, 2.5, 5 SC | 16, 43, 56 |  |  |
| 10 | 37 | 58 | 1, 2.5, 5 SC | 16, 32, 40 |  |  |
| 11 | 38 | 51 | 5 SC, 15 IV | 36, 33 | 71 | 17 |
| 12 | 39 | 51 | 5 SC, 15 IV | 19, 31 | 46.8 | 44 |
| 13 | 40 | 51 | 5, 15 SC | 33, 62 | 76.8 | 77 |
| 14 | 41 | 51 | 5, 15 SC | 28, 74 | 98.6 | 134 |
| 15 | 42 | 51 | 5, 15 SC | 19, 73 | 309.7 | 135 |
| 16 | 43 | 51 | 5, 15 SC | 8, 73 | 64.8 | 45 |
| 17 | 44 | 51 | 5, 15 SC | 31, 73 | 67.1 | 66 |
| 18 | 45 | 51 | 5 SC, 15 IV | 20, 4 | 73.4 | 11 |
| 19 | 48a-1 | 51 | 5, 15 SC | 10.24; 59.93 | 23.43 |  |
| 20 | 48b-1 | 53 | 5, 15 SC | 19.87; 42.08 | 57.96 |  |
| 21 | 51 | 55 | 5; 15 | 40; 45 | 1838.47 | 94.8 |

Examples 1-2
Synthesis of TetraGalNAc Ligand Compounds 9 and 10
The following Scheme 1 was used to prepare TetraGalNAc Compounds 9 and 10.
SCHEME 1
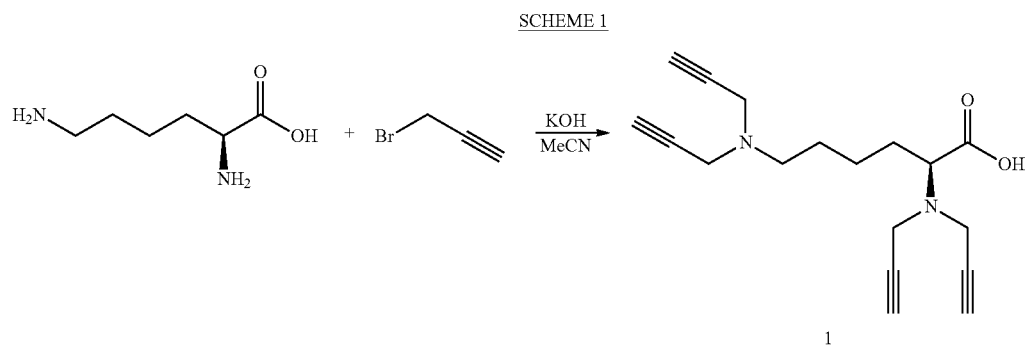
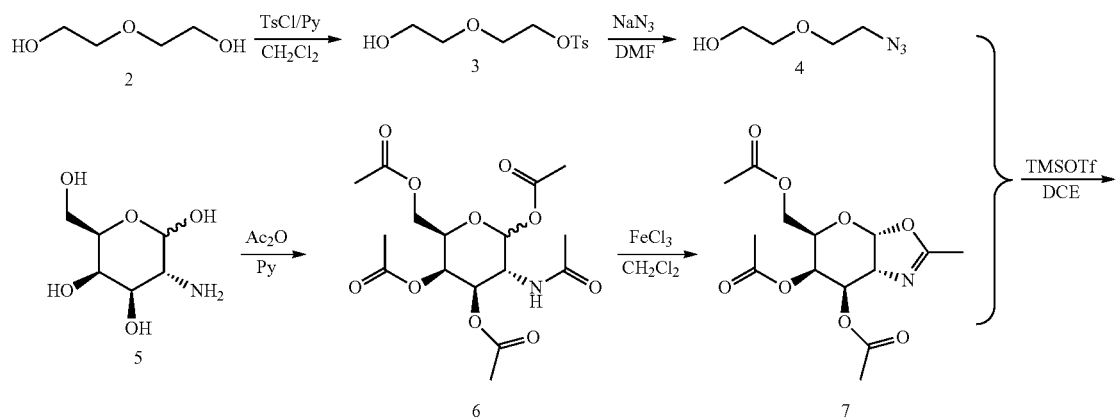
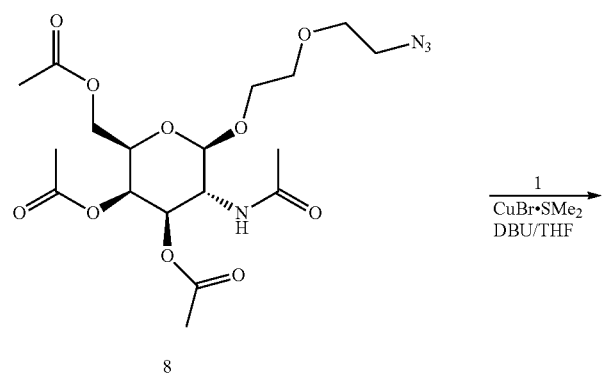

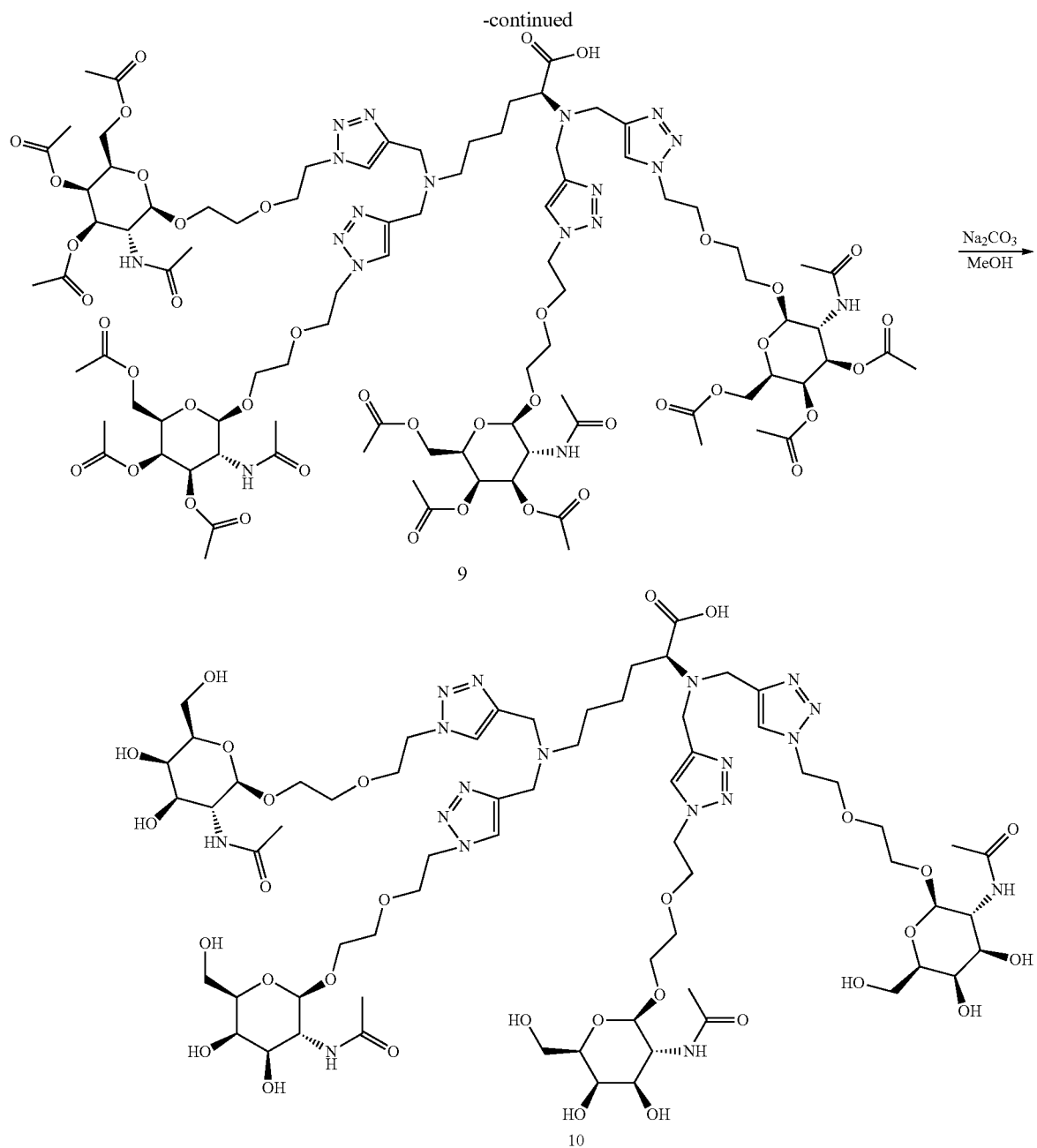

9

10

Synthesis of (2S)-2,6-bis[bis (prop-2-yn-1-yl) amino]hexanoic acid (Compound 1)

Into a 2000-mL 3-necked round-bottom flask purged and maintained with an inert atmosphere of nitrogen was placed a solution of (2S)-2,6-diaminohexanoic acid (50 g, 342.03 mmol, 1.00 equiv) in acetonitrile (1000 mL) and heated to 50° C. To this was added potassium hydroxide (22.6 g, 0.4025 mol, 1.00 equiv, 85%). The resulting solution was stirred for 30 min. Then 3-bromoprop-1-yne (29.5 mL, 1.00 equiv) was added. The resulting solution was stirred for 1 hour at 50° C. additional potassium hydroxide (22.6 g, 0.4025 mol, 1.00 equiv) was added to the solution and stirred for 30 min at 50° C. To this was added 3-bromoprop-1-yne (29.5 mL, 1.00 equiv). The resulting solution was stirred for 1 hour. To this was added potassium hydroxide (22.6 g, 0.4025 mol, 1.00 equiv) again. The resulting solution was stirred for 30 min at 50° C., followed by addition of more 3-bromoprop-1-yne (29.5 mL, 1.00 equiv). The resulting solution was stirred for 1 hour. To this was added potassium hydroxide (22.6 g, 0.4025 mol, 1.00 equiv). The resulting solution was stirred for 30 min. To this was added 3-bromoprop-1-yne (29.5 mL, 1.00 equiv). The resulting solution was stirred for 3 hours. The reaction mixture was cooled to 25° C. with a water/ice bath. The solid was filtered out. The filtrate was adjusted to pH 4 with HCl (6M). The solid was filtered out. The filtrate was concentrated under vacuum. The residue was applied onto a silica gel column and eluted with dichloromethane/methanol (100:1-25:1). This resulted in (2S)-2, 6-bis[bis (prop-2-yn-1-yl)amino] hexanoic acid (Compound 1) as a light yellow oil.

MS(ES, m/z): 297.2, [M-H]−¹HNMR(CDCl₃, 500 MHz, ppm): 3.62 (d, J=2.0 Hz, 4H), 3.52-3.49 (m, 1H), 3.50 (d, J=2.4 Hz, 4H), 2.62 (t, J=7.1 Hz, 2H), 2.30 (t, J=2.4 Hz, 2H), 2.27 (t, J=2.4 Hz, 2H),1.88-1.79 (m, 2H), 1.60-1.53 (m, 2H), 1.52-1.43 (m, 2H).

Synthesis of 2-(2-hydroxyethoxy)ethyl 4-methylbenzenesulfonate (Compound 3)

Into a 2000-mL 3-necked round-bottom flask purged and maintained with an inert atmosphere of nitrogen was placed a solution of 2-(2-hydroxyethoxy)ethan-1-ol (Compound 2, 42.4 g, 399.55 mmol, 1.00 equiv) in dichloromethane (1000 mL) and triethylamine (27.9 g, 275.72 mmol, 0.25 equiv). To the above was added p-toluenesulfonyl chloride (19.1 g, 100.18 mmol, 0.50 equiv). After stirred for 1 h at 25° C., the resulting mixture was washed with 1×500 mL of aq. potassium hydrosulfate (1M) and 1×500 mL of aq. sodium bicarbonate (5%) respectively. The organic layer was dried over anhydrous sodium sulfate and concentrated under vacuum. The residue was applied onto a silica gel column and eluted with dichloromethane/methanol (100:1). This resulted in 2-(2-hydroxyethoxy)ethyl 4-methylbenzenesulfonate (Compound 3) as a colorless oil.

Synthesis of 2-(2-azidoethoxy)ethan-1-ol (Compound 4)

Into a 500-mL round-bottom flask purged and maintained with an inert atmosphere of nitrogen was placed a solution of 2-(2-[[(4-2-(2-hydroxyethoxy)ethyl 4-methylbenzenesulfonate (Compound 3, 50 g, 192.08 mmol, 1.00 equiv) in N,N-dimethylformamide (250 mL). This was followed by the addition of sodium azide (18.79 g, 289.03 mmol, 1.50 equiv) at 25° C. The resulting solution was stirred for 5 h at 100° C. in an oil bath. The reaction mixture was cooled and filtered. The filtrate was concentrated under vacuum. The residual solution was diluted with 1000 mL of dichloromethane and washed with 1×500 mL of water. The organic layer was dried over anhydrous sodium sulfate and concentrated under vacuum. The residue was applied onto a silica gel column and eluted with dichloromethane/methanol (80:1). This resulted in 2-(2-azidoethoxy)ethan-1-ol (Compound 4) as a colorless oil.

¹HNMR (CDCl₃, 400 MHz, ppm): 3.42-3.45(t, J=4.8Hz, 2H), 3.63-3.65(t, J=4.8Hz, 2H), 3.71-3.74(t, J=4.8Hz, 2H), 3.71-3.79(m, 2H).

Synthesis of (3R,4R,5R,6R)-3-acetamido-6-(acetoxymethyl)tetrahydro-2H-pyran-2,4,5-triyl triacetate (Compound 6)

Into a 2000-mL 3-necked round-bottom flask purged and maintained with an inert atmosphere of nitrogen was placed a solution of (3R,4R,5R,6R)-3-amino-6-(hydroxymethyl)tetrahydro-2H-pyran-2,4,5-triol hydrochloride (Compound 5, 120 g, 556.50 mmol, 1.00 equiv) in pyridine (1200 mL). This was followed by the addition of acetic anhydride (341.6 g, 3.35 mol, 6.00 equiv) dropwise with stirring at 0° C. The resulting solution was stirred overnight at 25° C. The reaction was then quenched by the addition of 8000 mL of water/ice. The solid was collected by filtration. This resulted in (3R,4R,5R,6R)-3-acetamido-6-(acetoxymethyl)tetrahydro-2H-pyran-2,4,5-triyltriacetate (Compound 6) as a white solid.

Synthesis of (3aR,5R,6R,7R,7aR)-5-(acetoxymethyl)-2-methyl-5,6,7,7a-tetrahydro-3aH-pyrano[3,2-d]oxazole-6,7-diyl diacetate (Compound 7)

Into a 2000-mL round-bottom flask purged and maintained with an inert atmosphere of nitrogen was placed a solution of (3R,4R,5R,6R)-3-acetamido-6-(acetoxymethyl) tetrahydro-2H-pyran-2,4,5-triyl triacetate (Compound 6, 30 g, 77.05 mmol, 1.00 equiv) in dichloromethane (1500 mL), then added iron (III) chloride (30 g, 184.95 mmol, 2.40 equiv). The resulting mixture was stirred for 2 h at 25° C. The reaction was then quenched by the addition of 1000 mL of water/ice. The organic layer was washed with 1×1000 mL of sodium aq. bicarbonate and 1×1000 mL of water, dried over anhydrous sodium sulfate and concentrated under vacuum. This resulted in (3aR,5R,6R,7R,7aR)-5-(acetoxymethyl)-2-methyl-5,6,7,7a-tetrahydro-3aH-pyrano[3,2-d]oxazole-6,7-diyl diacetate (Compound 7) as yellow oil.

¹HNMR(CDCl₃, 300 MHz, ppm): 2.03(s, 9H), 2.12(s, 3H), 3.97-4.27(m, 4H), 4.90-4.93(m, J =3.3Hz, 1H), 5.45-5.47(t, J=3.0Hz, 1H), 5.98-6.00(d, J=6.6Hz, 1H).

Synthesis of (2R,3R,4R,5R,6R)-5-acetamido-2-(acetoxymethyl)-6-[2-(2-azidoethoxy)ethoxy]tetrahydro-2H-pyran-3,4-diyl diacetate (Compound 8)

Into a 500-mL round-bottom flask purged and maintained with an inert atmosphere of nitrogen was placed a solution of (3aR,5R,6R,7R,7aR)-5-(acetoxymethyl)-2-methyl-5,6,7,7a-tetrahydro-3aH-pyrano[3,2-d]oxazole-6,7-diyl diacetate (Compound 7, 40 g, 121.47 mmol, 1.00 equiv) in 1,2-dichloroethane (200 mL), 2-(2-azidoethoxy)ethan-1-ol (Compound 4, 23.89 g, 182.18 mmol, 1.50 equiv). To the above several 4A zeolite was added. The resulting mixture was stirred for 1 h at 25° C. Then trimethylsilyl trifluoromethanesulfonate (10.8 mL, 0.50 equiv) was added. After stirred overnight at 25° C., the reaction mixture was diluted with 500 mL of dichloromethane and washed with 1×500 mL of water, 1×500 ml, of aq. sodium bicarbonate and 1×500 mL of water. The organic layer was dried over anhydrous sodium sulfate and concentrated under vacuum. The residue was applied onto a silica gel column and eluted with dichloromethane/methanol (100:1). This resulted in (2R,3R,4R,5R,6R)-5-acetamido-2-(acetoxymethyl)-6-[2-(2-azidoethoxy)ethoxy]tetrahydro-2H-pyran-3,4-diyl diacetate (Compound 8) as a colorless oil.

MS(m/z): 461.1, [M+H]⁺

¹HNMR(CDCl₃, 500 MHz, ppm) 5.78 (d, J=8.90 Hz, 1H), 5.36 (d, J=2.9 Hz, 1H), 5.22 (dd, J=11.2, 3.6 Hz, 1H), 4.77 (d, J=8.3 Hz, 1H), 4.19-4.12 (m, 2H), 4.11-4.05 (m, 1H), 3.98-3.92 (m, 2H), 3.82-3.78 (m, 1H), 3.71-3.63 (m, 4H), 3.49-3.38 (m, 2H), 2.16 (s, 3H), 2.05 (s, 3H), 2.01 (s, 3H), 1.97 (s, 3H).

Synthesis of (S)-2,6-bis(bis((1-(2-(2-(((2R,3R,4R, 5R,6R)-3-acetamido-4,5-diacetoxy-6-(acetoxymethyl)tetrahydro-2H-pyran-2-yl)oxy)ethoxy)ethyl)-1H-1,2,3-triazol-4-yl)methyl)amino)hexanoic acid (Compound 9, tetraGalNAc Acetate) (Ex. 1)

Into a 250-mL round bottom flask purged and maintained with an inert atmosphere of nitrogen was charged (2S)-2,6-bis [bis(prop-2-yn-1-yl)amino]hexanoic acid (Compound 1, 1.0 g, 1.0 equiv), (2R,3R,4R,5R,6R)-5-acetamido-2-(acetoxymethyl)-6-[2-(2-azidoethoxy)ethoxy]tetrahydro-2H-pyran-3,4-diyl diacetate (Compound 8, 9.26 g, 6.0 equiv), anhydrous THF 50 mL, CuBr.SMe$_2$ (0.138 g, 0.20 equiv), and anhydrous DBU (1.5 ml, 3.0 equiv) in respective order. The resulting solution was stirred for 16 h at room temperature, quenched with acetic acid (0.75 mL, 4.0 equiv), treated with MP-TMT resin (Part No: 801472, from Biotage) (9 g), aged at room temperature for 16 h, filtered, and concentrated the filtrate to a foam solid. The solid was then dissolved in CH$_2$Cl$_2$ (140 mL), and washed with AcOH/NaCl solution (140 mL). The AcOH/NaCl solution was prepared with 1 mL AcOH and 100 mL 20% NaCl solution. The bottom organic layer was concentrated, and purified on a SiO$_2$ column (220 g), eluting with CH$_2$Cl$_2$/MeOH. This resulted in (S)-2,6-bis(bis((1-(2-(2-(((2R,3R,4R,5R,6R)-3-acetamido-4,5-diacetoxy-6-(acetoxymethy)tetrahydro-2H-pyran-2-yl)oxy)ethoxy)ethyl)-1H-1,2,3-triazol-4-yl)methyl)amino)hexanoic acid (Compound 9) as a white solid.

MS(m/z): 2139.5, [M+H]$^+$

Synthesis of (S)-2,6-bis(bis((1-(2-(2-(((2R,3R,4R,5R,6R)-3-acetamido-4,5-dihydroxy-6-(hydroxymethyl)tetrahydro-2H-pyran-2-yl)oxy)ethoxy)ethyl)-1H-1,2,3-triazol-4-yl)methyl)amino)hexanoic acid (Compound 10, TetraGalNAc) (Ex. 2)

Into a 250-mL round-bottom flask purged and maintained with an inert atmosphere of nitrogen was charged (S)-2,6-bis(bis((1-(2-(2-4(2R,3R,4R,5R,6R)-3-acetamido-4,5-diacetoxy-6-(acetoxymethyl)tetrahydro-2H-pyran-2-yl)oxy)ethoxy)ethyl)-1H-1,2,3-triazol-4-yl)methyl)amino)hexanoic acid (Compound 9, 6.9 g, 1.0 equiv), Na$_2$CO$_3$ (6.83 g, 20 eq), water (56 mL), and MeOH (32mL) in respective order. The reaction was aged at room temperature for 16h, concentrated to residue, redissolved in water (50mL), and purified on Combiflash C18 gold reverse column (415 g), eluting with water/MeCN. After concentration under vacuum, the product was dissolved in minimum amount of water, and lyophilized to obtain (S)-2,6-bis(bis((1-(2-(2-(((2R,3R,4R,5R,6R)-3-acetamido-4,5-dihydroxy-6-(hydroxymethyl)tetrahydro-2H-pyran-2-yl)oxy)ethoxy)ethyl)-1H-1,2,3-triazol-4-yl)methyl)amino)hexanoic acid (Compound 10) as a white solid.

MS(m/z): 1657 [M+Na]$^+$ $^1$HNMR(D$_2$O, 500 MHz, ppm): 8.05 (s, 2H), 7.91 (s, 2H), 4.62 (t, J=5.0 Hz, 4H), 4.57 (t, J=5.0 Hz, 4H), 4.45-4.41 (d, J=8.6 Hz, 4H), 3.99-3.82 (m, 28H), 3.80-3.61 (m, 28H), 3.14 (t, J=7.1 Hz, 1H), 2.52 (broad s, 2H), 1.99 (s, 6H), 1.98 (s, 6H), 1.73 (m, 2H), 1.60 (m, 2H), 1.29 (m, 2H).

Examples 3-5

Synthesis of TetraGalNAc Ligand Compounds 17a, 17b and 17c

The following Scheme 2 was used to prepare TetraGalNAc Compounds 17a, 17b and 17c.

SCHEME 2

-continued
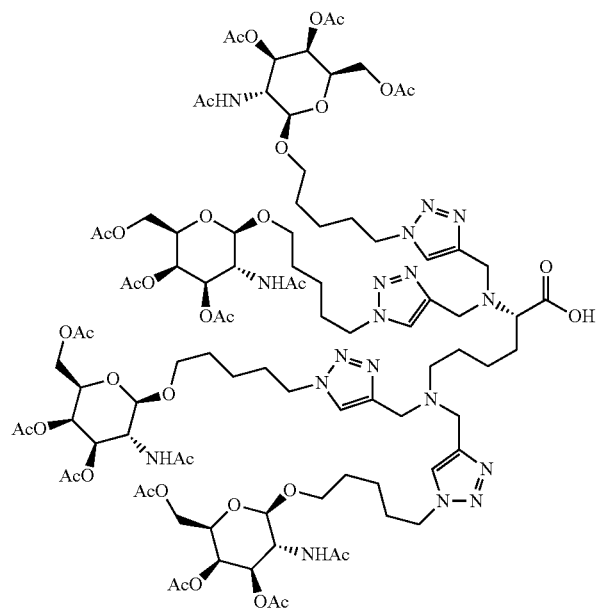
16
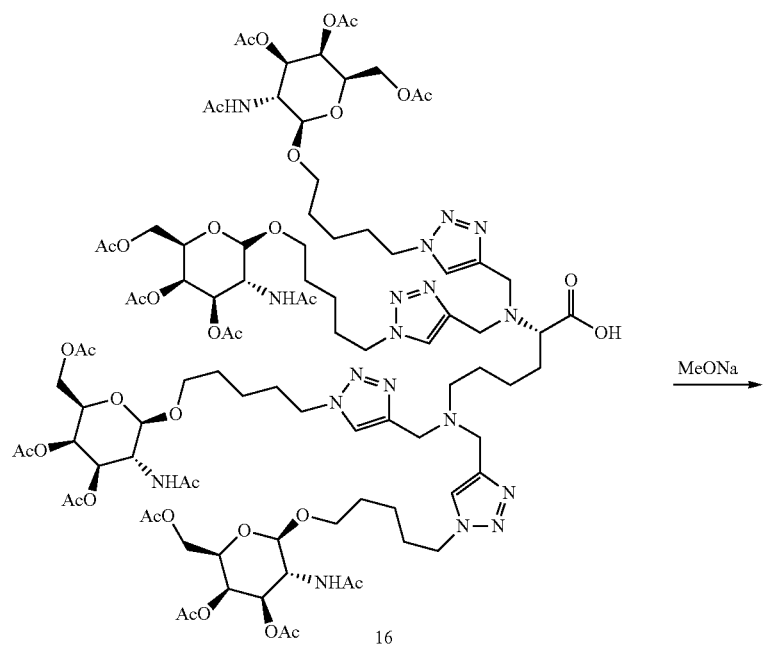
16
→ MeONa

-continued

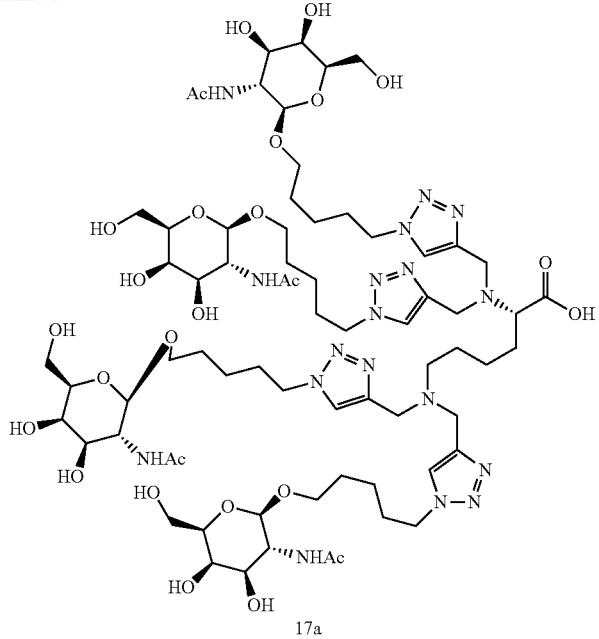

17a

Synthesis of Compound 13

To a solution of 5-chloro-1-pentanol (3.0 g, 24.47 mmol) Compound 11 in DMF (20 mL) was added sodium azide (1.909 g, 29.4 mmol) Compound 12. After being stirred at 60° C. for overnight, the reaction mixture was concentrated in vacu. The residue was purified by silica gel chromatography (EtOAc/Hexane 1:3), to give product Compound 13 as clear liquid. $^1$H NMR (500 MHz, CDCl$_3$) δ 3.62 (m, 2H), 3.25 (t, J=6.9 Hz, 2H), 1.63-1.53 (m, 4H), 1.45-1.40 (m, 2H).

Synthesis of Compound 15

Compound 13 (0.796 g, 6.16 mmol) and D-galactosamine pentaacetate (2.00 g, 5.14 mmol) Compound 14 were suspended in 20 mL DCM, followed by addition of trifluoromethanesulfonic acid (0.154 g, 1.027 mmol). The resulting mixture was brought to reflux for overnight. LC-MS indicated completed conversion of SM, the reaction mixture was diluted with EtOAc and washed with sodium bicarbonate and dried over sodium sulfate. Solvent was removed and the residue was purified by ISCO DCM/MeOH from 100/0 to 90/10 over 30 min to afford Compound 15 as a white solid. $^1$H NMR (500 MHz, CDCl$_3$) δ: 1.97 (6 H, s), 2.02 (6 H, s), 2.06 (6 H, s), 2.15 (6 H, s), 3.28 (6 H, t, J=6.89 Hz), 3.50 (3 H, dt, J=9.63, 6.66 Hz), 3.68 (1 H, q, J=5.98 Hz), 3.94-3.92 (7 H, m), 4.16-4.15 (5 H, m), 4.73 (2 H, d, J=8.34 Hz), 5.31 (2 H, dd, J=11.16, 3.48 Hz), 5.40-5.38 (5 H, m). Calculated mass: [M+H]$^+$:C$_{19}$H$_{31}$N$_4$O$_9$, 459.2; observed: 459.4.

Synthesis of Compound 16

Lys-alkyne Compound 1 (130 mg, 0.436 mmol) and GalNAc Azide 6 (999 mg, 2.178 mmol) were dissolved in THF (5 mL, degassed). Copper (I) bromide-dimethyl sulfide complex (17.91 mg, 0.087 mmol) was added in one portion to the reaction mixture and the THF solution was stirred for overnight at 40° C. The reaction color changed to blue/green, indicating Cu$^{2+}$, fresh sodium ascorbate 37 mg in 0.2 mL of water was added to reaction mixture and allowed to react overnight. The reaction was concentrated and purified by RP HPLC 5-60 MeCN(0.5% TFA)/Water(0.5% TFA) over 20 min. The collected fractions were combined and lyophilized to afford Compound 8 as a white solid. Calculated mass: [M+3H]$^{3+}$:C$_{94}$H$_{145}$N$_{18}$O$_{38}$, 2134.0, m/z=711.3; observed: 711.9.

Synthesis of Compound 17a (Ex. 3)

To protected TetraGalNAc Compound 8 (300 mg, 0.141 mmol) in DCM/MeOH=1/1 5 mL at 0° C. was added Sodium Methoxide (91 mg, 1.688 mmol). The reaction was stirred for 1 h and quenched by addition of 2 mL of water. Volatile solvent was removed, and the reaction mixture was purified by P4 bio gel with water and the collect fractions were combined and lyophilized to afford Compound 9 as a white solid. Calculated mass: [M+3H]$^{3+}$:C$_{70}$H$_{121}$N$_{18}$O$_{26}$, 1629.9, m/z=543.3; observed: 543.8; [M+2H]$^{2+}$: C$_{70}$H$_{120}$N$_{18}$O$_{26}$, 1628.9, m/z=814.5; observed: 814.9.

Synthesis of Compounds 17b and 17c (Ex. 4 and Ex. 5)

Syntheses of Compounds 17b and 17c which have the following structures were accomplished in a manner similar to that used for Compound 17a using the appropriate azide source.

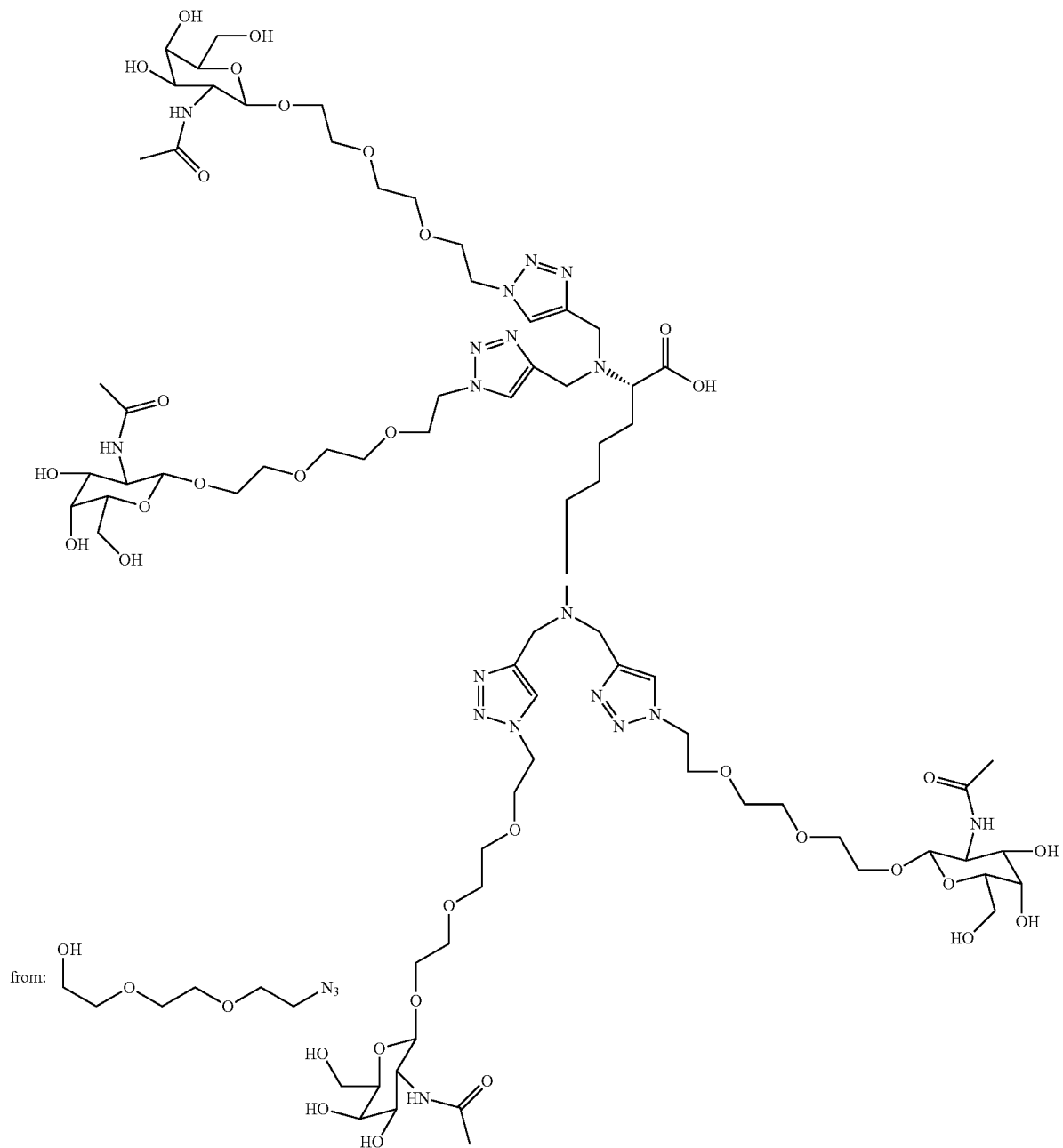

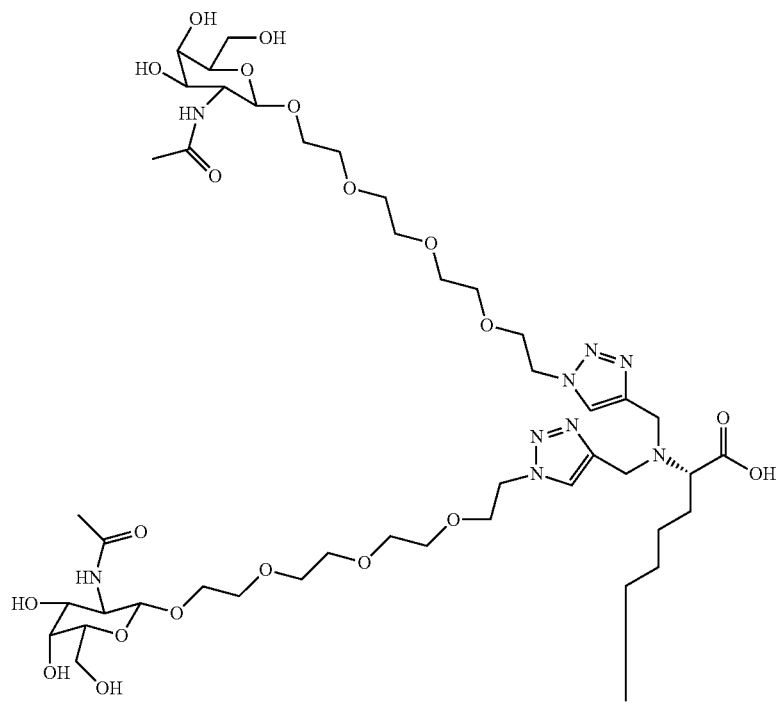
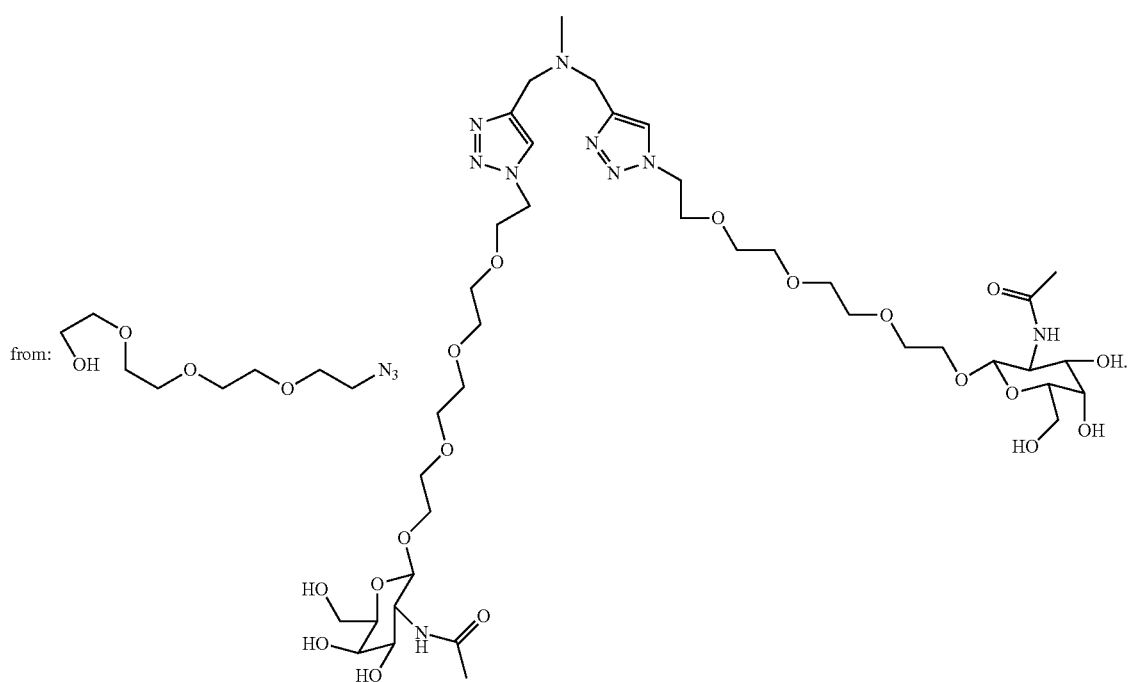
Example 6
Scheme of Conjugation of TetraGalNAc Ligands
Scheme 3 below shows a general scheme that can be used to prepare tetraGalNAc-siRNA conjugates.

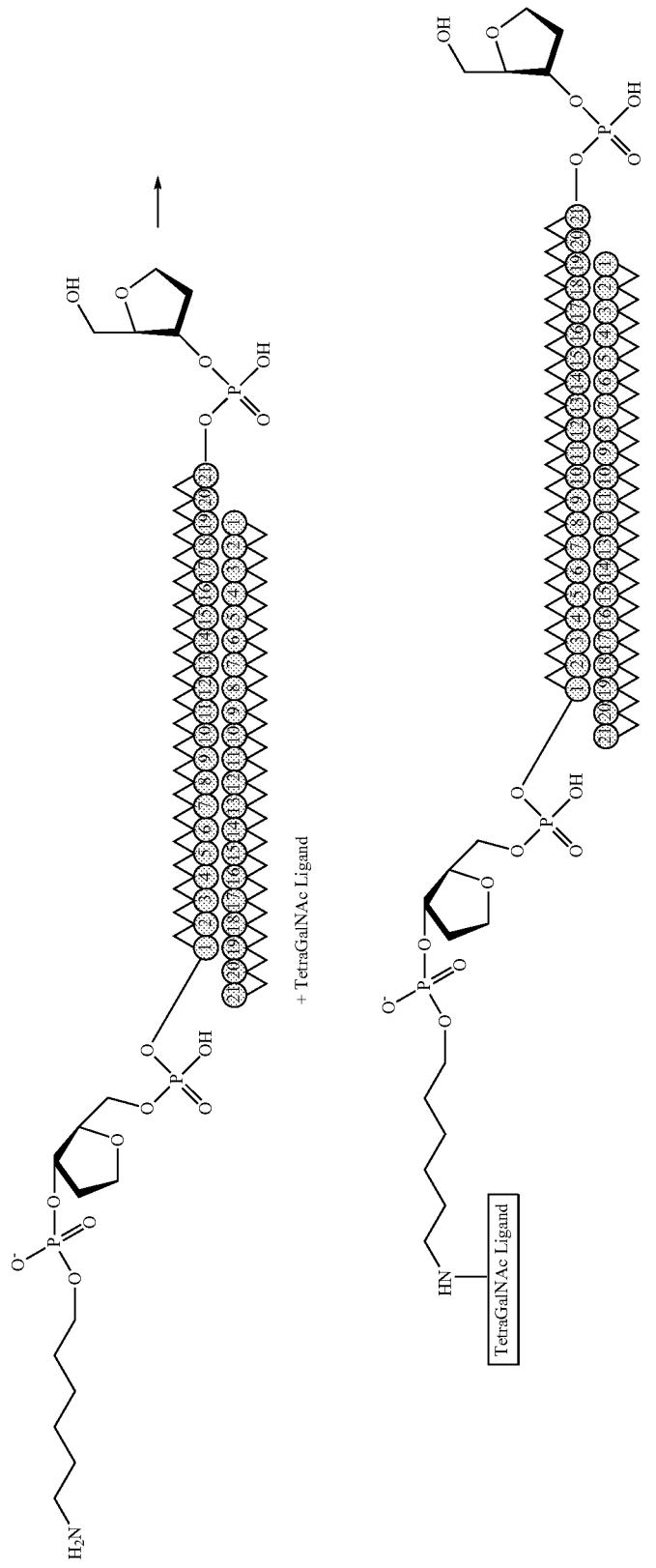

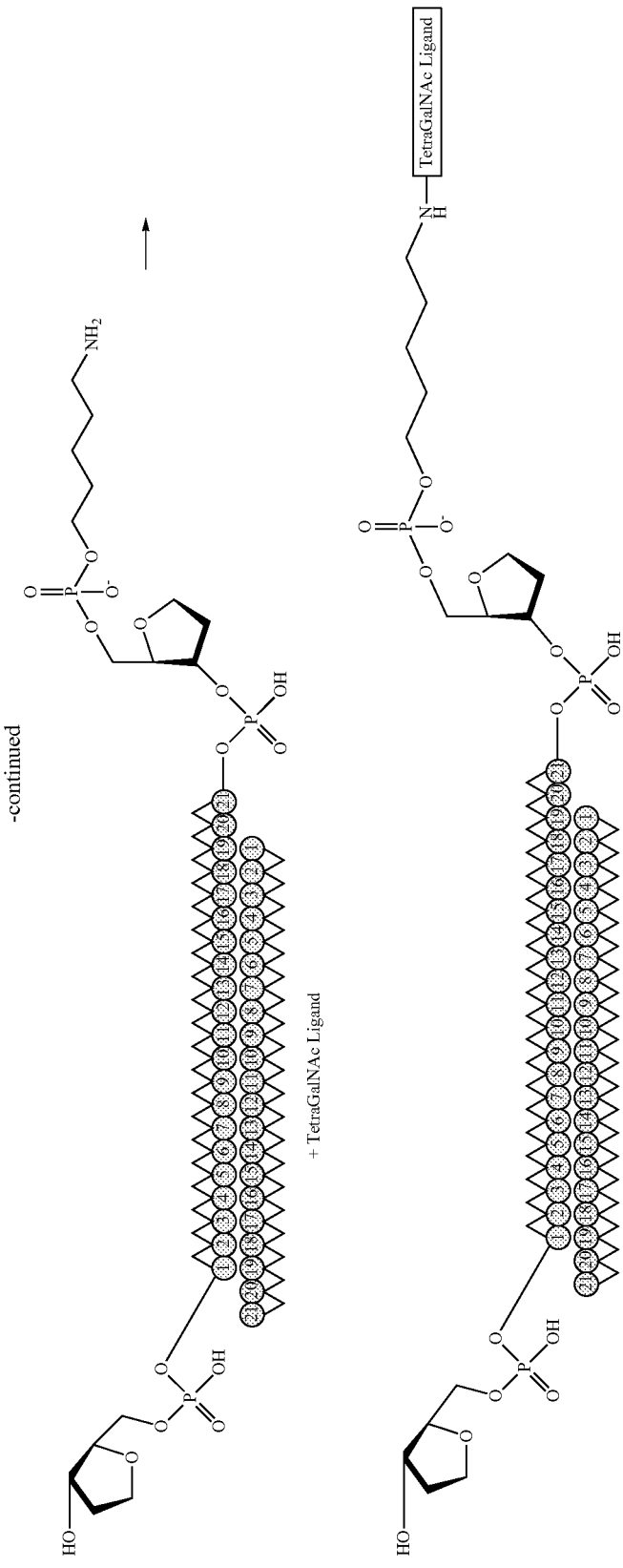

Using the general scheme 3, Conjugates 10-1, 10-2, 10-3, 10a-1, 17a-1, 17b-1, 17c-1 can be obtained. The coupling procedure can be performed on a preformed siRNA duplex or on a single strand followed by annealing. Alternatively, one can utilize the protocol outlined in *Bioconjug Chem.* 2011, 22, pp. 1723-8.

Example 7

Synthesis of TetraGalNAc-siRNA Conjugate 10-1 via TetraGalNAc Acetate Compound 9

To a solution of tetraGalNAc acetate (Compound 9, 58.7 mg, 0.027 mmol) in acetonitrile (1.5 ml) was added DIPEA (2.2 mg, 0.055 mmol) and HATU (10.44 mg, 0.027 mmol). The mixture was stirred at room temperature for 30 min, transferred into a solution of siRNA (51) (0.014 mmol) in water (1.5 ml) and acetonitrile (1.5 ml) via a syringe pump over 20 min, and stirred for 30 min before it was concentrated under vacuum down to 1.5 mL. Sodium carbonate (218 mg, 2.059 mmol) was then added, followed by MeOH (0.50 ml). The resulted solution was stirred at room temperature for 16h, concentrated, purified via dialysis, and lyophilized to yield tetraGalNAc-siRNA Conjugate 10-1.

Example 8

Synthesis of 3'5' Bis TetraGalNAc-siRNA Conjugate Single Strand 18

To a solution of tetraGalNAc acid Compound 10 (41.2 mg, 0.025 mmol) in DMSO (200 uL) was added HATU (9.6mg, 0.025 mmol) and DIPEA (17.6 uL, 0.126 mmol). The mixture was stirred at room temperature for 15 min, transferred into a solution of diamino-siRNA (18.8 mg, 2.52 umol) in water (40 uL) and DMSO (360 uL) and stirred for 30 min. The mixture was diluted with water (1.5 mL) and purified on a XBridge Prep Phenyl column (5 uM, 19×250 mm) using a gradient of 0-30% $CH_3CN$/water containing 100 mM TEAA. The fractions were concentrated via dialysis and lyophilized to yield Compound 18.

Example 9

Synthesis of 3'5' Bis TetraGalNAc-siRNA Duplex Conjugate 19-1

Scheme 4 below was used to prepare TetraGalNAc-siRNA Conjugate 19-1.

SCHEME 4
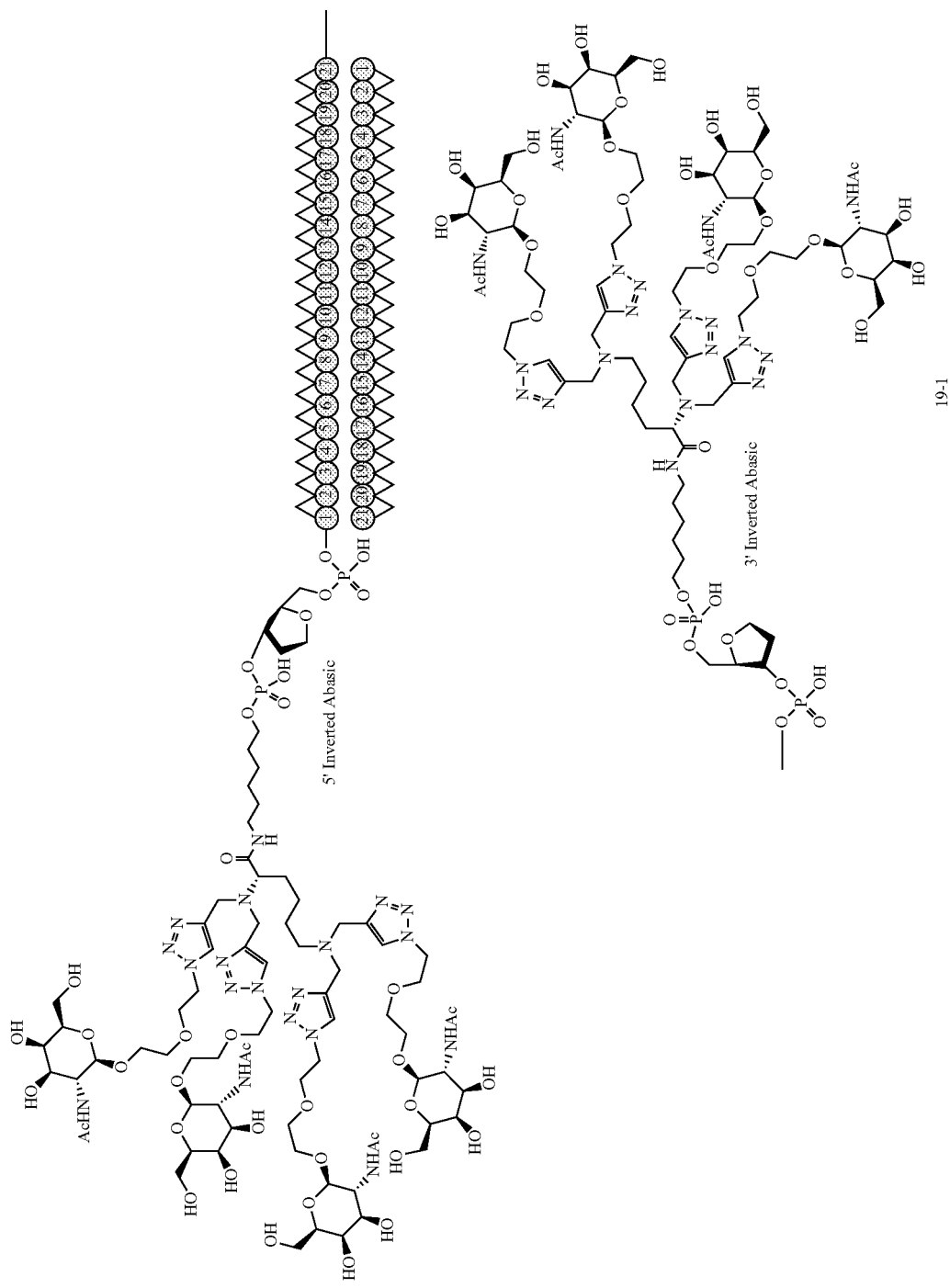

A solution of 3'5' bis tetraGalNAc-siRNA conjugate 18 (13.7 mg, 1.29 umol) in water (200 uL) was added to a solution of Guide siRNA (9.3 mg, 1.35 umol) dissolved in water (100 uL) and heated at 90 C for 1 minute. The resulting solution was cooled and lyophilized to yield duplex 19-1.
Example 10
Synthesis of TetraGalNAc Ligand Compound 24
The following Scheme 5 was used to prepare tetraGalNAc ligand Compound 24.
SCHEME 5
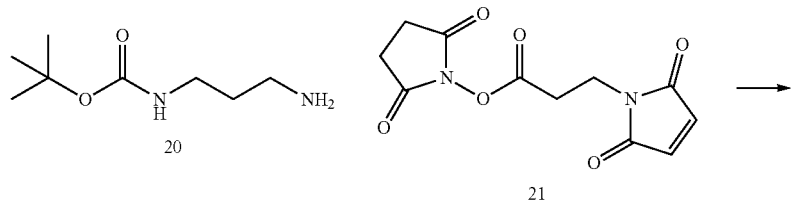
20
21
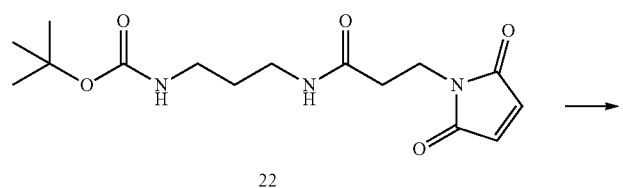
22
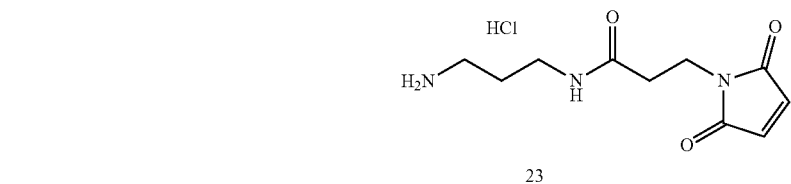
23
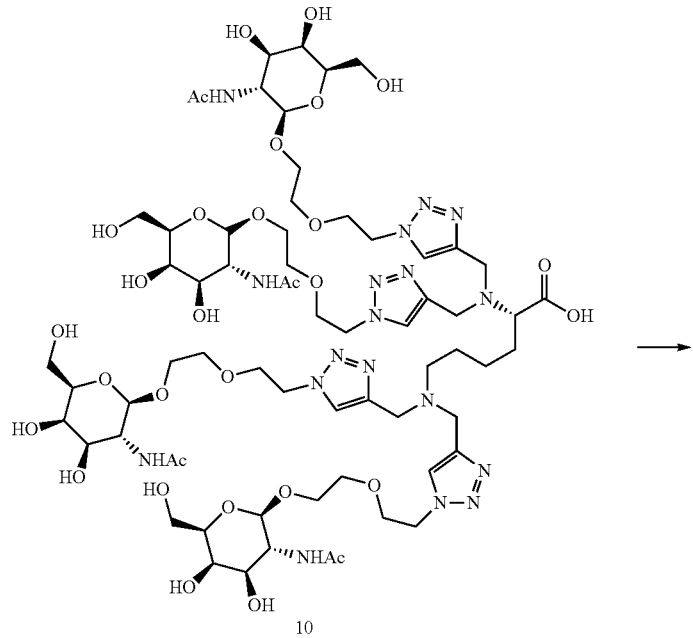
10

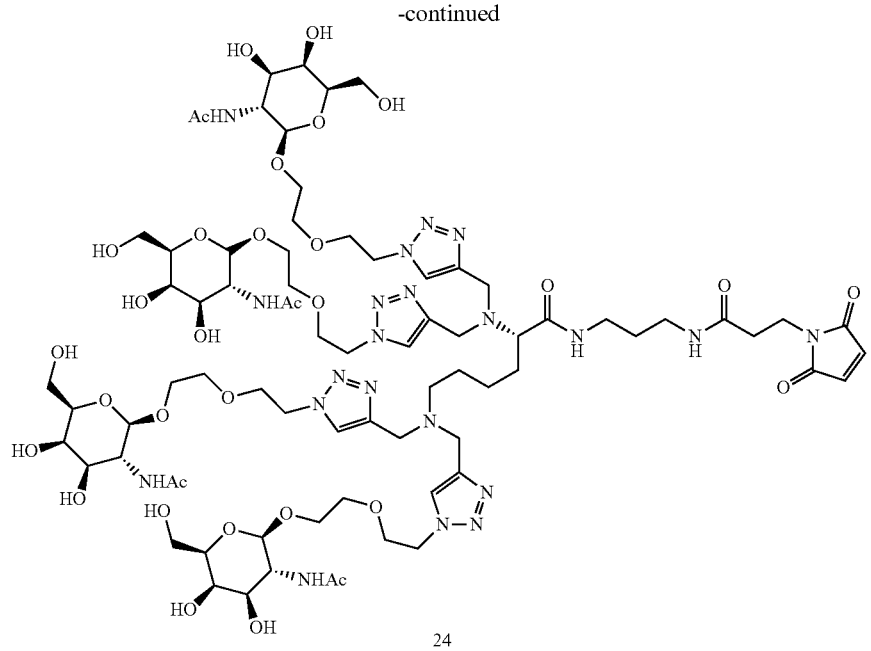

24

Synthesis of Compound 22

To a solution of N-BOC-1,3-diaminopropane (Compound 20, 115 mg, 0.660 mmol) in 1:1 $CH_2Cl_2/CH_3CN$ (1 mL) at 0° C. was added a solution of 3-maleimidopropionic acid N-hydroxysuccinimide ester (Compound 21, 185 mg, 0.695 mmol) dissolved in acetonitrile (4 mL) and $CH_2Cl_2$ (1 mL). The mixture was stirred for 1 h and concentrated in vacuo. The residue was purified by silica gel chromatography (0-5% MeOH/$CH_2Cl_2$) to give product Compound 22. Calculated mass: $[M+H]^+$:$C_{15}H_{24}N_3O_5$, 326.2; observed: 326.3.

Synthesis of Compound 23

To a solution of maleimide Compound 22 (56 mg, 0.172 mmol) in $CH_2Cl_2$ (1 ml) was added a solution of 4M HCl (1 ml, 4.00 mmol) in dioxane. The mixture was stirred for 1 h and concentrated in vacuo. The residue was azeotroped with $CH_2Cl_2$ (2×) and dried under vacuum to give product Compound 23. Calculated mass: $[M+H]^+$:$C_{10}H_{16}N_3O_3$, 226.1; observed: 226.3.

Synthesis of tetraGalNAc maleimide Compound 24 (Ex. 10)

To a solution of tetraGalNAc acid Compound 10 (100 mg, 0.061 mmol) in DMF (500 uL) was added HATU (34.9 mg, 0.092 mmol), $Et_3N$ (42.6 uL, 0.306 mmol) and N-(3-aminopropyl)-3-(2,5-dioxo-2,5-dihydro-1H-pyrrol-1-yl)propanamide hydrochloride (16.0 mg, 0.061 mmol). The mixture was stirred at room temperature for 1.5 h, acidified with TFA and purified by reverse phase 0-50% $CH_3CN$/water containing 0.1% TFA. The fractions were lyophilized to yield Compound 24. Calculated mass: $[M+2H]^{2+}$: $C_{76}H_{125}N_{21}O_{32}$, 1843.8, m/z=921.9; observed: 922.7.

Example 11

Synthesis of Compound 26

Scheme 6 below was used to prepare Compound 26.

SCHEME 6

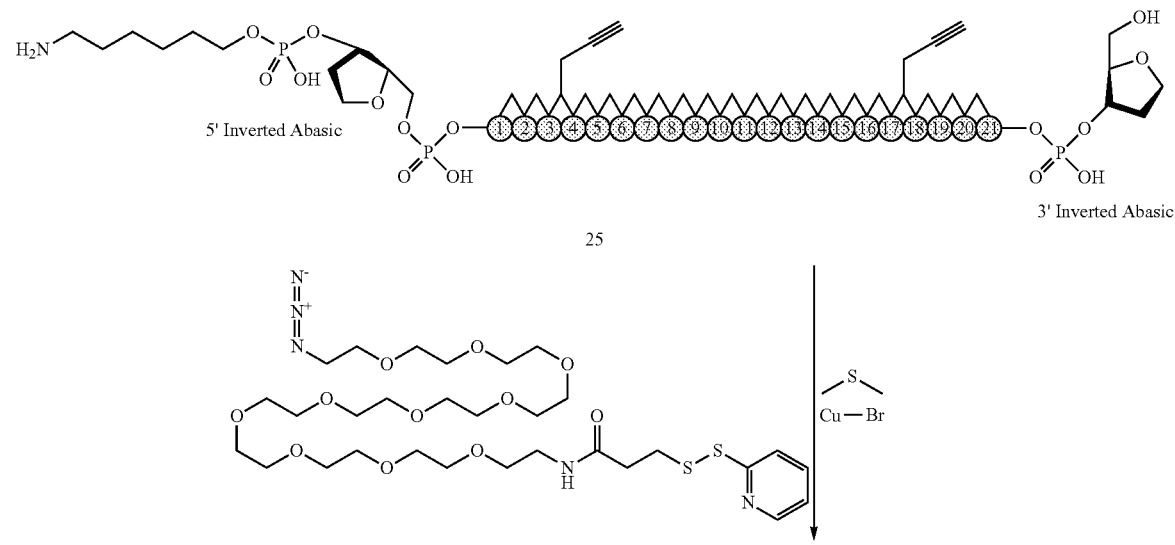

25

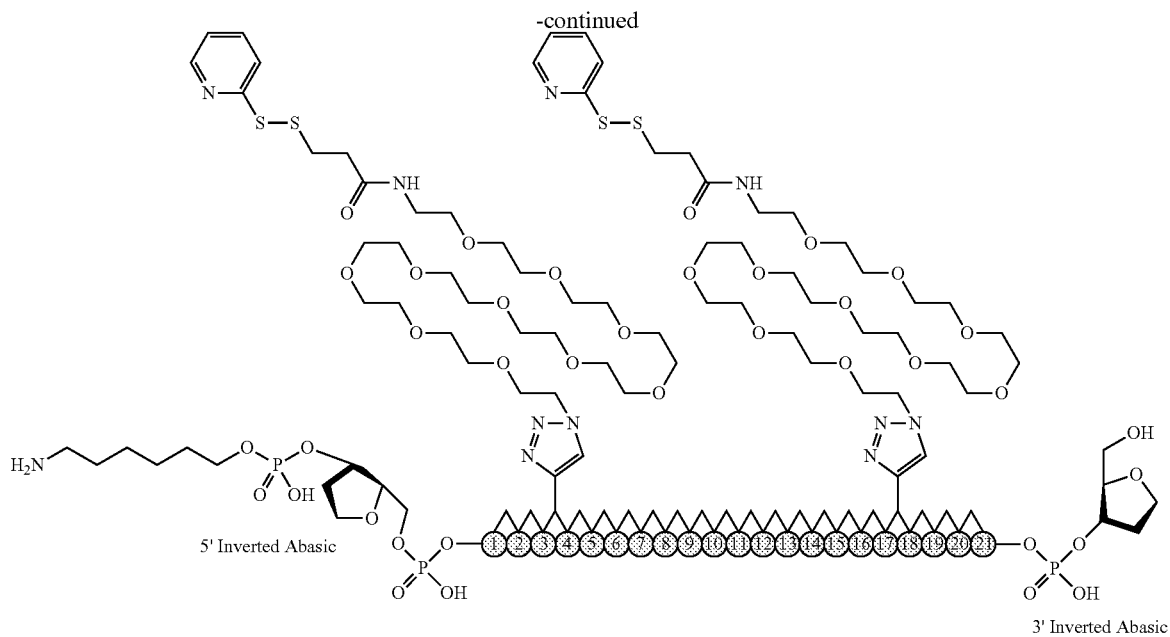

26

To a degassed solution of 2'-3,17 propargyl siRNA (RNA 25, 33 mg, 4.49 umol) and PEG9 SPDP azide (26 mg, 36 umol, prepared from commercial PEG-azide and pyridyl disulfide reagents) in 3:1 DMA/ water (1 mL) was added a degassed solution of Copper (I) Bromide-Dimethylsulfide Complex (1.8 mg, 9.0 umol). The mixture was stirred for 72 h at room temperature, diluted with water (2 mL), filtered using a 0.45 uM syringe filter and concentrated by dialysis. The concentrated mixture was purified on a XBridge Prep Phenyl column (5 uM, 19×250 mm) using a gradient of 0 — 50% $CH_3CN$/water containing 100 mM TEAA. The fractions were concentrated via dialysis and lyophilized to yield Compound 26.

Examples 12-13

Synthesis of Compounds 27 and 28

Scheme 7 below was used to prepare Compounds 27 and 28.

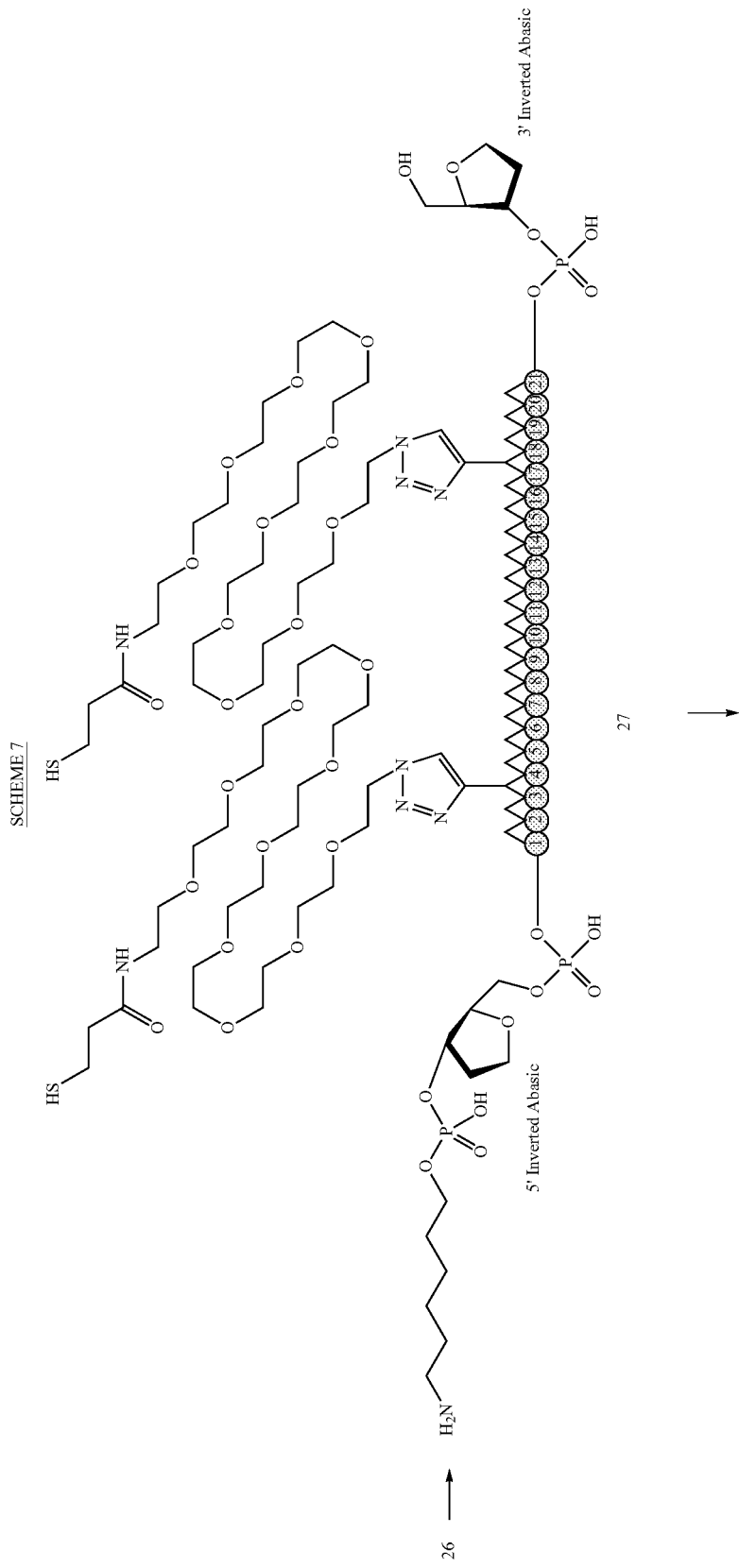

-continued
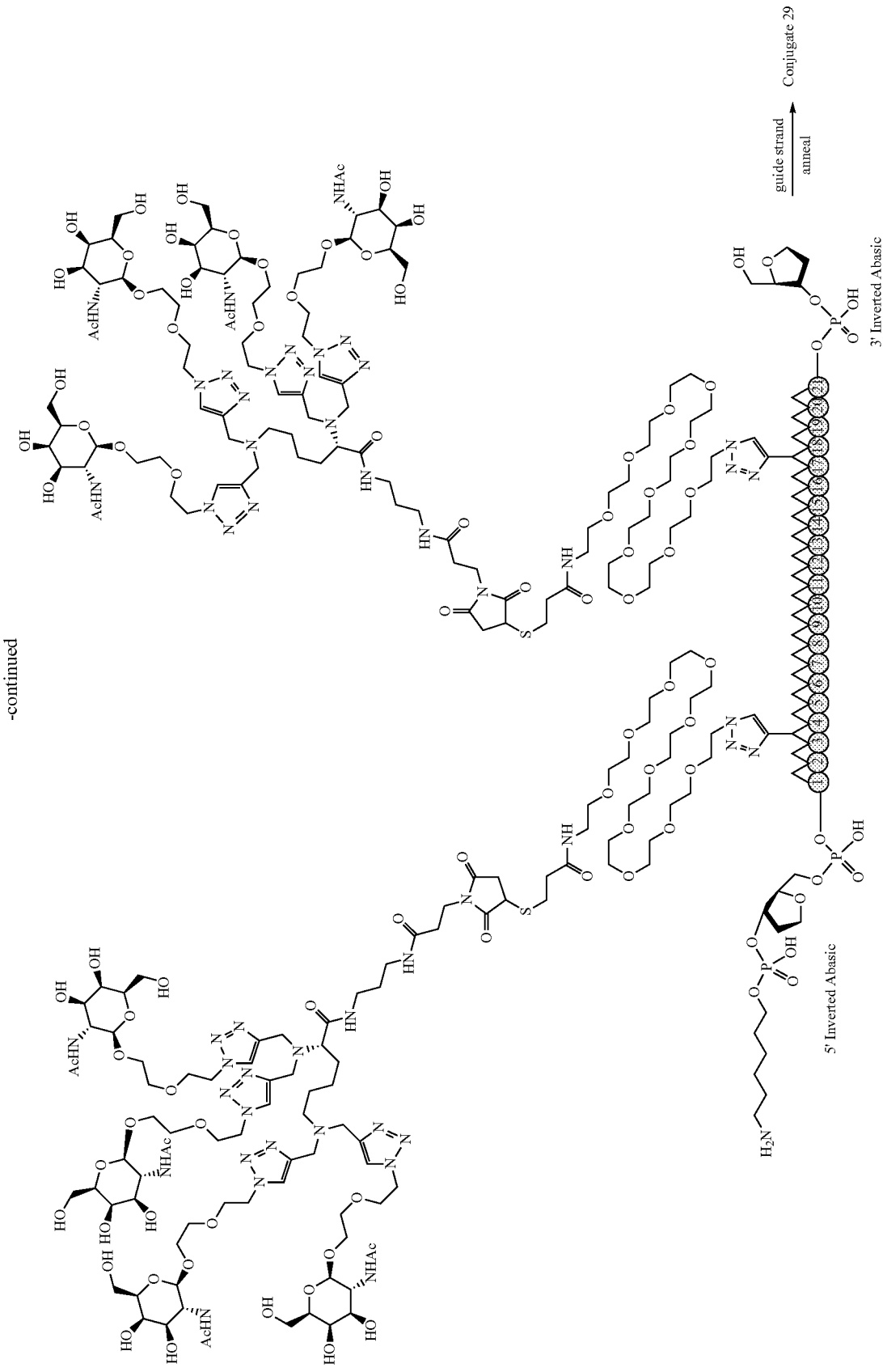

Synthesis of Compound 27 (Ex. 12)

To a solution of 2'-3,17 click PEG9 SPDP Conjugate 26 (13.2 mg, 1.50 µmol) in water (1 mL) was added a solution of TCEP hydrochloride (9.15 mg, 32.2 umol) dissolved in water (0.5 mL). The mixture was stirred at RT for 30 min then purified on a XBridge Prep Phenyl column (5 uM, 19×250 mm) using a gradient of 5-40% $CH_3CN$/water containing 100 mM TEAA. The fractions were concentrated via dialysis and lyophilized to yield Compound 27.

Synthesis of Compound 28 (Ex. 13)

To a solution of 2'-3,17-click PEG9SH 27 (3 mg, 0.35 µmol) in pH 6.0 acetate buffer (100 uL) was added a solution of tetra GalNAc maleimide (5.1 mg, 2.77 µmol) dissolved in pH 6.0 acetate buffer (100 uL). The mixture was stirred at room temperature for 30 min then purified on a XBridge Prep Phenyl column (5 uM, 19×250 mm) using a gradient of 5-40% $CH_3CN$/water containing 100 mM TEAA. The fractions were concentrated via dialysis and lyophilized to yield Compound 28.

Example 14

Synthesis of 2'-3,17 Bis TetraGalNAc-siRNA Duplex Conjugate 29

The procedure detailed for Conjugate 19 was used to duplex 28 to make Conjugate 29.

Example 15

Synthesis of TetraGalNAc Thiol Compound 31

Scheme 8 below was used to prepare Compound 31.

SCHEME 8

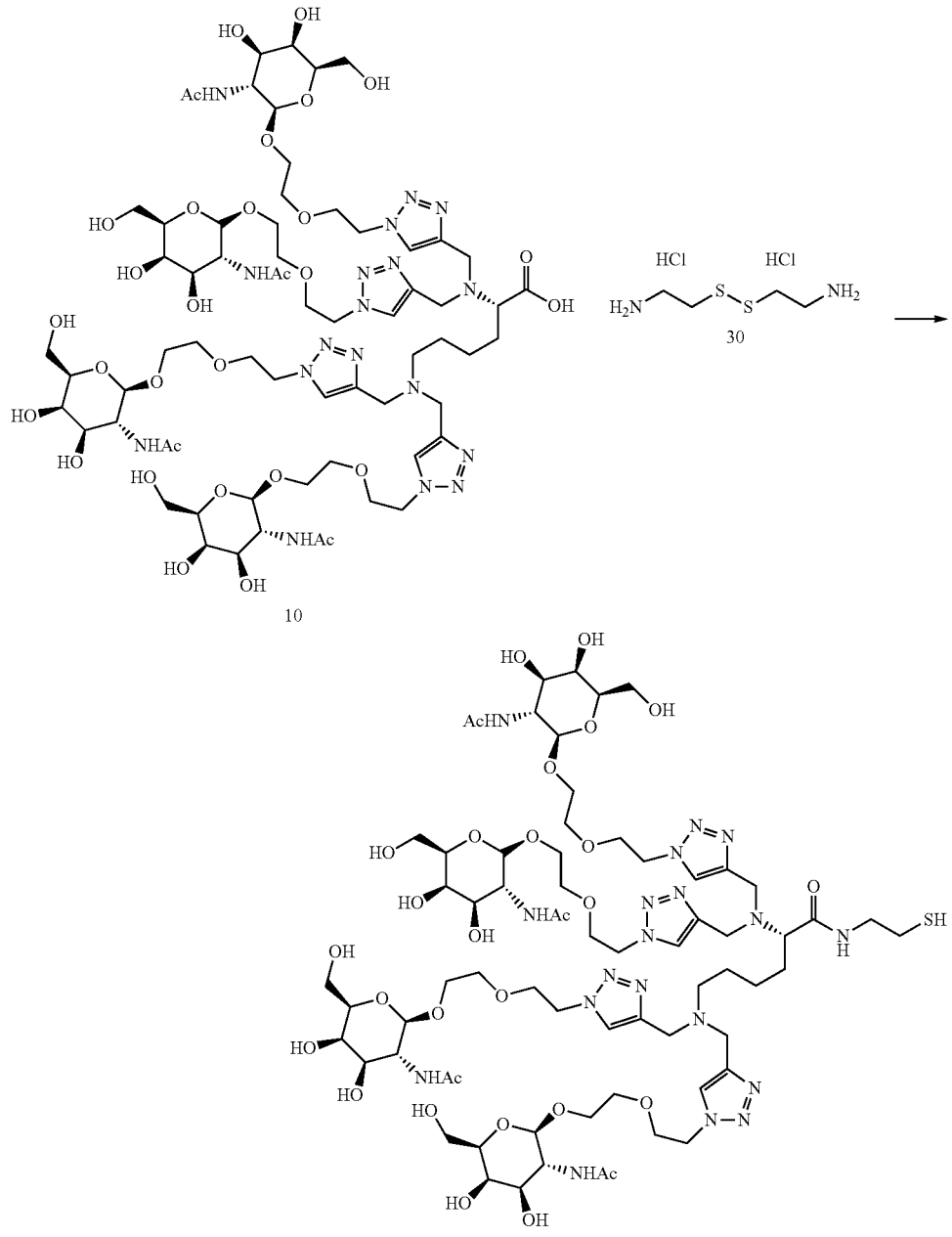

To a solution of tetraGalNAc acid Compound 10 (54 mg, 0.033 mmol) in N,N-dimethylacetamide (500 μl), was added cystamine dihydrochloride 30 (14.9 mg, 0.066 mmol), EDC (12.7 mg, 0.066 mmol), HOAT (10.2 mg, 0.066 mmol) and DIPEA (57.7 0.330 mmol). The mixture was stirred at room temperature for 18 h, then added a solution of DTT (50.9 mg, 0.330 mmol) in N,N-dimethylacetamide (100 μl). The mixture was stirred at room temperature for 0.5 h, acidified with TFA and purified by reverse phase 0-30% $CH_3CN$/water containing 0.1% TFA. The fractions were lyophilized to yield Compound 31. Calculated mass: $[M+2H]^{2+}$: $C_{68}H_{115}N_{19}O_{29}S$, 1695.8, m/z=847.9; observed: 848.0.

Examples 16-18

Synthesis of Conjugates 35-37

Scheme 9 below was used to prepare Conjugates 35-37.

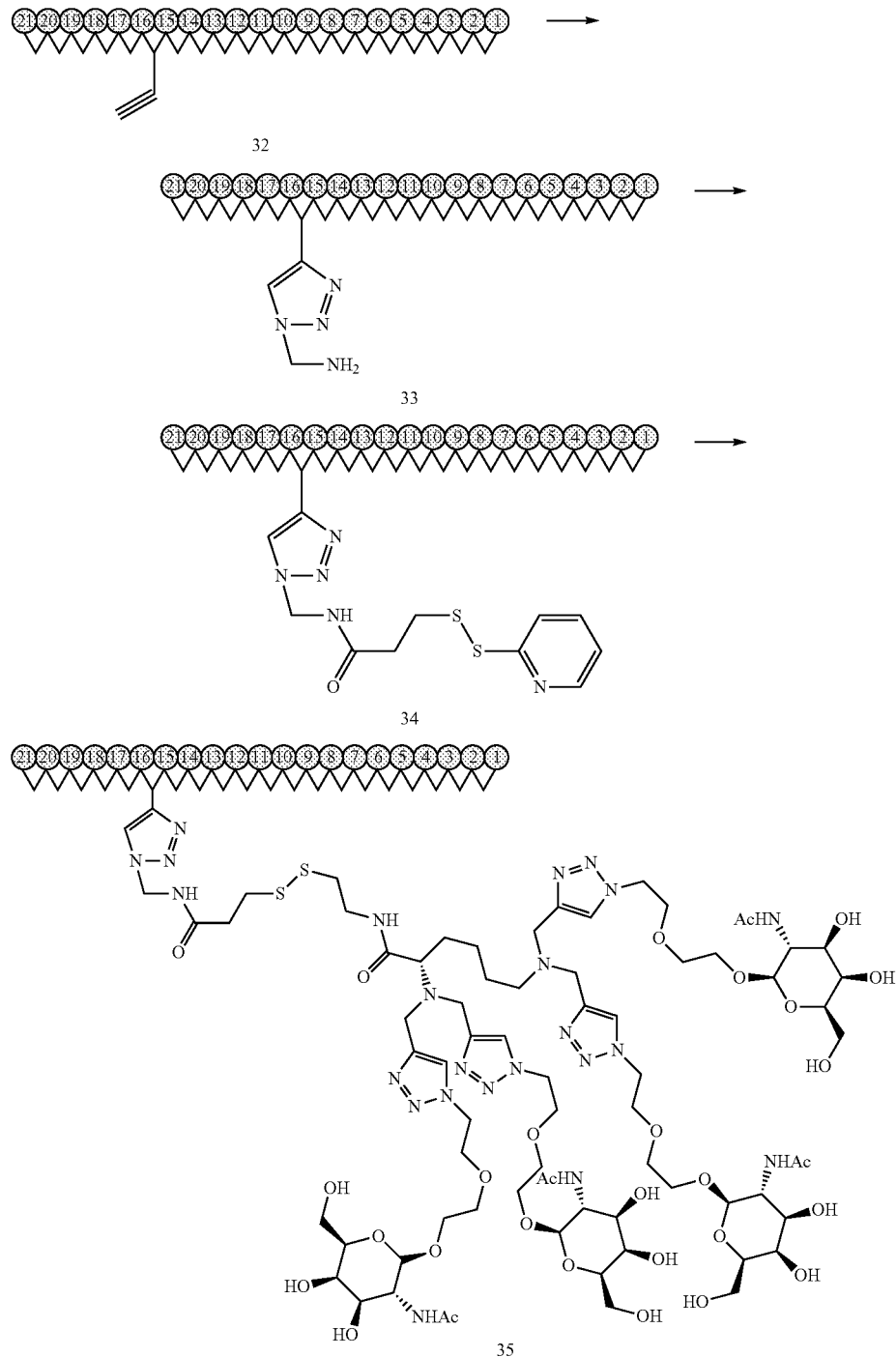

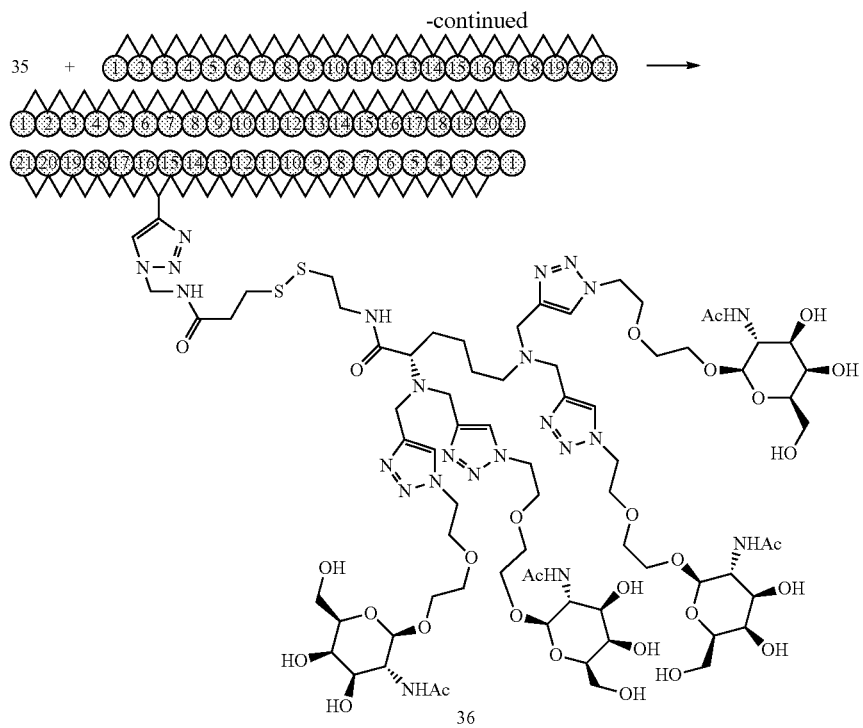

Synthesis of Compound 33

To a degassed solution of 2'-click 15 GS Compound 32 (130 mg, 0.019 mmol) and (9H-fluoren-9-yl)methyl (2-azidoethyl)carbamate (29.1 mg, 0.095 mmol) in 3:1 DMA/water (2 mL) was added a solution of Copper (I) bromide-dimethylsulfide Complex (9.72 mg, 0.042 mmol) dissolved in degassed DMSO (0.32 mL). The mixture was stirred at 45° C. for 2 h, cooled to room temperature, and added pH 8 EDTA (0.5 M, 2 mL) to quench reaction. Stirred for 15 min and purified on a XBridge Prep Phenyl column (5 uM, 30×150 mm) using a gradient of 0-45% $CH_3CN$/water containing 100 mM TEAA. The fractions were concentrated via dialysis. To the combined material in water (3 mL) was added a solution of piperidine (936 µL, 1.891 mmol). The mixture was stored at 4° C. for 18 h, diluted with water (10 mL) and filtered off solids through syringe filter. Added pH 8 EDTA (0.5 M, 2 mL), concentrated via dialysis and lyophilized to yield Compound 33.

Synthesis of Compound 34

To a solution of 2'-15 click C2 NH2 GS Compound 33 (43.6 mg, 6.26 µmol) in 200 mM $NaHCO_3$ soln (2000 µl) and formamide (1000 uL) was added a solution of N-Succinimidyl-3-[2-pyridyldithio]propionate (17.9 mg, 0.057 mmol) dissolved in DMSO (298 uL). The mixture was stirred at 10° C. for 15 min, diluted with water (10 mL) and Formamide (1 mL), and concentrated by dialysis. Added 2M TEAA (200 uL) and purified on a XBridge Prep Phenyl column (5 uM, 19×250 mm) using a gradient of 5-40% $CH_3CN$/water containing 100 mM TEAA. The fractions were concentrated via dialysis and lyophilized to yield Compound 34.

Synthesis of 2'-15 TetraGalNAc-siRNA Conjugate 35 (Ex. 16)

To a solution of 2'-15 click C2 NH2 NHS SPDP GS Compound 34 (13 mg, 1.82 µmol) in 1:1 formamide/water (200 µl) was added a solution of tetraGalNAc SH (4.62 mg, 2.72 µmol) in formamide (200 uL). The mixture was stirred at room temperature for 3.5 h, added 2M TEAA (50 uL) and purified on a XBridge Prep Phenyl column (5 uM, 19×250 mm) using a gradient of 2-35% $CH_3CN$/water containing 100 mM TEAA. The fractions were concentrated via dialysis and lyophilized. The resulting solid was purified on a Proteomix SAX-NP10 column (22.1×50 mm) using a gradient of 2-30% (Solvent A: 60:40 TFE/water with 40 mM Et3N, Solvent B: 60:40 TFE/water with 40 mM Et3N, 1M Guanidine HCl). The fractions were concentrated via dialysis and lyophilized to yield Conjugate 35.

Synthesis of Conjugates 36 and 37 (Ex. 17 and Ex. 18)

The procedure detailed for Conjugate 19-1 was used to duplex Conjugate 35 and the appropriate passenger strand to prepare Conjugates 36 and 37, respectively.

Examples 19-26

Synthesis of Conjugates 38-45 (Exs. 19-26)

Schemes 10 and 11 below were used to prepare Conjugates 38-44.

SCHEME 10
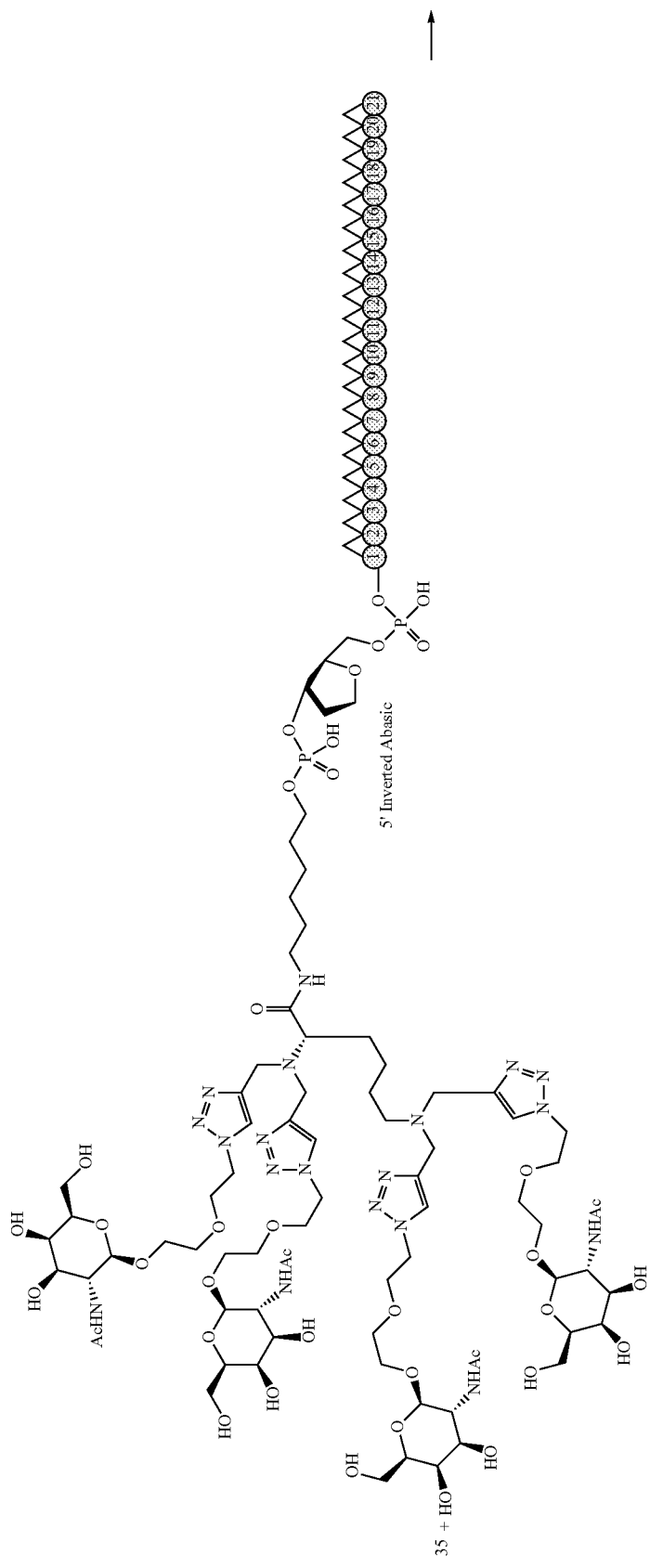

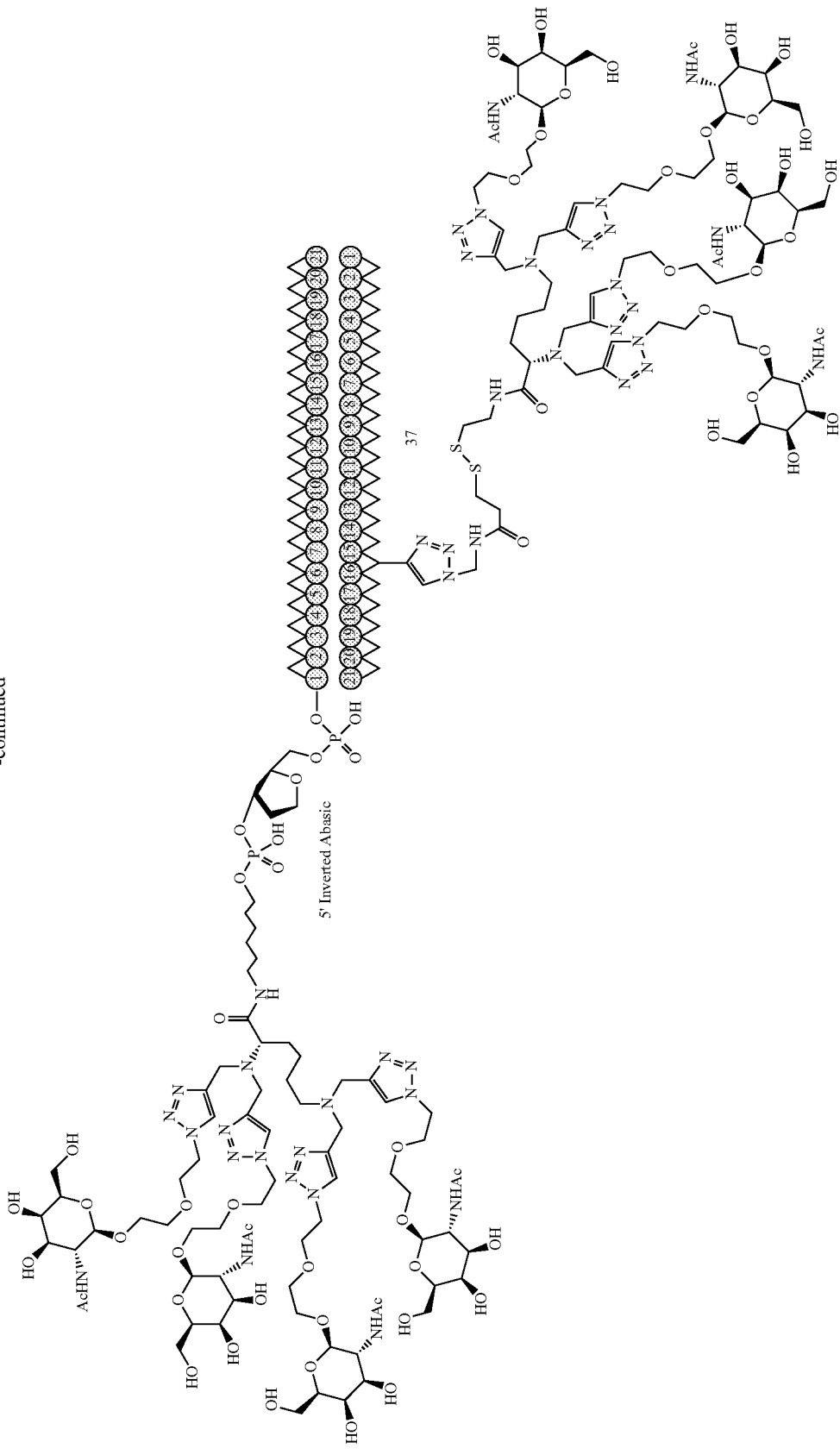

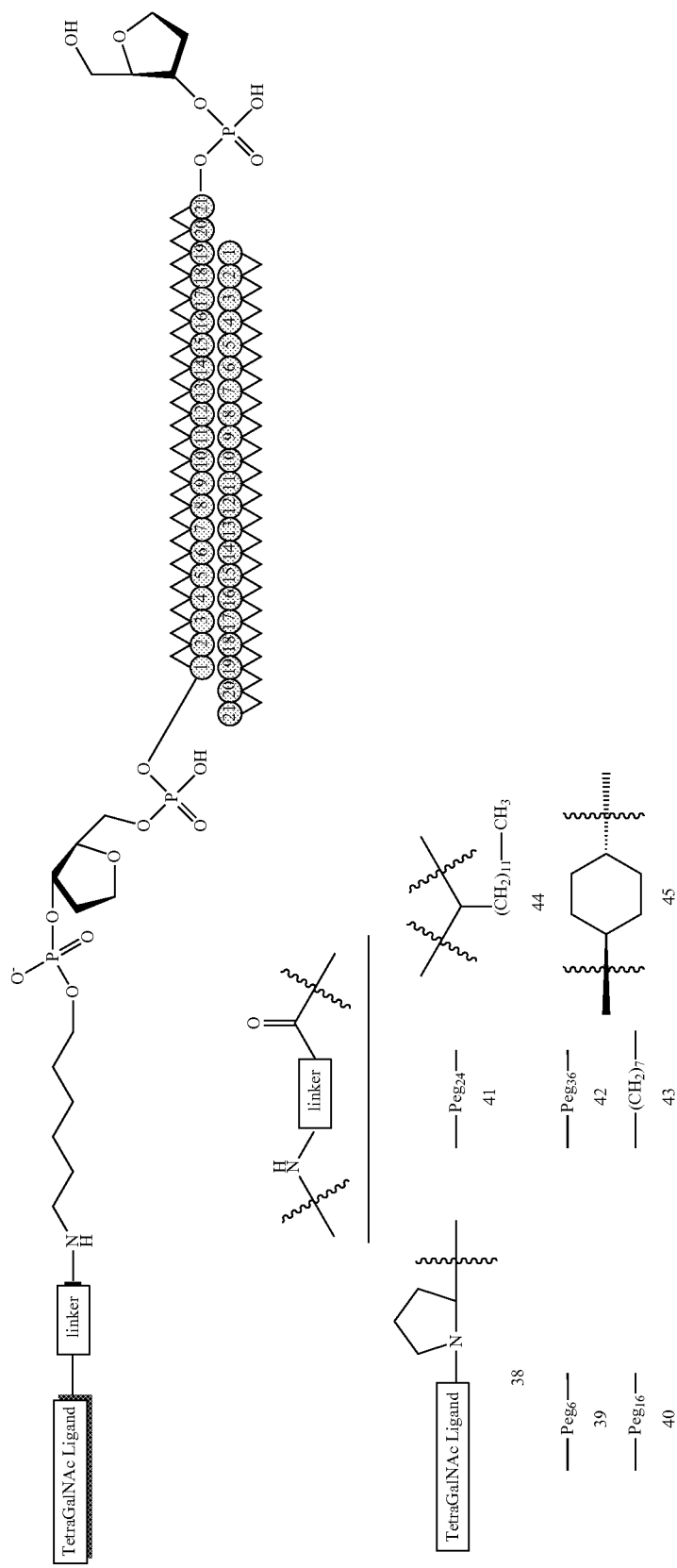

Scheme 11. Examples of different linkers from Table 2 used to conjugate tetraGalNAc to siRNA.

Step 1: Passenger-RNA and Linker, Example with Proline to Illustrate Protocol

To a solution of FMOC-PRO-OH (11.11 mg, 0.033 μmol) in 120 μL DMSO were added DIPEA (43.2 μl, 0.247 μmol) followed by HATU (10.96 mg, 0.029 μmol). The mixture, slightly yellow, was stirred at room temperature for 30 min. The mixture was then added to a solution of the oligonucleotide passenger strand TEAA salt (60 mg, 8.24 μmol) in 500 μL of (10% $H_2O$/DMSO), and the mixture continued to stir at room temperature for one hour. The reaction mixture showed desired product via LC-MS. To the reaction mixture was added diethylamine (43.0 μl, 0.412 μmol) and the mixture was stirred for one hour, confirmed desired product via LC-MS. The reaction mixture was purified by centrifugal dialysis using 3 kDa cut-off membrane. The process was repeated three times with water (14 mL each time). The resulting solution was concentrated, frozen, and lyophilized overnight to yield product as a white fluffy solid. LC/MS confirms product [7384.9]

Step 2: TetraGalNAc-linker-passenger RNA

To a solution of TetraGalNAc Compound 10 (53.2 mg, 0.033 μmol) in 532 μL DMSO were added DIPEA (42.6 μl, 0.244 μmol) followed by HATU (12.36 mg, 0.033 μmol). The mixture, slightly yellow, was stirred at RT for 30 min The mixture was then added to a solution of the linker-oligonucleotide passenger strand in 500 μL of DMSO, and the mixture continued to stir at room temperature for two hours. LC/MS showed desired product. The reaction mixture was subjected to centrifugal dialysis using 3 kDa cut-off membrane. The process was repeated three times with water (14 mL each time). The resulting solution was purified by Gilson PLC 2020 using XBRIDGE PHENYL, 10-27% $CH_3CN$ with 200 μM TEAA for 35 minutes. Collection solution was concentrated via centrifugal dialysis using 3 kDa cut-off membrane. The resulting concentrated solution was treated with 1.0N NaCl and centrifugal dialysis. The process was repeated five times with water (14 mL each time). The resulting concentrated solution (~1.5 mL) was frozen and lyophilized overnight to yield product as a white fluffy solid. LC/MS confirms product [9002.5].

Step 3: Duplex Formation

To a TetraGalNAc-linker-RNA (18.5 mg, 2.055 μmol) in 1.5 mL of water was duplexed with ApoB guide strand (14.12 mg, 2.055 μmol) in 1.5 mL of water. The mixture was heated at 90° C. for 5 min with stir bar. The duplex was cooled and stir bar removed. The solution was lyophilized over two days to yield desired duplex Conjugate 38 as a white fluffy solid. LC/MS confirms product [16048].

ALL the remaining conjugates were prepared using the same general procedure.

Examples 27-29

Synthesis of Compounds/Conjugates 46-48

Schemes 12 below was used to prepare Compounds and/or Conjugates 46-48.

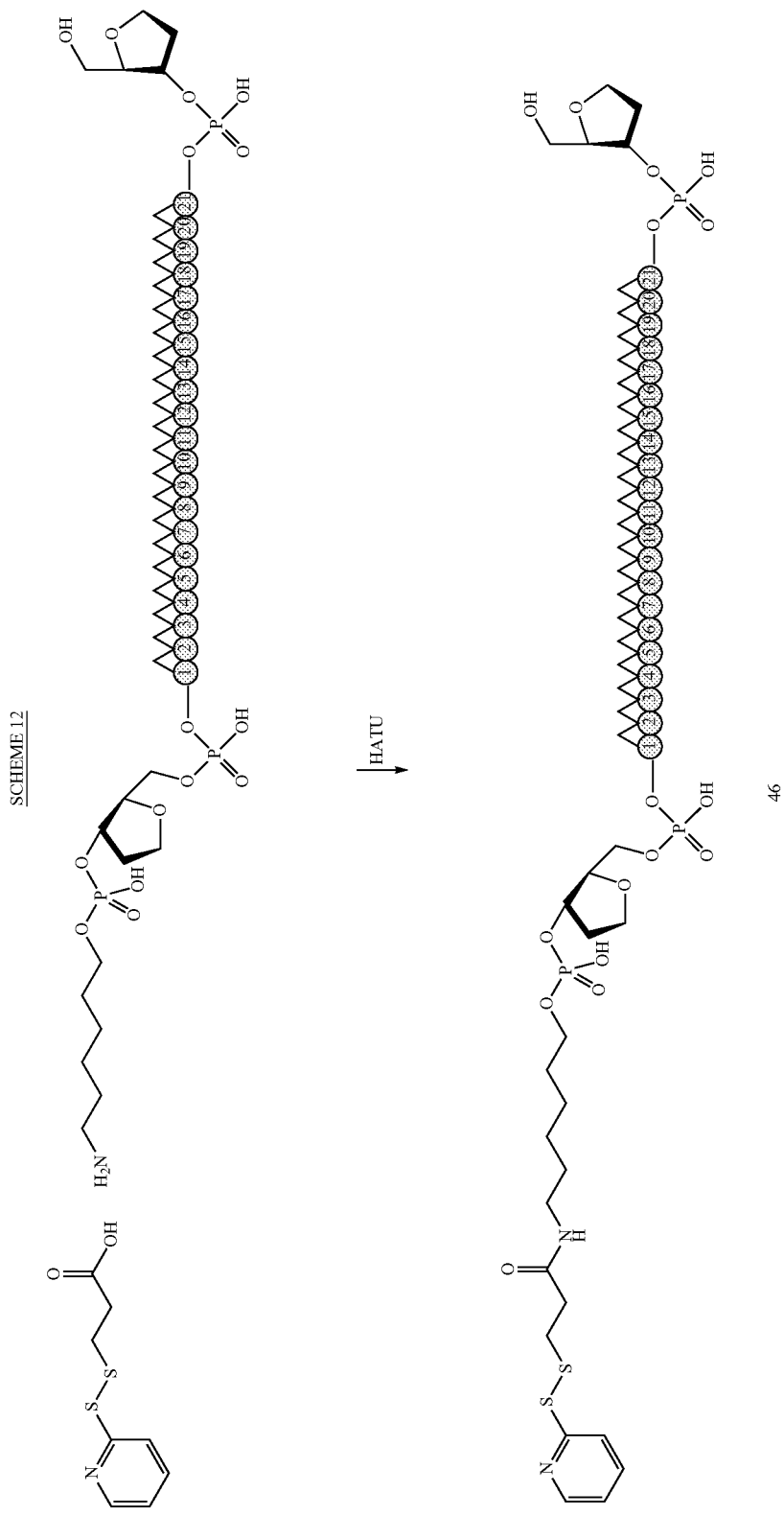

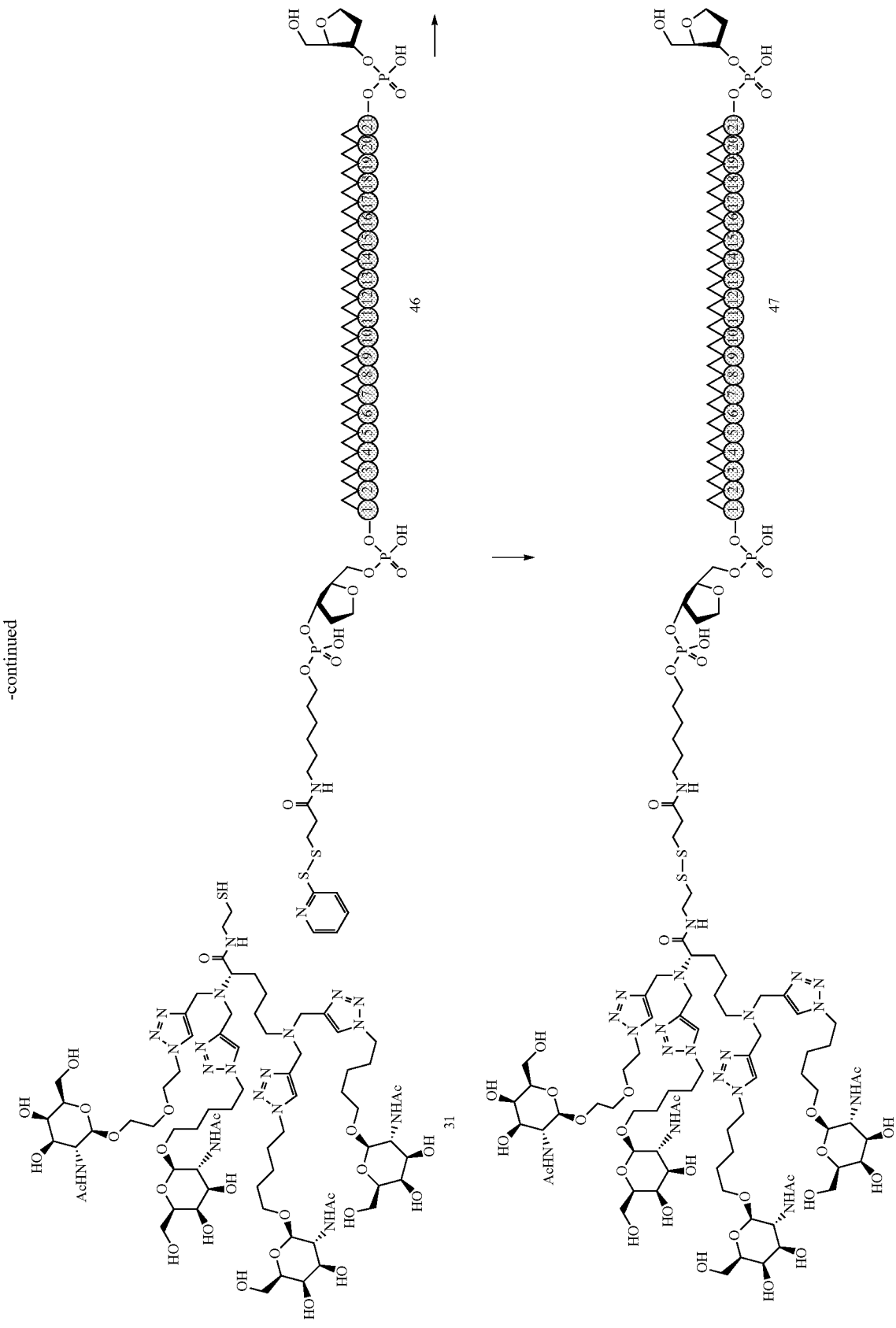

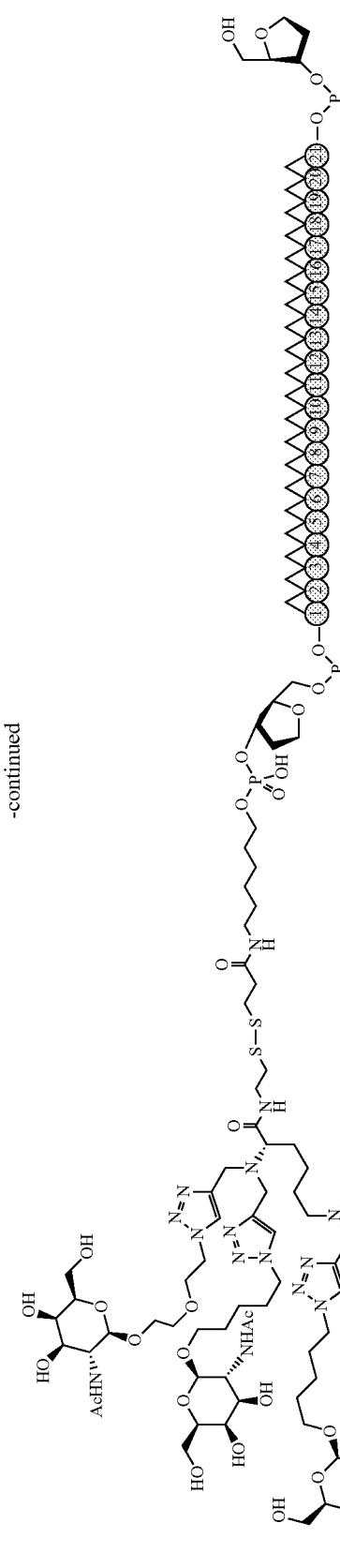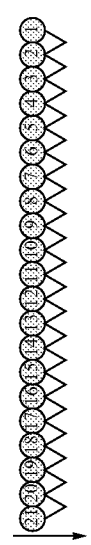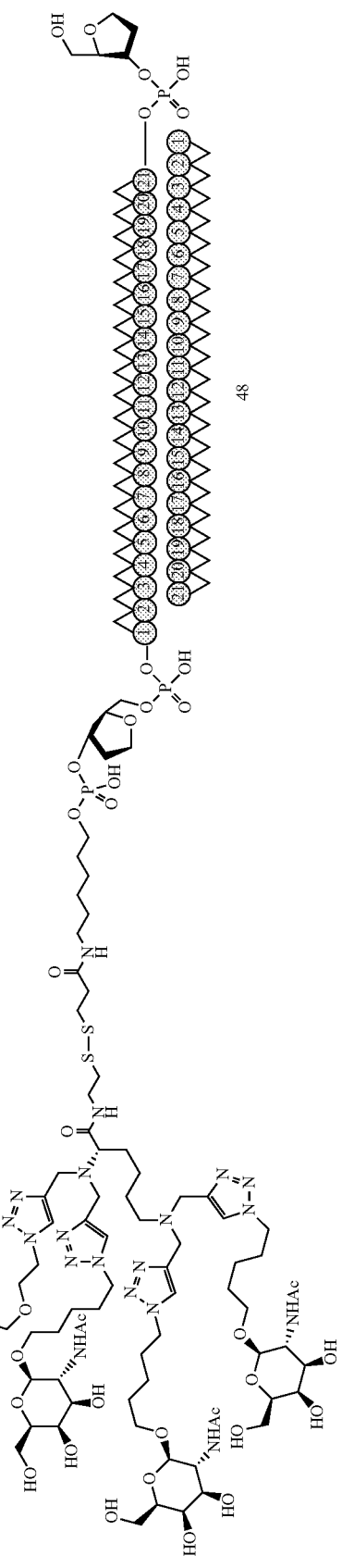

Synthesis of RNA Compound 46 (Ex. 27)

SPDP Acid (2.2 mg, 10.3 μmol) was dissolved DMSO 100 μL and N,N-diisopropylethylamine (14.0 μl, 0.08 mmol), HATU (19.6 mg, 0.051 mmol) were added sequentially. RNA (15 mg, 2.06 μmol) in 200 μL of DMSO:Water (9:1) was added and the resulting reaction mixture was stirred for 1 h, reaction was quenched by addition of 3 mL water and dialyzed down to 500 μL, diluted by formamide to 3 mL and purified by SAX (Buffer A: 60% TFE in water, 20 mM TEA, Buffer B: 60% TFE in water, 20 mM TEA, 1 M CsCl, gradient A/B from 100/0 to 35/65 over 15 min). The collected fractions were combined and dialyzed against water and lyophilized to afford Compound 46 as a white solid. Calculated mass: $[M-H]^-$:$C_{234}H_{300}F_{08}N_{72}O_{150}P_{23}S_3$, 7480.1; observed: 7483.0.

Synthesis of Conjugate 47 (Ex. 28)

RNA Compound 46 (22 mg, 2.9 μmol) and tetraGalNAc Thiol Compound 31 (10.0 mg, 5.9 μmol) were dissolved in formamide:pH=6.8 Tris buffer (3:1) 400 μL and stirred for 1 h. The reaction mixture was purified by SAX (Buffer A: 60% TFE in water, 20 mM TEA, Buffer B: 60% TFE in water, 20 mM TEA, 1 M CsCl, gradient A/B from 100/0 to 35/65 over 15 min). The collected fractions were combined and dialyzed against water and lyophilized to afford Conjugate 47 as a white solid. Calculated mass: $[M-H]^-$: $C_{297}H_{410}F_8N_{90}O_{179}P_{23}S_3$, 9063.9; observed: 9066.2.

Synthesis of Conjugate 48 (Ex. 29)

Conjugate 47 (10.9 mg, 1.20 μmol) and guide strand (7.81 mg, 1.14 μmol) were mixed in RNAse free water 1 mL for 2 h. The reaction mixture was lyophilized to afford duplex Conjugate 48 in quantitative yield.

Examples 30-32

Synthesis of Compounds/Conjugates 49-51

Schemes 13 below was used to prepare Compounds and/or Conjugates 49-51.

SCHEME 13

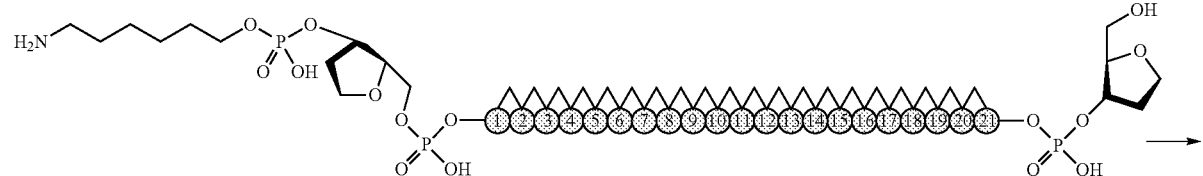

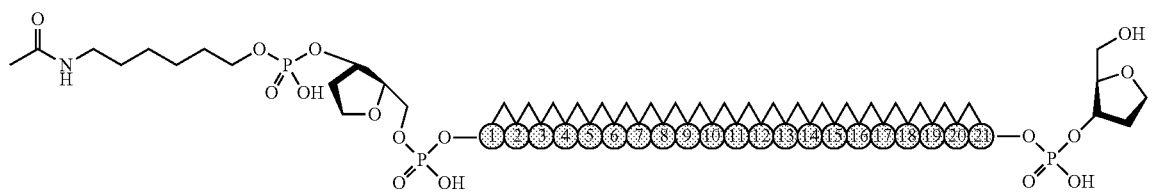

43

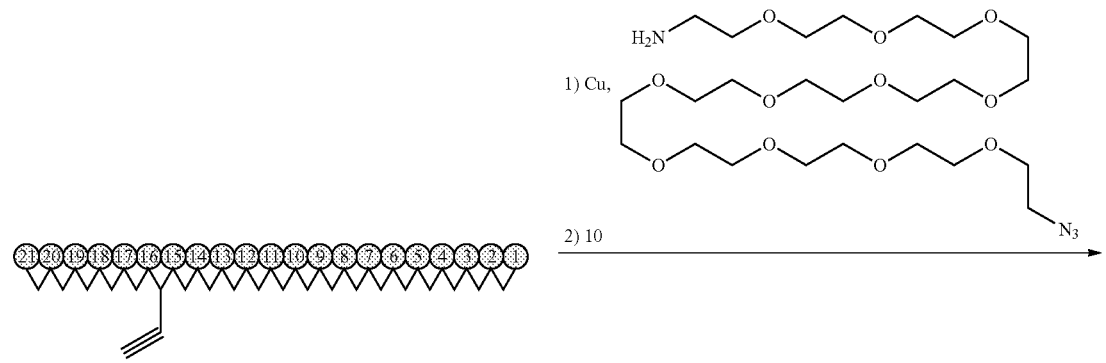

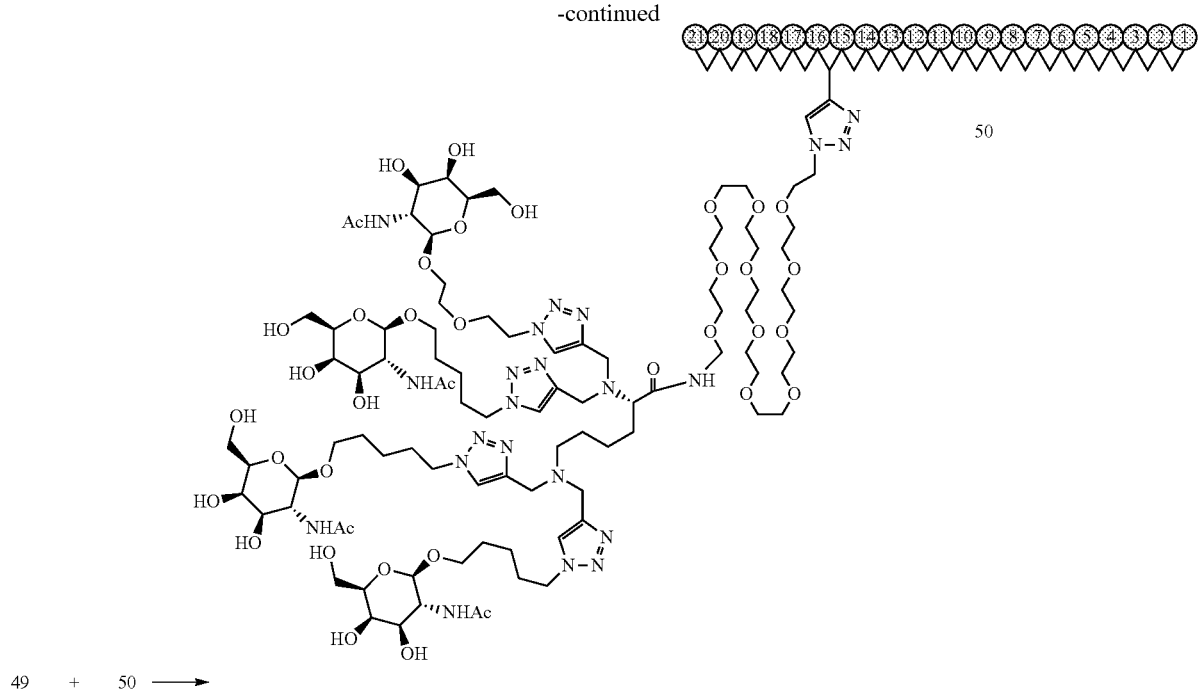
50
49 + 50 ⟶
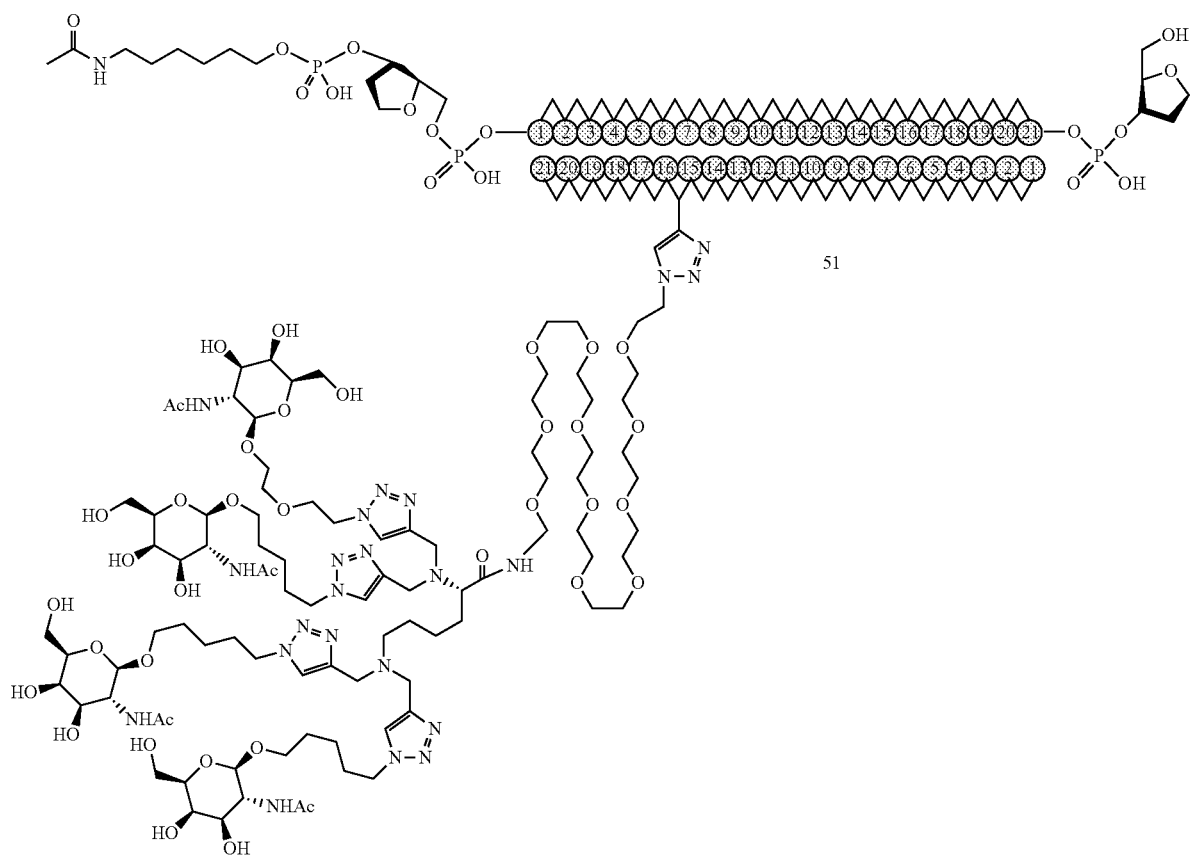
51
Synthesis of RNA Compound 49 (Ex. 30)
33.3 mg of siRNA passenger strand was weighed into a 4mL vial then 1 mL 100 mM NaHCO3 was added to dissolve. Added 0.86 uL of propionic anhydride and let stir at RT. After aging ~2 h, spin dialyzed 3× against water. Filtered through frit and the solution was dried via lyophilization to afford 30.8 mg RNA Compound 49.

Synthesis of Conjugate 50 (Ex. 31)

Step 1. Charge 2.8 mg azide, 25.7 mg siRNA, 25 ml N2 sparged DMSO and 4 ml water to 40 mL vial. Sparge with $N_2$. Charge 2.98 mL of Cu/ligand solution ($N_2$ sparged, 20/100 umol in 10 ml DMSO). Agitate at RT under sparged $N_2$.

Step 2. Charge Compound 10 and 1 ml DMSO. Charge 6 uL of DIPEA and agitate for 2 min. Charge 6 mg HBTU and agitate for 2 min. Charge siRNA mixture from Step 1. The reaction was not complete so repeated with half of previous reagent charge. Evaporated the reaction mixture, dialyzed and HPLC purified (X-Bridge Phenyl, TEAA/ACN gradient). Evaporated, dialyze and lyophilized to afford Conjugate 50.

Synthesis of Conjugate 51 (Ex. 32)

Dissolve GS (Conjugate 50) 10.65 mg in 1 ml water and dissolve PS (Conjugate 49) 10.20 mg in 1.17 ml water. Added 8.7 mg of Conjugate 49 to all of Conjugate 50 to form a 1:1 duplex. Heat to 90°C. for 1 min, cool to RT over 15 min. The solution was filtered and dried via lyophilizaiton to afford Conjugate 51 as a white solid.

RNA Silencing Activity of Compounds Transfected with Lipofectamine in Luciferase Constructs HEK293 cells stably transfected with luciferase vector that contains target sites for siRNA in 3'UTR of renilla luciferase were generated. These cells were seeded on 96-well tissue culture plates (Corning: #3903) at a density of 7.5e3 cells per well in DMEM 10% serum media. Cellular plates were then incubated at 37° C./5% CO2 for 24 hr. After incubation, plates were treated with test compounds co-transfected with transfection reagent Lipofectamine 2000 (invitrogen: #11668-019) in Opti-MEM (Gibco: #31985) in accordance to manufacturers protocol. The treatment concentrations ranged from 10 nM to 0.03 pM. Treated plates were then incubated for 24 hr at 37° C./5% CO2. Following treatment incubation, cells were lysed and processed in accordance to Dual-Glo™ Luciferase Assay (Promega: E2920) and read on a TECAN safire2 plate reader.

RNA Silencing Activity of Compounds Transfected with Lipofectamine in HepG2 Cells HepG2 cells (ATCC: HB-8065) were seeded on collagen coated plates (BioCoat: 356649) at a density of 7.5e3 cells per well in DMEM 10% serum media. Cellular plates were then incubated at 37° C./5% CO2 for 24 hr. After incubation, plates were treated with test compounds co-transfected with transfection reagent Lipofectamine 2000 (invitrogen: 11668-019) in Opti-MEM (Gibco: 31985) in accordance to invitrogen protocol. The treatment concentrations ranged from 10 nM to 0.03 pM. Treated plates were then incubated for 24 hr at 37° C./5% CO2. Following treatment incubation, cells were lysed with PLA Buffer (AB: 4448542) in accordance to supplied protocol. Resulting cell lysate was reverse transcribed to cDNA using High Capacity cDNA Kit (AB: 4368813) and run through qPCR using Life Technology 7900.

In vivo Evaluation of RNAi Activity

CD1 female mice were dosed by subcutaneous injection in 200 ul volume. Animals were observed for behavioral or physiological changes. Animals were sacrificed 72 hrs post dose by CO2 asphyxiation followed by ex-sanguination via cardiac puncture. The liver samples were as 3 mm punches from the medial lobe and put into RNAlater tubes for isolation of total RNA. The mRNA knockdown analysis was conducted by Taqman analysis using standard procedures.

A summary of in vitro and in vivo data of selected Compounds/Conjugates is shown in Table 4 presented earlier.

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

What is claimed is:

1. A modular composition comprising 1) a single stranded or double stranded oligonucleotide;

2) one or more tetraGalNAc ligands of Formula (I), (II) or (III), which may be the same or different:

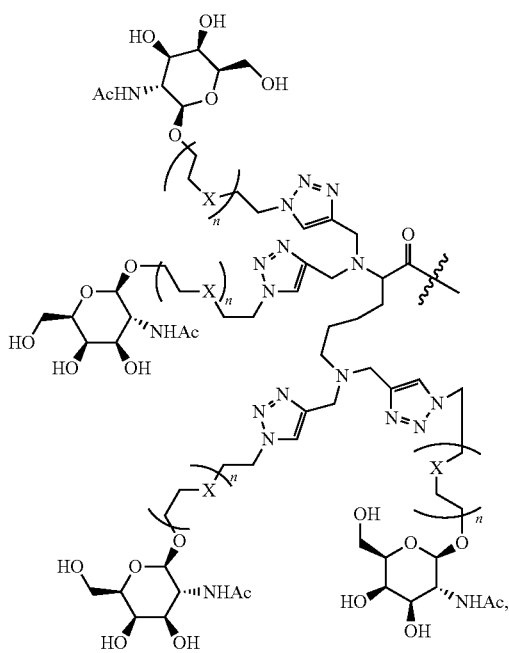

(I)

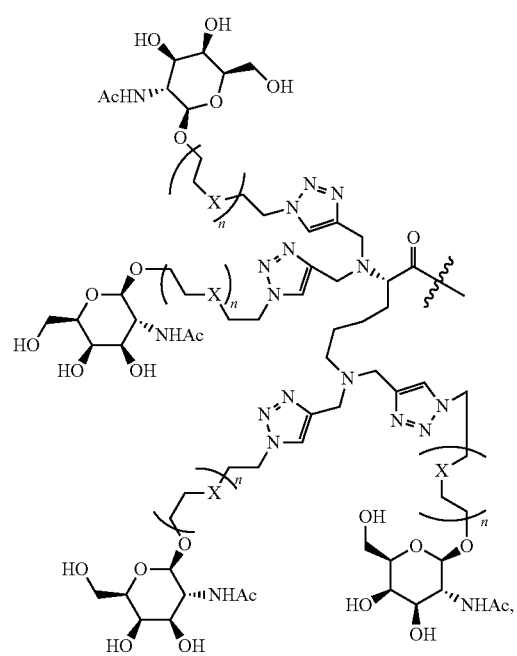

(II)

-continued

-continued

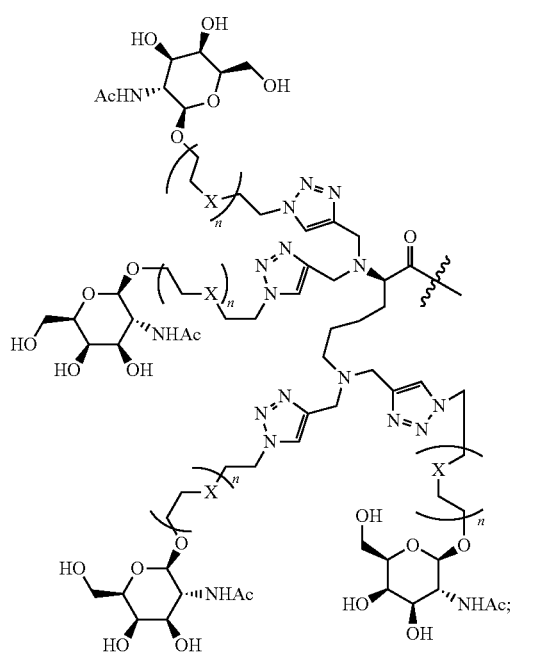
(III)

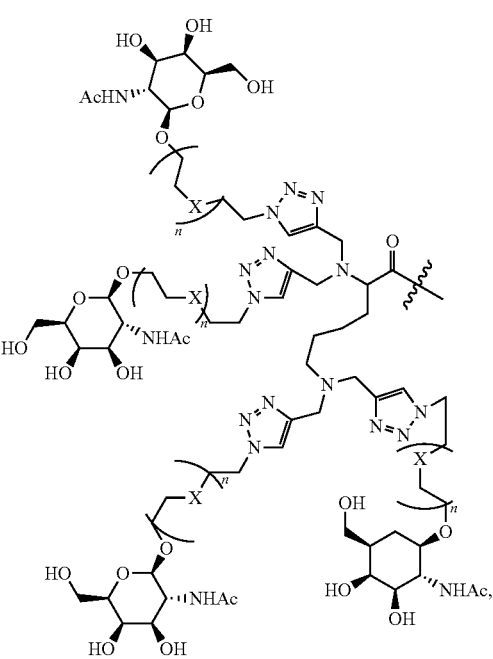
(I)

optionally, 3) one or more linkers, which may be the same or different; and optionally, 4) one or more targeting ligands, solubilizing agents, pharmacokinetics enhancing agents, lipids, and/or masking agents, wherein X is —O—, —S—, —CR$^1$R$^2$— or —NR$^1$—, wherein R$^1$ and R$^2$ are each independently selected from the group consisting of hydrogen and C1-C6 alkyl; n is 1, 2, 3, or 4; and the bond with "〜〜〜" indicates the point of attachment of the tetraGalNAc ligands to the oligonucleotide, either directly or through one or more optionally present linkers.

2. The modular composition of claim 1 comprising:
1) a single stranded or double stranded oligonucleotide;
2) 1-8 tetraGalNAc ligands of Formula (II), which may be the same or different, wherein X is —O—, —S—, —CH$_2$— or —NH—; and n is 1, 2, 3, or 4;
3) 1-16 linkers, which may be the same or different; and
optionally, 4) 1-8 targeting ligands, solubilizing agents, pharmacokinetics enhancing agents, lipids, and/or masking agents.

3. A modular composition comprising:
1) a single stranded or double stranded siRNA;
2) 1-8 tetraGalNAc ligands of Formula (I), (II), or (III), which may be the same or different,

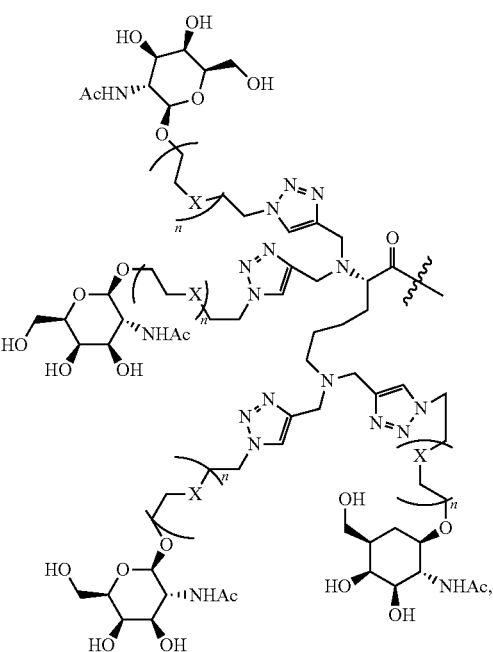
(II)

(III)

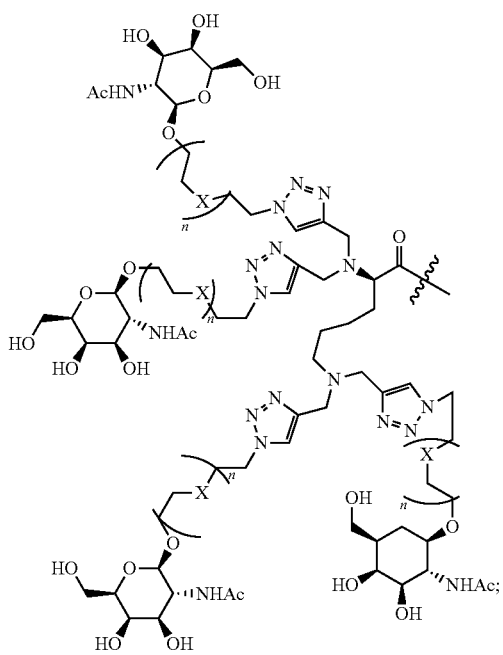

3) 1-16 linkers, which may be the same or different; and optionally, 4) 1-8 targeting ligands, solubilizing agents, pharmacokinetics enhancing agents, lipids, and/or masking agents, wherein X is —O—, —S—, —CR$^1$R$^2$—or —NR$^1$—, wherein R$^1$ and R$^2$ are each independently selected from the group consisting of hydrogen and C1-C6 alkyl; n is 1, 2, 3, or 4; and the bond with "∼∼∼" indicates the point of attachment of the tetraGalNAc ligands to the oligonucleotide, either directly or through one or more optionally present linkers.

4. The modular composition of claim 3, wherein the tetraGalNAc ligands are attached to the siRNA at different 2'-positions of the ribose rings and/or at different terminal 3' and/or 5'-positions of the siRNA; and wherein the tetraGalNAc ligands are attached to the siRNA optionally via linkers.

5. The modular composition of claim 3, wherein X of Formula (II) is —O—, —S— or —CH$_2$—; and n is 1, 2 or 3.

6. The modular composition of claim 3, wherein the composition comprises 1-4 tetraGalNAc ligands, which may be the same or different.

7. The modular composition of claim 3, wherein the siRNA is double stranded; and wherein the tetraGalNAc ligands are attached to the guide strand or the passenger strand of the siRNA at different 2'-positions of the ribose rings of the siRNA.

8. The modular composition of claim 3, wherein the siRNA is double stranded; and wherein the tetraGalNAc ligands are attached to the guide strand or the passenger strand of the siRNA at different terminal 3' and/or 5'-positions.

9. The modular composition of claim 3, wherein the siRNA is double stranded; and wherein the tetraGalNAc ligands are attached to both the guide strand and the passenger strand of the siRNA at different 2'-positions of the ribose rings and/or different terminal 3' and/or 5'-positions.

10. The modular composition of claim 3, wherein the composition comprises 2-8 tetraGalNAc ligands of Formula (II), which may be the same or different; and the tetraGalNAc ligands are attached to the same strand of the siRNA.

11. The modular composition of claim 3, wherein the composition comprises 2-8 tetraGalNAc ligands of Formula (II), which may be the same or different; and the tetraGalNAc ligands are attached to different strands of the siRNA.

12. The modular composition of claim 3, wherein the tetraGalNAc ligands are attached to the same or different strands of the siRNA via linkers.

13. The modular composition of claim 12, wherein each linker is independently selected from the group consisting of:

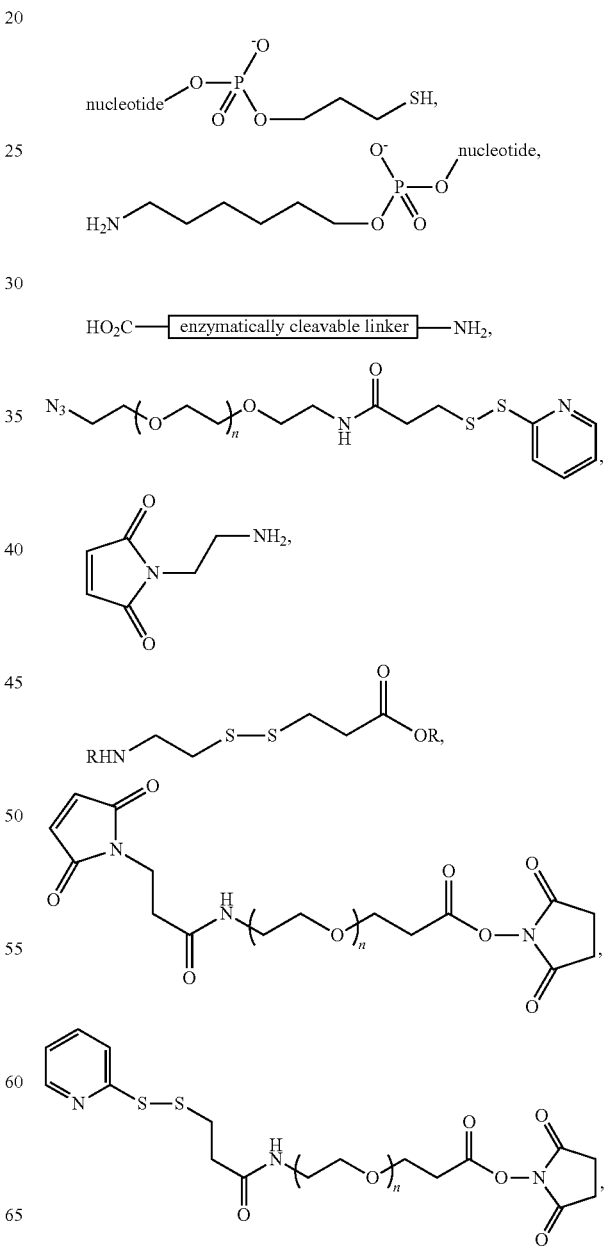

121
-continued
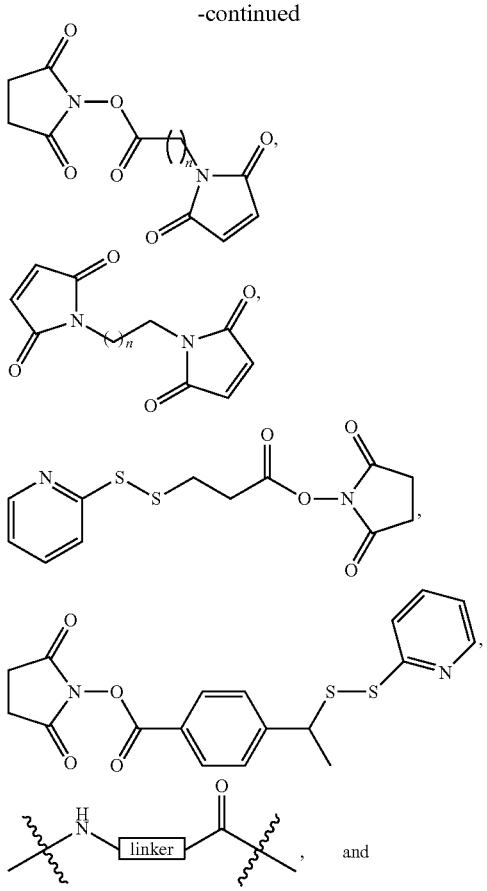
122
-continued
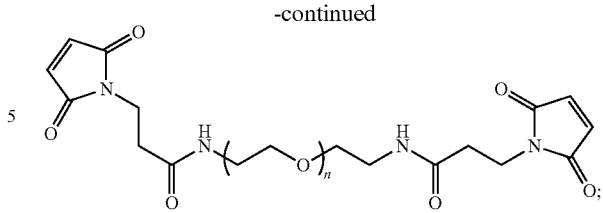
wherein:
each R is independently H, Boc (tert-butyloxycarbonyl), Cbz (carboxybenzyl), Ac (acetyl), a PEG, a lipid, a targeting ligand, linker(s), or peptide(s);
linker is 
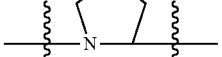, —(PEG)$_n$—, —(CH$_2$)$_n$—, (CH$_3$)$_{11}$—CH$_3$, or 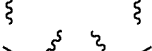;
and
each n is 0 to 750.
14. The modular composition of claim 12, wherein each linker is independently selected from the group consisting of:
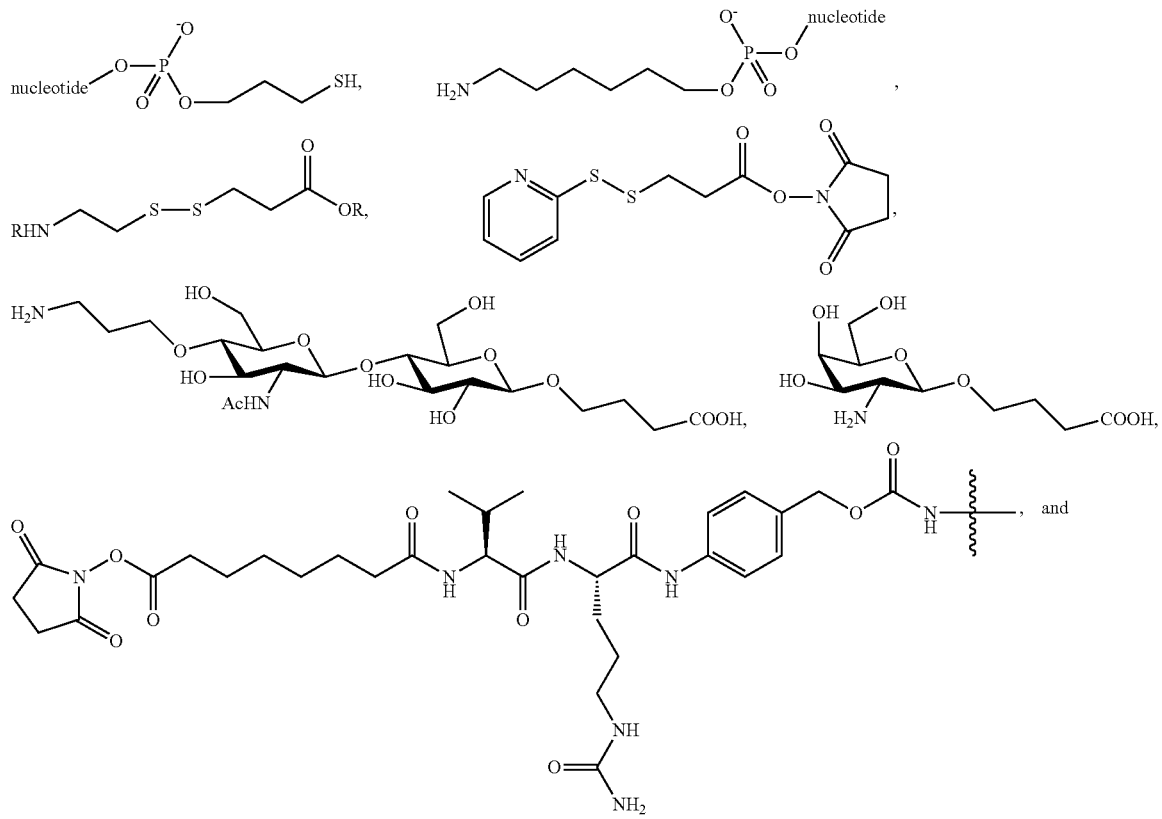

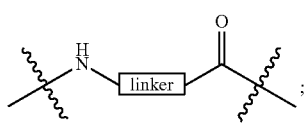

wherein:
each R is independently H, Boc (tert-butyloxycarbonyl), Cbz (carboxybenzyl), Ac (acetyl), a PEG, a lipid, a targeting ligand, linker(s), or peptide(s);

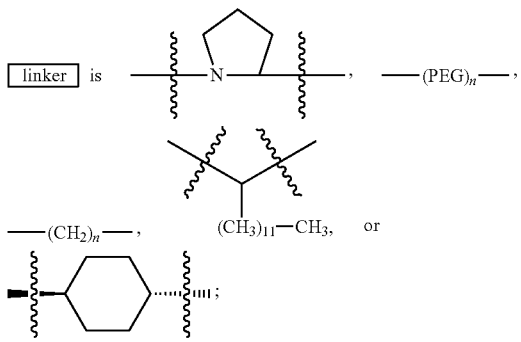

and
each n is 0 to 750.

15. The modular composition of claim 3,
wherein the siRNA is double stranded; and
wherein the optional targeting ligands, solubilizing agents, pharmacokinetics enhancing agents, lipids, and/or masking agents are attached to the same strand or different strands of the siRNA via linkers.

16. A modular composition comprising
1) a double stranded siRNA;
2) 1-8 tetraGalNAc ligands of Formula (IV), (V) or (VI):

(IV)

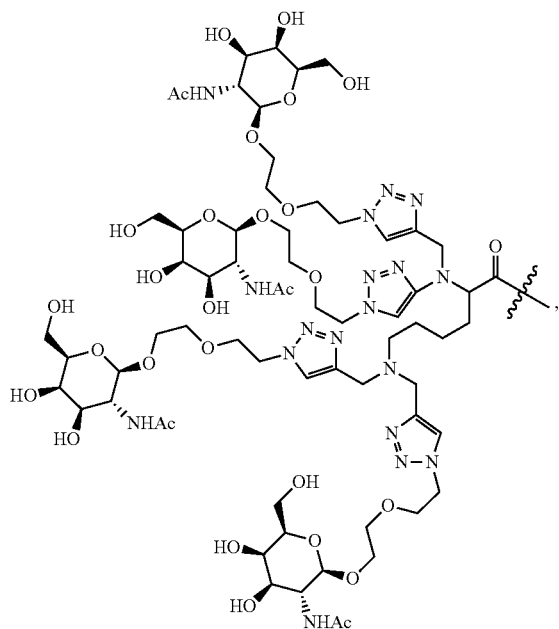

(V)

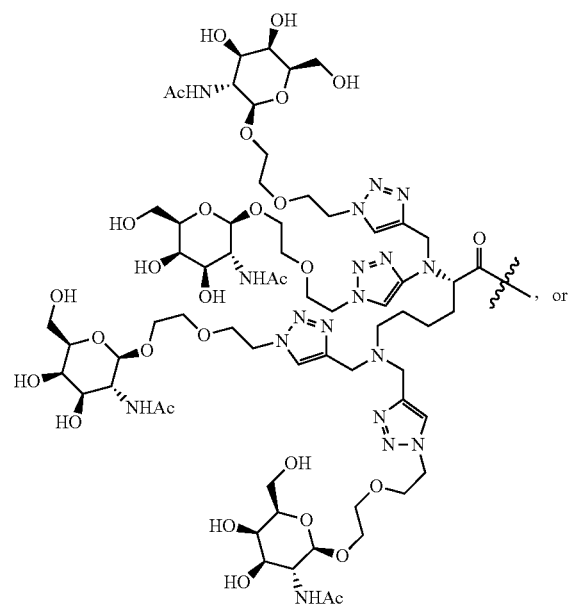

, or (VI)

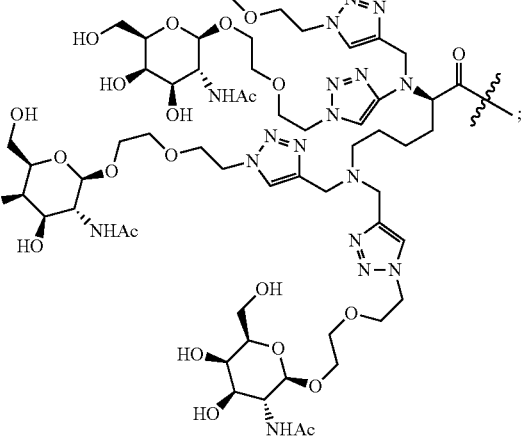

;

optionally, 3) 1-16 linkers, which may be the same or different; and
optionally, 4) 1-8 targeting ligands, solubilizing agents, pharmacokinetics enhancing agents, lipids, and/or masking agents, wherein the bond with "⌇" indicates the point of attachment of the tetraGalNAc ligands to the oligonucleotide, either directly or through one or more optionally present linkers.

17. The modular composition of claim 16 comprising:
1) a double stranded siRNA;
2) 1-3 tetraGalNAc ligands of Formula (V);
optionally, 3) 1-6 linkers, which may be the same or different; and
optionally, 4) 1-3 targeting ligands, solubilizing agents, pharmacokinetics enhancing agents, lipids, and/or masking agents;
wherein the tetraGalNAc ligands are attached to the siRNA at different 2'-positions of the ribose rings and/or at different terminal 3' and/or 5'-positions of the siRNA; and wherein the tetraGalNAc ligands are attached to the siRNA optionally via linkers.

18. The modular composition of claim 17 comprising 2-3 tetraGalNAc ligands, wherein the tetraGalNAc ligands are attached to the same strand or different strands of the siRNA via linkers.

19. The modular composition of claim 17 comprising:
1) a double stranded siRNA;
2) 1-2 tetraGalNAc ligands of Formula (V);
3) 1-4 linkers, which may be the same or different; and
optionally, 4) 1-2 targeting ligands, solubilizing agents, pharmacokinetics enhancing agents, lipids, and/or masking agents;
wherein the tetraGalNAc ligands are attached to the siRNA at different 2'-positions of the ribose rings and/or at different terminal 3' and/or 5'-positions of the siRNA; and
wherein the tetraGalNAc ligands are attached to the siRNA via linkers.

20. The modular composition of claim 19 comprising 2 tetraGalNAc ligands, wherein the tetraGalNAc ligands are attached to the same strand or different strands of the siRNA via linkers.

21. The modular composition of claim 19 comprising 1 tetraGalNAc ligand, wherein the tetraGalNAc ligand is attached to the siRNA via a linker.

22. A pharmaceutical composition comprising the modular composition of claim 1 and a pharmaceutically acceptable excipient.

* * * * *

UNITED STATES PATENT AND TRADEMARK OFFICE
CERTIFICATE OF CORRECTION

PATENT NO. : 9,540,639 B2  Page 1 of 7
APPLICATION NO. : 14/398317
DATED : January 10, 2017
INVENTOR(S) : David Tellers et al.

It is certified that error appears in the above-identified patent and that said Letters Patent is hereby corrected as shown below:

In the Claims

In Claim 1, Column 115, between Lines 40 and 65, delete

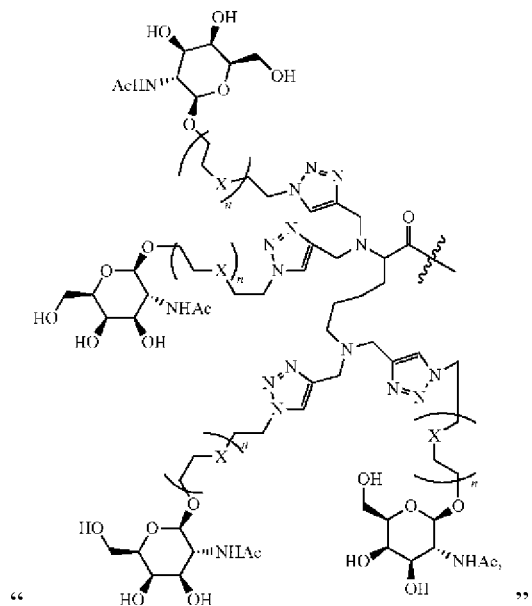

Signed and Sealed this
Ninth Day of January, 2018

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,540,639 B2

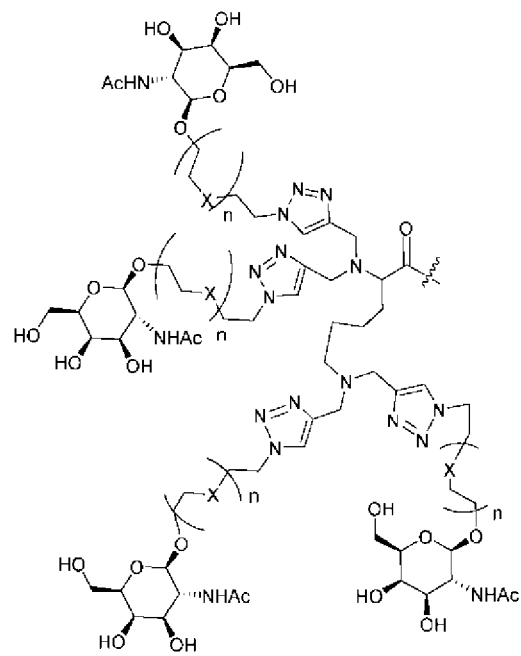

and insert in its place --                                            --.

In Claim 1, Column 116, between Lines 40 and 65, delete

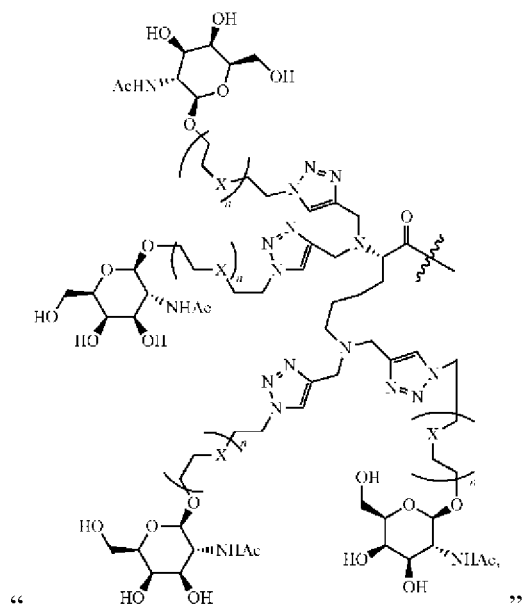

"                                            "

CERTIFICATE OF CORRECTION (continued)
U.S. Pat. No. 9,540,639 B2

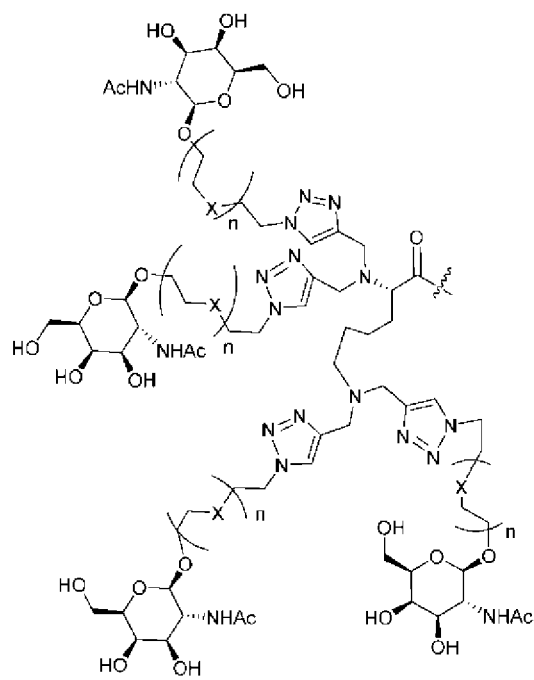

and insert in its place -- --.

In Claim 1, Column 117, between Lines 1 and 30, delete

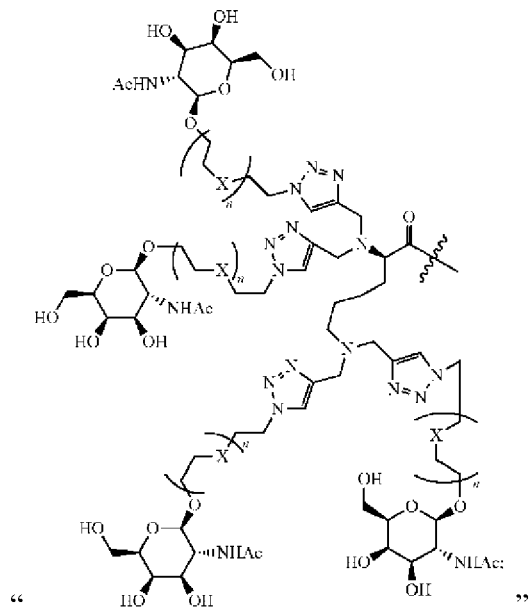

" "

CERTIFICATE OF CORRECTION (continued)
U.S. Pat. No. 9,540,639 B2

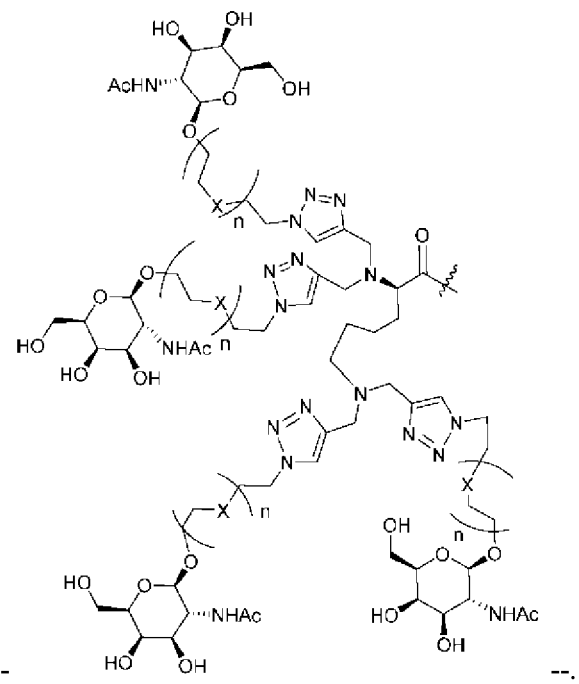

and insert in its place -- --.

In Claim 3, Column 118, between Lines 1 and 30, delete

" 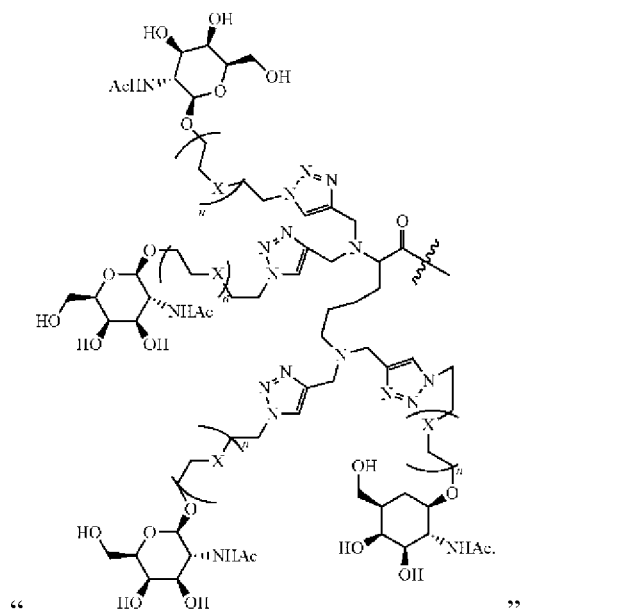 "

CERTIFICATE OF CORRECTION (continued)
U.S. Pat. No. 9,540,639 B2

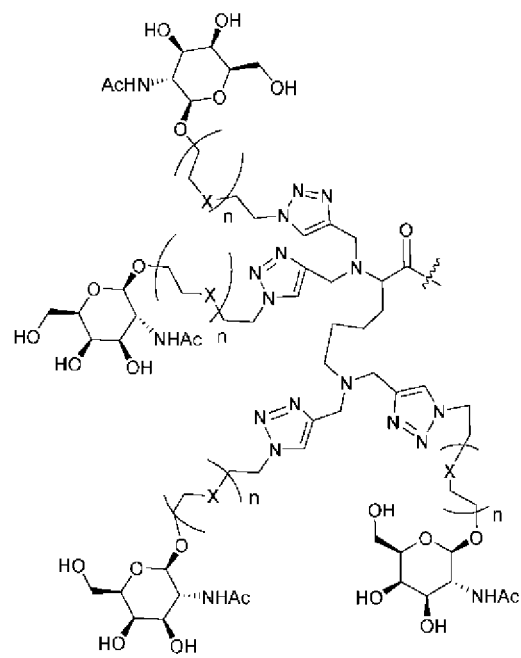

and insert in its place --                                    --.

In Claim 3, Column 118, between Lines 40 and 65, delete

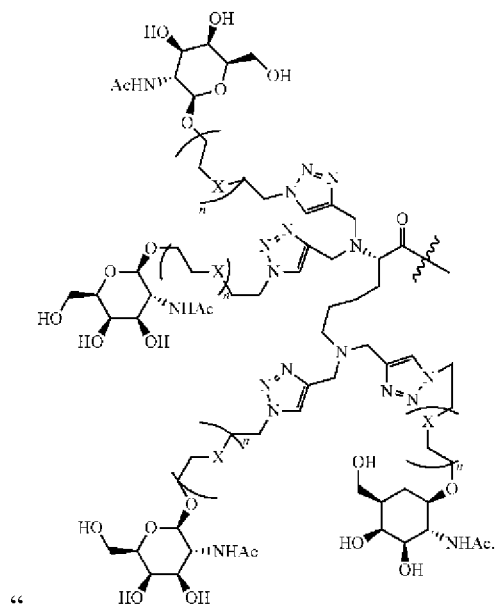

"                                                    "

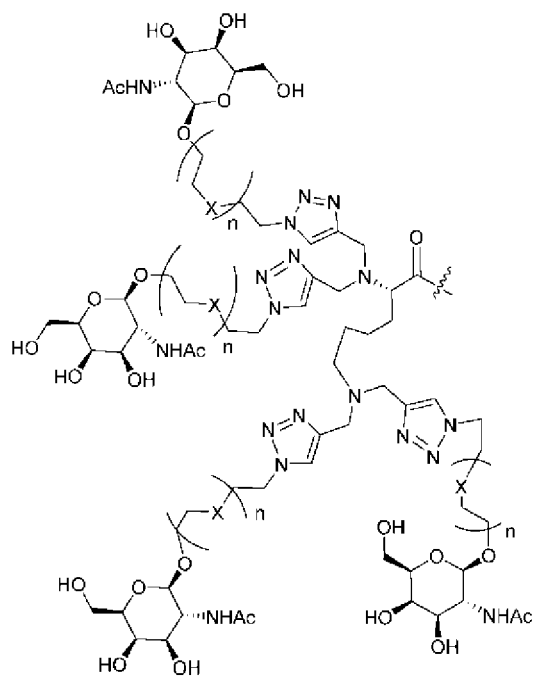
and insert in its place -- 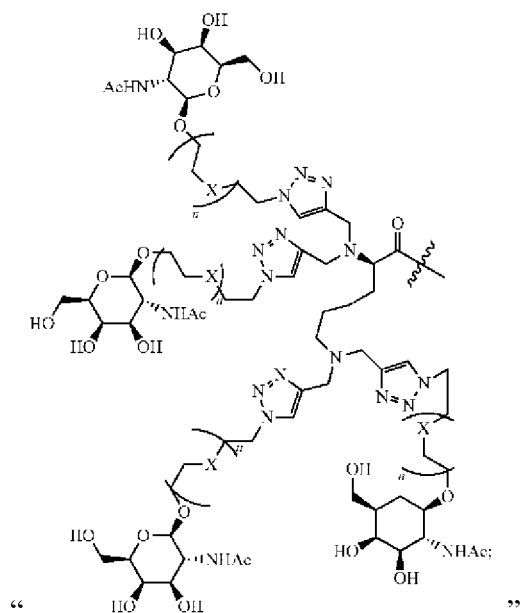 --.
In Claim 3, Column 119, between Lines 1 and 25, delete

CERTIFICATE OF CORRECTION (continued)
U.S. Pat. No. 9,540,639 B2 and insert in its place -- 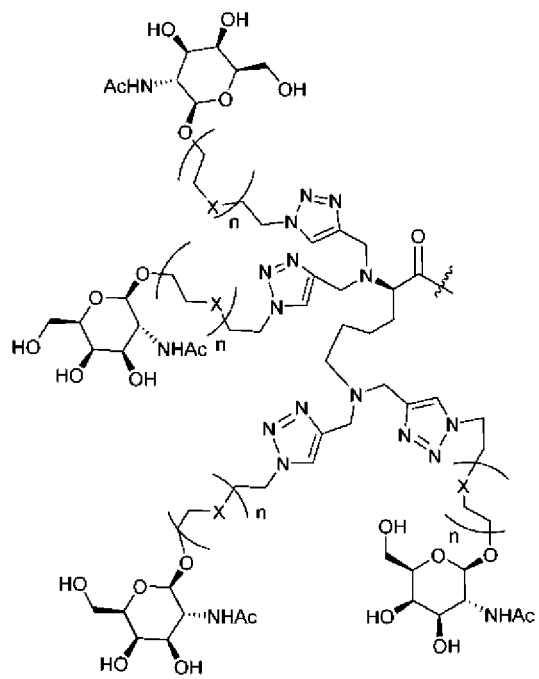 --.

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(4)
<223> OTHER INFORMATION: 2'-O-methyl
<220> FEATURE:
<221> NAME/KEY: misc_feature
<222> LOCATION: (5)..(6)
<223> OTHER INFORMATION: 2'-deoxy-2'-fluoro
<220> FEATURE:
```

```
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(9)
<223> OTHER INFORMATION: 2'-deoxy-2'-fluoro
<220> FEATURE:
<221> NAME/KEY: misc_feature
<222> LOCATION: (10)..(14)
<223> OTHER INFORMATION: 2'-O-methyl
<220> FEATURE:
<221> NAME/KEY: misc_feature
<222> LOCATION: (15)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 1
cuuuaacaau uccugaaaut t                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(10)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
<223> OTHER INFORMATION: phosphorothioate internucleotide linkage
```

```
<220> FEATURE:
<221> NAME/KEY: misc_feature
<222> LOCATION: (20)..(21)
<223> OTHER INFORMATION: phosphorothioate internucleotide linkage

<400> SEQUENCE: 2
auuucaggaa uuguuaaagu u                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(4)
<223> OTHER INFORMATION: 2'-O-methyl
<220> FEATURE:
<221> NAME/KEY: misc_feature
<222> LOCATION: (5)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(9)
<223> OTHER INFORMATION: 2'-deoxy-2'-fluoro
<220> FEATURE:
<221> NAME/KEY: misc_feature
<222> LOCATION: (10)..(14)
<223> OTHER INFORMATION: 2'-O-methyl
<220> FEATURE:
<221> NAME/KEY: misc_feature
<222> LOCATION: (15)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: aminohexyl phosphate inverted abasic cap

<400> SEQUENCE: 3
cuuuaacaau uccugaaaut t                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
```

```
<222> LOCATION: (6)..(10)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 4
auuucaggaa uuguuaaagu u                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2' propagyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
```

-continued

```
<220> FEATURE:
<221> NAME/KEY: misc_feature
<222> LOCATION: (8)..(9)
<223> OTHER INFORMATION: 2'-deoxy-2'-fluoro
<220> FEATURE:
<221> NAME/KEY: misc_feature
<222> LOCATION: (10)..(14)
<223> OTHER INFORMATION: 2'-O-methyl
<220> FEATURE:
<221> NAME/KEY: misc_feature
<222> LOCATION: (15)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2' propagyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 5
cuuuaacaau uccugaaaut t                                              21

<210> SEQ ID NO 6
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(10)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
```

```
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 6
auuucaggaa uuguuaaagu u                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(4)
<223> OTHER INFORMATION: 2'-O-methyl
<220> FEATURE:
<221> NAME/KEY: misc_feature
<222> LOCATION: (5)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(9)
<223> OTHER INFORMATION: 2'-deoxy-2'-fluoro
<220> FEATURE:
<221> NAME/KEY: misc_feature
<222> LOCATION: (10)..(14)
<223> OTHER INFORMATION: 2'-O-methyl
<220> FEATURE:
<221> NAME/KEY: misc_feature
<222> LOCATION: (15)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: aminohexyl phosphate inverted abasic cap

<400> SEQUENCE: 7
cuuuaacaau uccugaaaut t                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-O-methyl
<220> FEATURE:
```

```
<221> NAME/KEY: misc_feature
<222> LOCATION: (6)..(10)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 8
auuucaggaa uuguuaaagu u                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(4)
<223> OTHER INFORMATION: 2'-O-methyl
<220> FEATURE:
<221> NAME/KEY: misc_feature
<222> LOCATION: (5)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(9)
<223> OTHER INFORMATION: 2'-deoxy-2'-fluoro
<220> FEATURE:
<221> NAME/KEY: misc_feature
<222> LOCATION: (10)..(14)
```

```
<223> OTHER INFORMATION: 2'-O-methyl
<220> FEATURE:
<221> NAME/KEY: misc_feature
<222> LOCATION: (15)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 9
cuuuaacaau uccugaaaut t                                              21

<210> SEQ ID NO 10
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(10)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2' propagyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 10
auuucaggaa uuguuaaagu u                                              21
```

```
<210> SEQ ID NO 11
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 11
acaacagacu uuaauguaat t                                        21

<210> SEQ ID NO 12
<211> LENGTH: 21
<212> TYPE: RNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-O-methyl
<220> FEATURE:
<221> NAME/KEY: misc_feature
<222> LOCATION: (8)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 12
uuacauuaaa gucuguuguu u                                           21

<210> SEQ ID NO 13
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2' propagyl
<220> FEATURE:
<221> NAME/KEY: misc_feature
<222> LOCATION: (4)..(5)
```

<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2' propagyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (21)..(21)
<223> OTHER INFORMATION: inverted abasic cap
<220> FEATURE:
<221> NAME/KEY: misc_feature
<222> LOCATION: (21)..(21)
<223> OTHER INFORMATION: n-propylthiol
<220> FEATURE:
<221> NAME/KEY: misc_feature
<222> LOCATION: (20)..(21)
<223> OTHER INFORMATION: phosphorothioate internucleotide linkage

<400> SEQUENCE: 13
cuguuggauu gauucgaaau u                                              21

<210> SEQ ID NO 14
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature -continued

```
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 14
uuucgaauca auccaacagu u                                              21

<210> SEQ ID NO 15
<211> LENGTH: 21
<212> TYPE: RNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2' propagyl
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2' propagyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (21)..(21)
<223> OTHER INFORMATION: inverted abasic cap
<220> FEATURE:
<221> NAME/KEY: misc_feature
<222> LOCATION: (21)..(21)
<223> OTHER INFORMATION: n-propylthiol
<220> FEATURE:
<221> NAME/KEY: misc_feature
<222> LOCATION: (20)..(21)
<223> OTHER INFORMATION: phosphorothioate internucleotide linkage

<400> SEQUENCE: 15 cguguuggauu gauucgaaau u                                      21

<210> SEQ ID NO 16
<211> LENGTH: 21
<212> TYPE: RNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2' propagyl
<220> FEATURE:
<221> NAME/KEY: misc_feature
<222> LOCATION: (16)..(16)
<223> OTHER INFORMATION: 2'-deoxy-2'-fluoro
```

```
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(4)
<223> OTHER INFORMATION: phosphorothioate internucleotide linkage
<220> FEATURE:
<221> NAME/KEY: misc_feature
<222> LOCATION: (20)..(21)
<223> OTHER INFORMATION: phosphorothioate internucleotide linkage

<400> SEQUENCE: 16
uuucgaauca auccaacagu u                                              21
```